(12) United States Patent
Rajagopal et al.

(10) Patent No.: US 12,004,952 B2
(45) Date of Patent: Jun. 11, 2024

(54) TRANSCATHETER ANCHOR SUPPORT, SYSTEMS AND METHODS OF IMPLANTATION

(71) Applicant: OPUS MEDICAL THERAPIES, LLC, Atlanta, GA (US)

(72) Inventors: Vivek Rajagopal, Atlanta, GA (US); Jaime Eduardo Sarabia, Mableton, GA (US); Yenchin Liao, Cary, NC (US); Johnny Zhang, Atlanta, GA (US); Alfred H Raschdorf, Jr., Atlanta, GA (US)

(73) Assignee: OPUS MEDICAL THERAPIES, LLC, Atlanta, GA (US)

(*) Notice: Subject to any disclaimer, the term of this patent is extended or adjusted under 35 U.S.C. 154(b) by 285 days.

(21) Appl. No.: 17/156,144

(22) Filed: Jan. 22, 2021

(65) Prior Publication Data

US 2021/0220130 A1 Jul. 22, 2021

Related U.S. Application Data

(60) Provisional application No. 63/122,934, filed on Dec. 8, 2020, provisional application No. 63/058,763, filed
(Continued)

(51) Int. Cl.
*A61F 2/24* (2006.01)
*A61B 17/00* (2006.01)
*A61B 17/04* (2006.01)

(52) U.S. Cl.
CPC ........ *A61F 2/2487* (2013.01); *A61B 17/0057* (2013.01); *A61B 17/0401* (2013.01);
(Continued)

(58) Field of Classification Search
CPC .. A61F 2/2487; A61F 2/2457; A61B 17/0057; A61B 17/0401; A61B 2017/0441; A61B 2017/0445
See application file for complete search history.

(56) References Cited

U.S. PATENT DOCUMENTS 4,242,715 A 12/1980 Laird
4,337,496 A 6/1982 Laird
(Continued)

FOREIGN PATENT DOCUMENTS

AU 2016202264 A1 11/2016
CA 3 059 102 A1 10/2018
(Continued)

OTHER PUBLICATIONS

International Search Report issued in corresponding International Application No. PCT/US2021/052954 dated Dec. 22, 2021.
(Continued)

*Primary Examiner* — Suba Ganesan
(74) *Attorney, Agent, or Firm* — Pierson Ferdinand LLP; Rachel H. Huffstetler

(57) ABSTRACT

A minimally invasively implanted anchor support for securing a medical device to a heart wall including an anchoring member and an expandable distal anchor retraint which is implanted through the anchoring member, through the heart wall, and expands on the opposing heart wall side to anchor a medical device. A single-stage anchor system includes the distal flange and a two-stage anchor system includes the distal flange and a proximal flange which cooperates with the distal flange to secure a medical device to the heart wall and methods of a single-stage anchor system and a two-stage anchor system.

13 Claims, 60 Drawing Sheets

Related U.S. Application Data on Jul. 30, 2020, provisional application No. 62/964,371, filed on Jan. 22, 2020.

(52) U.S. Cl.
CPC .......... *A61F 2/2457* (2013.01); *A61F 2/2466* (2013.01); *A61B 2017/0441* (2013.01); *A61B 2017/0445* (2013.01); *A61F 2/2418* (2013.01); *A61F 2/2427* (2013.01); *A61F 2002/249* (2013.01); *A61F 2220/0016* (2013.01)

(56) References Cited

U.S. PATENT DOCUMENTS

| | | | |
|---|---|---|---|
| 4,746,057 | A | 5/1988 | Wagner |
| 4,830,360 | A | 5/1989 | Carr, Jr. |
| 5,079,776 | A | 1/1992 | Crawford |
| 5,312,438 | A | 5/1994 | Johnson |
| 5,683,451 | A | 11/1997 | Lenker et al. |
| 5,706,520 | A | 1/1998 | Thornton et al. |
| 6,093,162 | A | 7/2000 | Fairleigh et al. |
| 7,530,995 | B2 | 5/2009 | Quijano et al. |
| 7,780,725 | B2 | 8/2010 | Haug et al. |
| 8,147,542 | B2 | 4/2012 | Maisano et al. |
| 8,236,049 | B2 | 8/2012 | Rowe et al. |
| 8,252,050 | B2 | 8/2012 | Maisano et al. |
| 8,273,973 | B2 | 9/2012 | Kimmons et al. |
| 8,333,155 | B2 | 12/2012 | Cylwick |
| 8,403,983 | B2 | 3/2013 | Quadri et al. |
| 8,449,599 | B2 | 5/2013 | Chau et al. |
| 8,489,165 | B2 | 7/2013 | Segman |
| 8,545,553 | B2 | 10/2013 | Zipory et al. |
| 8,549,175 | B2 | 10/2013 | Krishna |
| 8,690,939 | B2 | 4/2014 | Miller et al. |
| 8,728,155 | B2 | 5/2014 | Montorfano et al. |
| 8,790,394 | B2 | 7/2014 | Miller et al. |
| 8,888,843 | B2 | 11/2014 | Khairkhahan et al. |
| 8,900,295 | B2 | 12/2014 | Migliazza et al. |
| 8,932,348 | B2 | 1/2015 | Solem et al. |
| 8,998,976 | B2 | 4/2015 | Gregg et al. |
| 9,005,084 | B2 | 4/2015 | Silagy et al. |
| 9,033,383 | B2 | 5/2015 | Rampersad |
| 9,034,033 | B2 | 5/2015 | McLean et al. |
| 9,078,749 | B2 | 7/2015 | Lutter et al. |
| 9,375,312 | B2 | 6/2016 | Weber |
| 9,439,763 | B2 | 9/2016 | Geist et al. |
| 9,441,832 | B2 | 9/2016 | Bushee |
| 9,474,605 | B2 | 10/2016 | Rowe et al. |
| 9,480,559 | B2 | 11/2016 | Vidlund et al. |
| 9,486,306 | B2 | 11/2016 | Tegels et al. |
| 9,578,982 | B2 | 2/2017 | Rampersad |
| 9,827,092 | B2 | 11/2017 | Vidlund et al. |
| 9,849,001 | B2 | 12/2017 | Thompson, Jr. et al. |
| 9,877,833 | B1 | 1/2018 | Bishop |
| 9,895,221 | B2 | 2/2018 | Vidlund |
| 9,986,993 | B2 | 6/2018 | Vidlund et al. |
| 10,039,639 | B2 | 8/2018 | Marchand et al. |
| 10,219,900 | B2 | 3/2019 | Vidlund |
| 2004/0049207 | A1 | 3/2004 | Goldfarb |
| 2004/0116992 | A1 | 6/2004 | Wardle et al. |
| 2004/0190383 | A1 | 9/2004 | Marcucelli et al. |
| 2005/0137697 | A1 | 6/2005 | Salahieh et al. |
| 2006/0235509 | A1 | 10/2006 | Lafontaine |
| 2006/0241656 | A1 | 10/2006 | Starksen et al. |
| 2006/0241745 | A1 | 10/2006 | Solem |
| 2007/0049980 | A1 | 3/2007 | Zielinkski et al. |
| 2007/0066863 | A1* | 3/2007 | Rafiee ................ A61B 17/0401 606/151 |
| 2007/0073351 | A1 | 3/2007 | Zielinski et al. |
| 2007/0118151 | A1 | 5/2007 | Davidson |
| 2007/0265658 | A1 | 11/2007 | Nelson |
| 2007/0277279 | A1 | 12/2007 | Battat |
| 2008/0004485 | A1 | 1/2008 | Moreschi |
| 2008/0109069 | A1 | 5/2008 | Coleman |
| 2008/0125860 | A1 | 5/2008 | Webler et al. |
| 2009/0012557 | A1* | 1/2009 | Osypka ............... A61B 17/0057 604/93.01 |
| 2009/0276040 | A1 | 11/2009 | Rowe et al. |
| 2010/0016655 | A1 | 1/2010 | Annest et al. |
| 2010/0161041 | A1 | 6/2010 | Maisano et al. |
| 2011/0004296 | A1 | 1/2011 | Lutter et al. |
| 2011/0112737 | A1 | 5/2011 | Neelakantan et al. |
| 2011/0312018 | A1 | 12/2011 | Shusta et al. |
| 2012/0078360 | A1 | 3/2012 | Rafiee |
| 2012/0136430 | A1 | 5/2012 | Sochman et al. |
| 2013/0023985 | A1 | 1/2013 | Khairkhahan et al. |
| 2013/0172978 | A1 | 7/2013 | Vidlund et al. |
| 2013/0184811 | A1 | 7/2013 | Rowe et al. |
| 2013/0190861 | A1 | 7/2013 | Chau et al. |
| 2013/0211508 | A1 | 8/2013 | Lane et al. |
| 2013/0304197 | A1 | 11/2013 | Buchbinder et al. |
| 2013/0331929 | A1 | 12/2013 | Mitra et al. |
| 2014/0005778 | A1 | 1/2014 | Buchbinder et al. |
| 2014/0031928 | A1 | 1/2014 | Murphy et al. |
| 2014/0163668 | A1 | 6/2014 | Rafiee |
| 2014/0296972 | A1 | 10/2014 | Tegels et al. |
| 2014/0316516 | A1 | 10/2014 | Vidlund et al. |
| 2014/0379076 | A1 | 12/2014 | Vidlund et al. |
| 2015/0142103 | A1 | 5/2015 | Vidlund |
| 2015/0157268 | A1 | 6/2015 | Winshtein et al. |
| 2015/0250590 | A1 | 9/2015 | Gries et al. |
| 2015/0305861 | A1 | 10/2015 | Annest |
| 2015/0342602 | A1 | 12/2015 | Jimenez et al. |
| 2015/0366666 | A1 | 12/2015 | Khairkhahan et al. |
| 2016/0022501 | A1 | 1/2016 | Schultz et al. |
| 2016/0067395 | A1 | 3/2016 | Jimenez et al. |
| 2016/0120646 | A1 | 5/2016 | Dwork et al. |
| 2016/0213467 | A1 | 7/2016 | Backus et al. |
| 2016/0262878 | A1 | 9/2016 | Backus et al. |
| 2016/0262881 | A1 | 9/2016 | Schankereli et al. |
| 2016/0310268 | A1 | 10/2016 | Oba et al. |
| 2016/0317305 | A1 | 11/2016 | Pelled et al. |
| 2016/0324635 | A1 | 11/2016 | Vidlund et al. |
| 2016/0367360 | A1 | 12/2016 | Cartledge et al. |
| 2016/0367368 | A1 | 12/2016 | Vidlund |
| 2017/0143478 | A1 | 5/2017 | Schwartz et al. |
| 2017/0209293 | A1 | 7/2017 | Combs |
| 2017/0227320 | A1 | 8/2017 | Derousse |
| 2018/0085215 | A1 | 3/2018 | Vaturi et al. |
| 2018/0140421 | A1 | 5/2018 | Sampson |
| 2018/0289473 | A1 | 10/2018 | Rajagopal et al. |
| 2018/0289474 | A1 | 10/2018 | Rajagopal et al. |
| 2018/0289485 | A1 | 10/2018 | Rajagopal et al. |
| 2018/0318071 | A1 | 11/2018 | Lozonschi et al. |
| 2019/0015205 | A1 | 1/2019 | Rajagopal et al. |
| 2020/0001135 | A1 | 1/2020 | Rajagopal |
| 2020/0069426 | A1 | 3/2020 | Conklin |
| 2020/0078000 | A1 | 3/2020 | Rajagopal |
| 2020/0178977 | A1 | 6/2020 | Coleman |
| 2020/0330228 | A1 | 10/2020 | Anderson et al. |
| 2020/0397571 | A1 | 12/2020 | Rajagopal |
| 2021/0093454 | A1 | 4/2021 | Sampson |
| 2021/0220130 | A1 | 7/2021 | Rajagopal |
| 2022/0104941 | A1 | 4/2022 | Rajagopal |

FOREIGN PATENT DOCUMENTS

| | | |
|---|---|---|
| CA | 3 059 106 A1 | 10/2018 |
| CN | 103826750 A | 5/2014 |
| CN | 106618798 A | 5/2017 |
| CN | 105658178 B | 5/2018 |
| DE | 10 2012 002 785 A1 | 8/2013 |
| EP | 1 462 880 A2 | 9/2004 |
| EP | 1 462 880 A3 | 4/2005 |
| EP | 3 311 774 A1 | 4/2018 |
| KR | 10-2020-0007805 A | 1/2020 |
| KR | 10-2020-0007806 A | 1/2020 |
| UY | 37667 A | 10/2018 |
| UY | 37668 A | 10/2018 |
| WO | 1994/020049 A1 | 9/1994 |
| WO | 2005/094711 A2 | 10/2005 |
| WO | 2014/021905 A1 | 2/2014 |
| WO | 2016/050751 A1 | 4/2016 |
| WO | 2016/179427 A1 | 11/2016 |

(56) References Cited

FOREIGN PATENT DOCUMENTS

| WO | 2016/186909 A1 | 11/2016 |
| WO | DM/098 100 S | 6/2017 |
| WO | 2017/117560 A1 | 7/2017 |
| WO | 2018/187390 A1 | 10/2018 |
| WO | 2018/187495 A1 | 10/2018 |
| WO | 2020/005527 A1 | 1/2020 |

OTHER PUBLICATIONS

International Search Report and Written Opinion in corresponding International application No. PCT/US2018/025971 dated Jul. 10, 2018.

International Search Report and Written Opinion in corresponding International application No. PCT/US2018/026118 dated Jun. 15, 2018.

Toyama et al. Mitral annular motion in patients after transcatheter MitraClip and mitral valve surgery; Echocardiography 2017; 34:334-339.

Boudjemline Y, Agnoletti G, Bonnel D, et al. Steps toward the percutaneous replacement of atrioventricular valves an experimental study. Journal of the American College of Cardiology 2005; 46:360-5.

Bai Y, Chen HY, Zang GJ, et al. Percutaneous establishment of tricuspid regurgitation: an experimental model for transcatheter tricuspid valve replacement. Chinese medical journal 2010; 123:806-9.

Laule M, Stangl V, Sanad W, Lembcke A, Baumann G, Stangl K. Percutaneous transfemoral management of severe secondary tricuspid regurgitation with Edwards Sapien XT bioprosthesis: first-in-man experience. Journal of the American College of Cardiology 2013; 61:1929-31.

Auten A, Doenst T, Hamadanchi A, Franz M, Figulla HR. Percutaneous bicaval valve implantation for transcatheler treatment of tricuspid regurgitation: clinical observations and 12-month follow-up. Circulation Cardiovascular Interventions 2014; 7:268-72.

Lauten A, Ferrari M, Hekmal K, et al. Heterotopic transcatheter tricuspid valve implantation: first-in-man application of a novel approach to tricuspid regurgitation. European heart journal 2011; 32:1207-13.

Lauten A, Figulla HR, Unbehaun A, et al. Interventional Treatment of Severe Tricuspid Regurgitation: Early Clinical Experience in a Multicenter, Observational, First-in-Man Study. Circulation Cardiovascular interventions 2018; 11: e006061.

Lauten A, Figulla HR, Willich C, et al. Percutaneous caval stent valve implantation: investigation of an interventional approach for treatment of tricuspid regurgitation. European heart journal 2010; 31:1274-81.

Lauten A, Laube A, Schubert H, et al. Transcatheter treatment of tricuspid regurgitation by caval valve implantation-experimental evaluation of decellularized tissue valves in central venous position. Catheterization and cardiovascular Interventions : official journal of the Society for Cardiac Angiography & Interventions 2014.

Figulla HR, Kiss K, Lauten A. Transcatheter interventions for tricuspid regurgitation—heterotopic technology: TricValve. EuroIntervention : journal of EuroPCR in collaboration with the Working Group on Interventional Cardiology of the European Society of Cardiology 2016; 12:Y116-8.

Barbanti M, Ye J, Pasupati S, El-Gamel A, Webb JG. The Helie transcatheter aortic dock for patients with aortic regurgitation. EuroIntervention : journal of EuroPCR in collaboration with the Working Group on Interventional Cardiology of the European Society of Cardiology 2013; 9 Suppl:S91-4.

Hahn RT, Meduri CU, Davidson CJ, et al. Early Feasibility Study of a Transcatheter Tricuspid Valve Annuloplasty: SCOUT Trial 30-Day Results. Journal of the American College of Cardiology 2017; 69:1795-806.

Rosser BA, Taramasso M, Maisano F. Transcatheter interventions for tricuspid regurgitation: TriCinch (4Tech). EuroIntervention : journal of EuroPCR in collaboration with the Working Group on Interventional Cardiology of the European Society of Cardiology 2016; 12:Y110-2.

Stephan van Bardeleben R, Tamm A, Emrich T, Munzel T, Schulz E. Percutaneous transvenous direct annuloplasty of a human tricuspid valve using the Valtech Cardioband. European heart journal 2017; 38:690.

Kuwata S, Taramasso M, Nietlispach F, Maisano F. Transcatheter tricuspid valve repair toward a surgical standard: first-in-man report of direct annuloplasty with a cardioband device to treat severe functional tricuspid regurgitation. European heart journal 2017.

Rogers J. Transcatheter TR solution 6: Millipede. Transcatheter Cardiovascular Therapeutics; 2017 Nov. 1, 2017; Denver, Colorado.

Parada-Campelo F, Perlman G, Philippon F, et al. First-in-Man Experience of a Novel Transcatheter Repair System for Treating Severe Tricuspid Regurgitation Journal of the American College of Cardiology 2015; 66:2475-83.

Nickenig G, Kowalski M, Hausleiter J, et al. Transcatheter Treatment of Severe Tricuspid Regurgitation With the Edge-to-Edge MitraClip Technique. Circulation 2017; 135:1802-14.

Cao P. Catheter-Based Tricuspid Valve Replacement Via Right Atrium: An Animal Experimental Study. Transcatheter Cardiovascular Therapeutics; 2017; Denver, Colorado.

Navia JL, Kapadia S, Elgharably H, et al. First-in-Human Implantations of the NaviGate Bioprosthesis in a Severely Dilated Tricuspid Annulus and in a Failed Tricuspid Annuloplasty Ring. Circulation Cardiovascular interventions 2017; 10.

Regueiro, et al. Transcatheter Mitral Valve Replacement: Insights From Early Clinical Experience and Future challenges; JACC vol. 69, No. 17, 2017; May 2, 2017: 2175-92.

Non-Final Office Action received for U.S. Appl. No. 15/943,792 dated Jan. 8, 2020, 50 pages.

International Search Report and Written Opinion of the International Searching Authority dated Aug. 30, 2019, in International Application No. PCT/US19/36428.

Non-Final Office Action received for U.S. Appl. No. 15/943,971 dated Jan. 8, 2020, 49 pages.

International Preliminary Report on Patentability received for PCT Application Serial No. PCT/US2018/025971 dated Oct. 17, 2019, 9 pages.

International Preliminary Report on Patentability received for PCT Application Serial No. PCT/US2018/026118 dated Oct. 17, 2019, 11 pages.

International Search Report and Written Opinion in corresponding International application No. PCT/ JS2019/57145 dated Dec. 31, 2019.

International Search Report and Written Opinion in corresponding International application No. PCT/ US2021/014644 dated Apr. 9, 2021.

Japanese Office Action (including English translation) issued in JP2022544097 dated Apr. 12, 2024, 12 pages.

\* cited by examiner

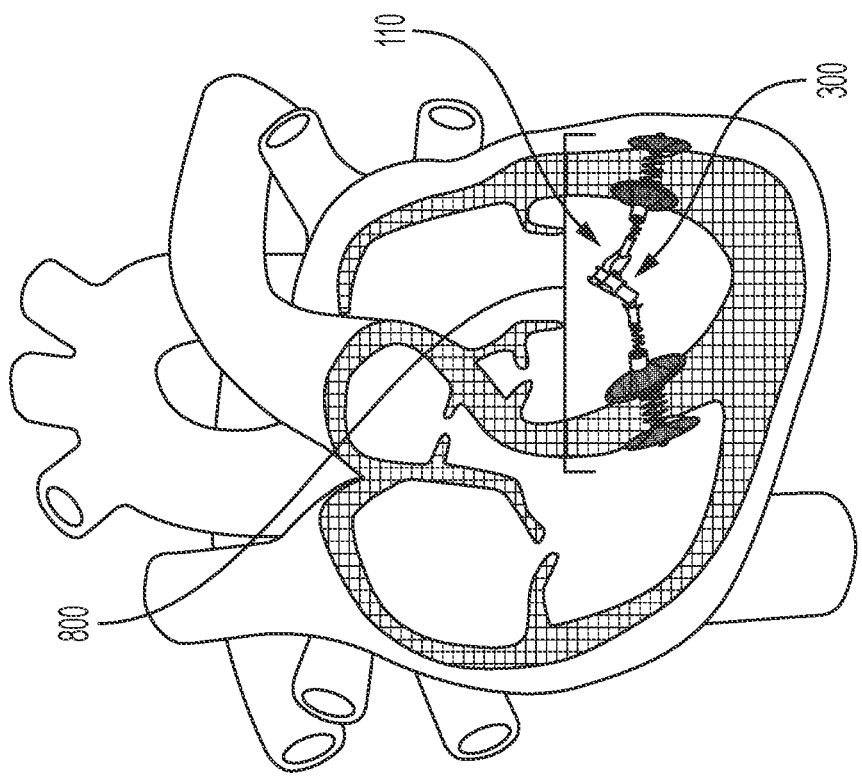
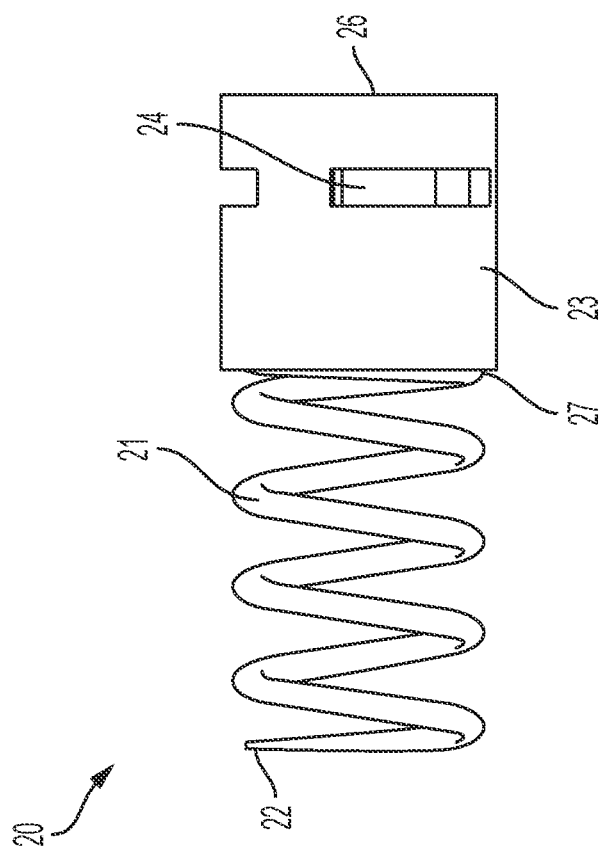
FIG. 7
FIG. 8

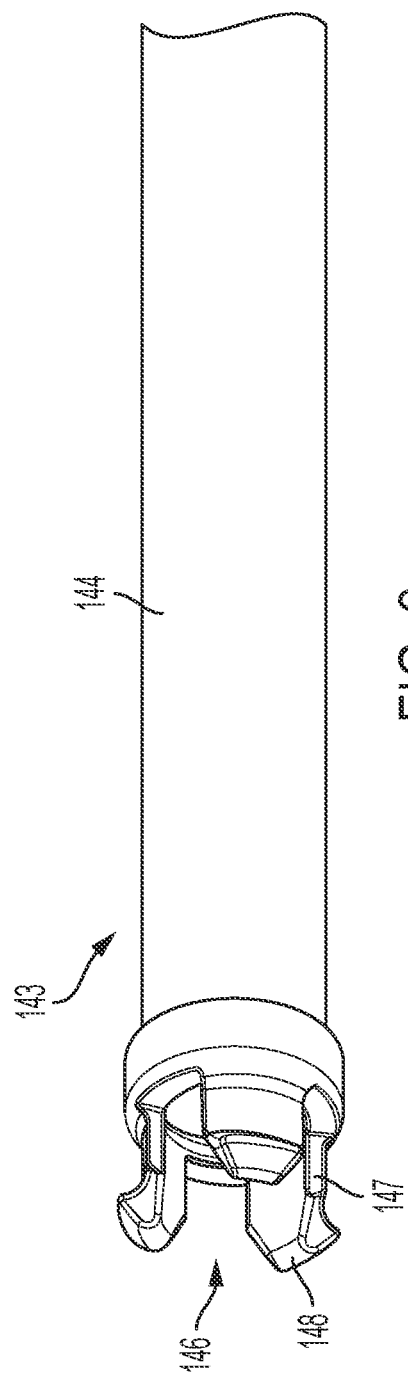
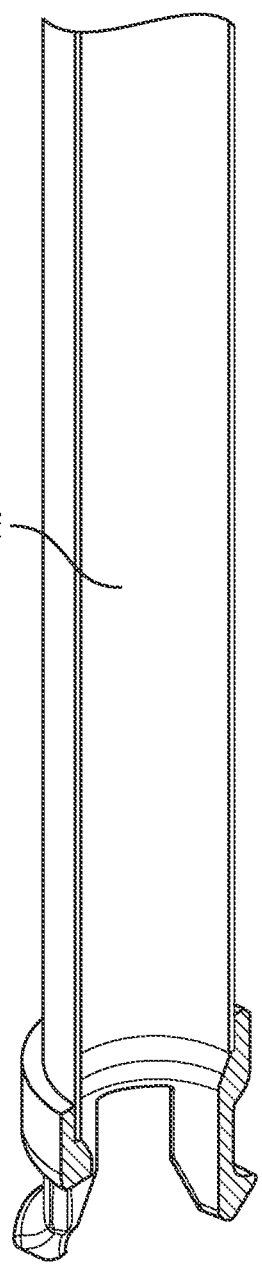
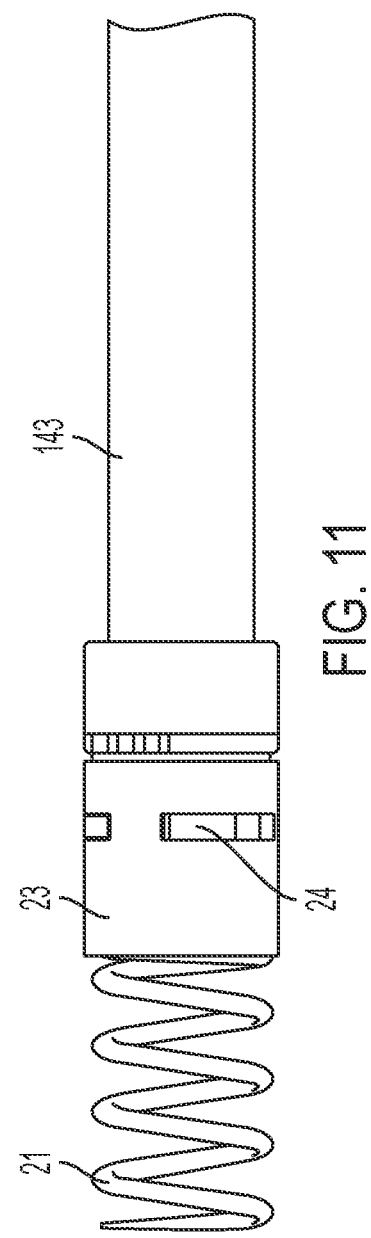

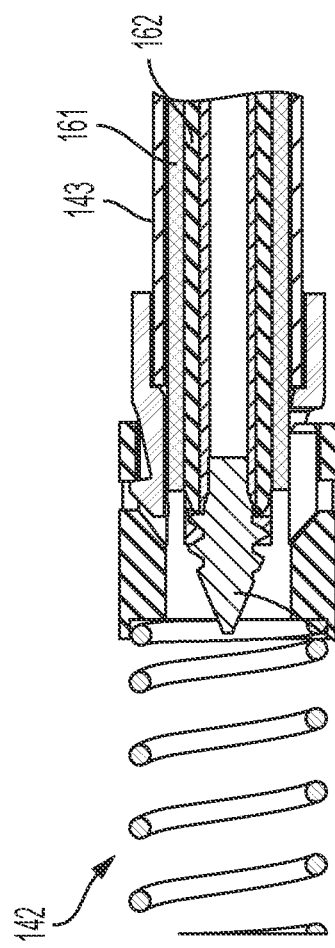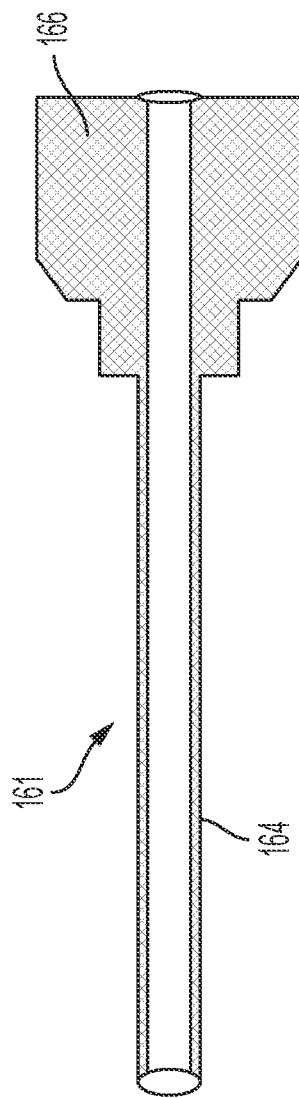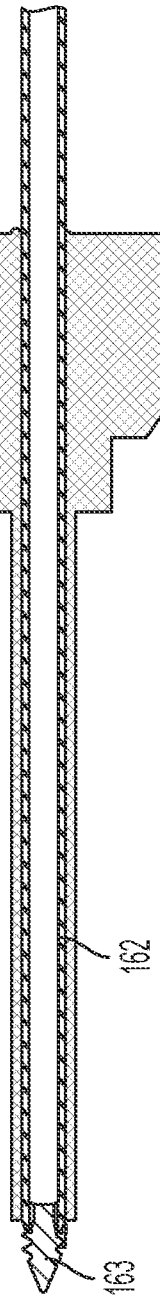
FIG. 12
FIG. 13A
FIG. 13B

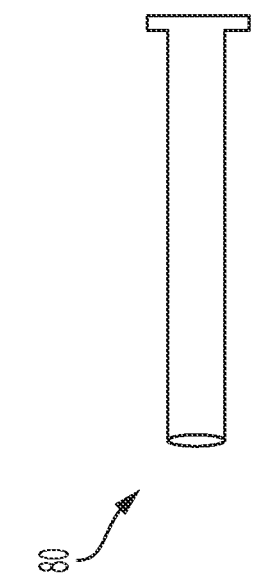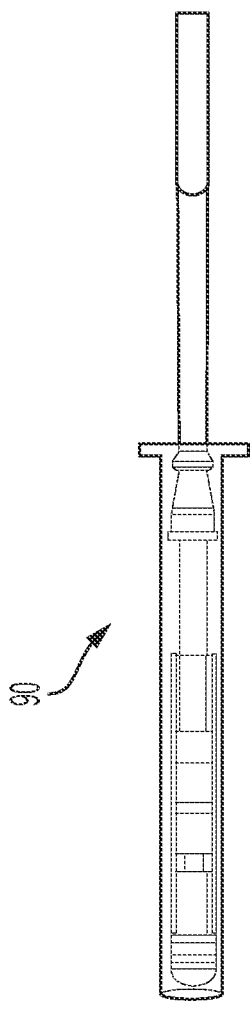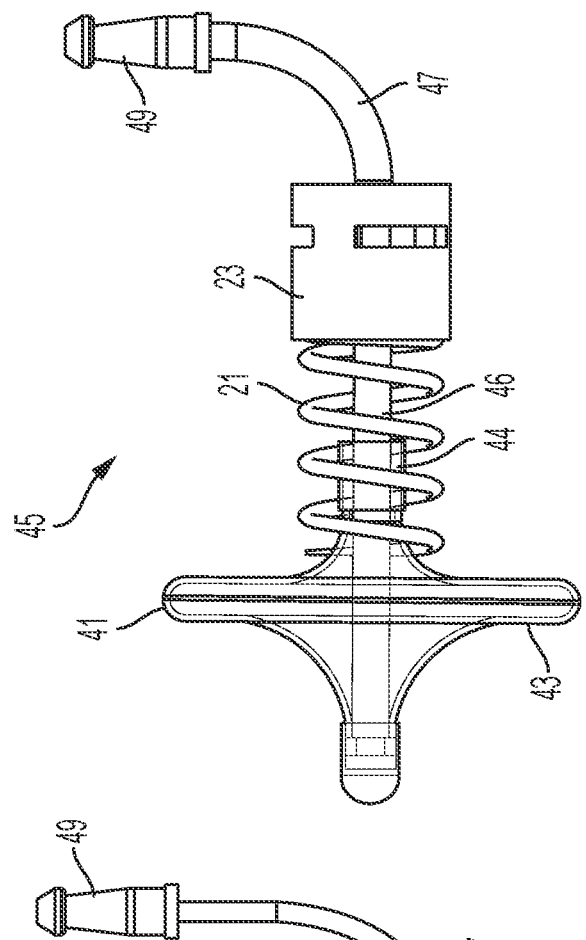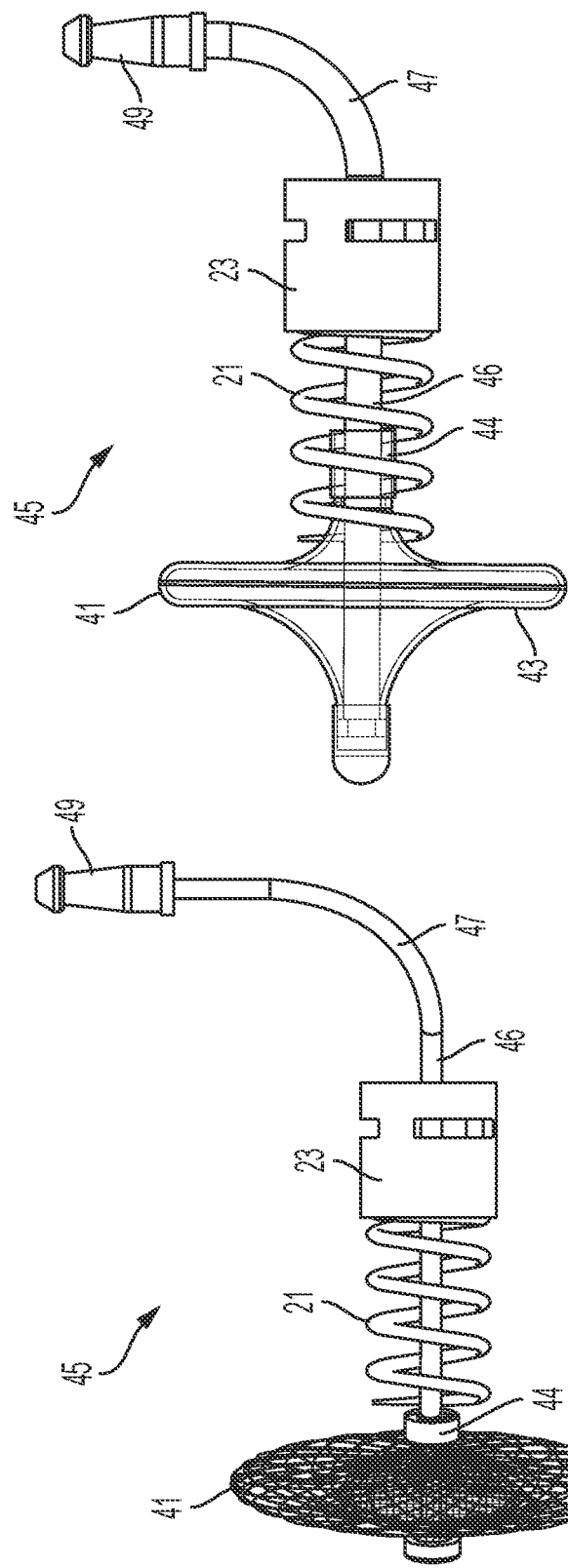

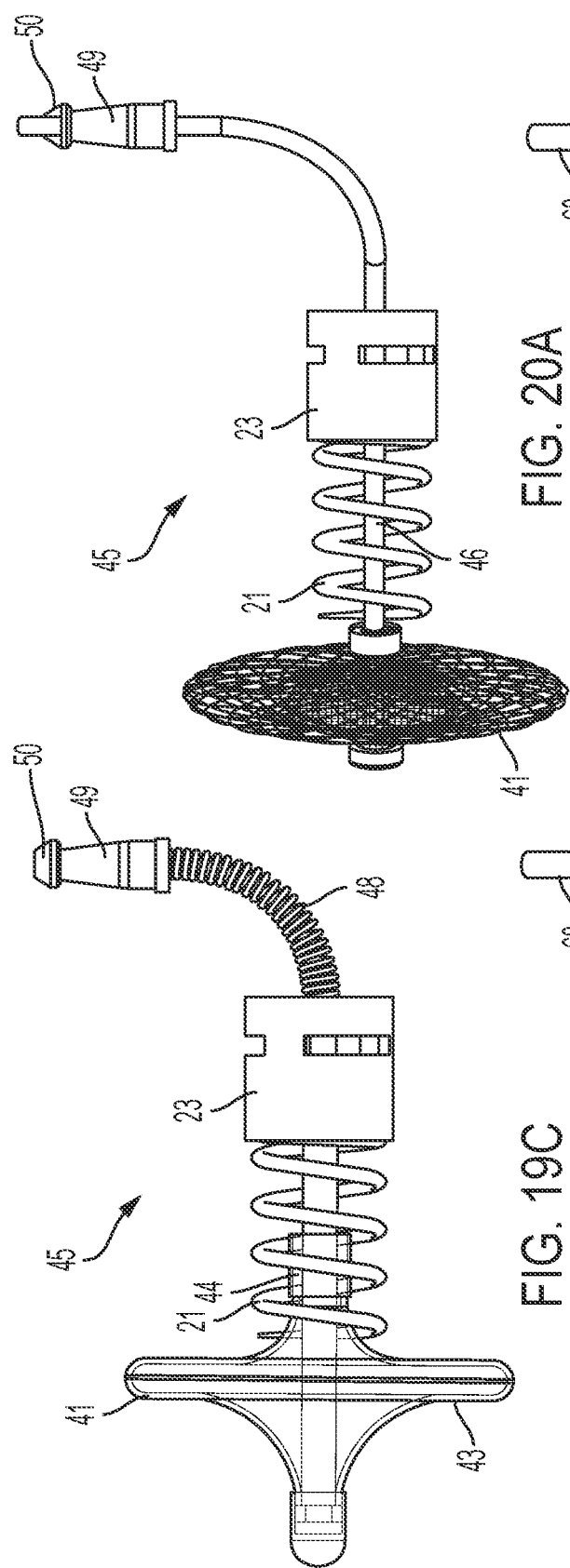
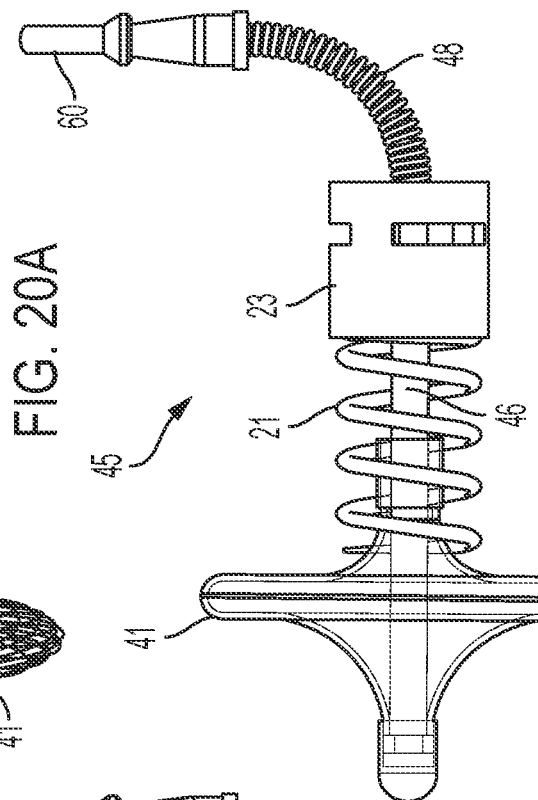
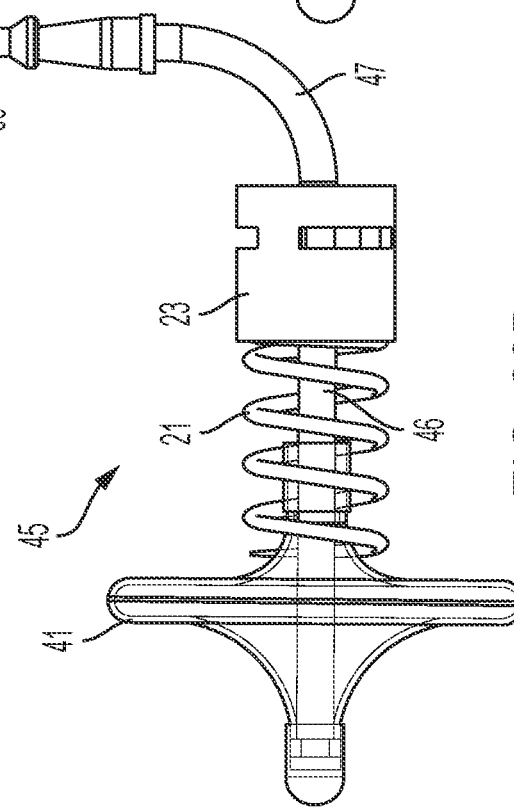
FIG. 19C
FIG. 20A
FIG. 20B
FIG. 20C

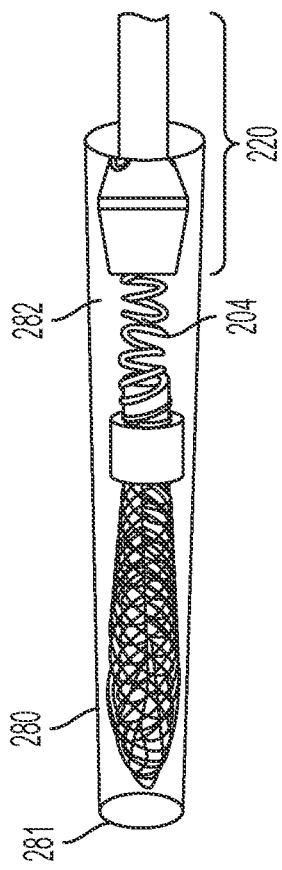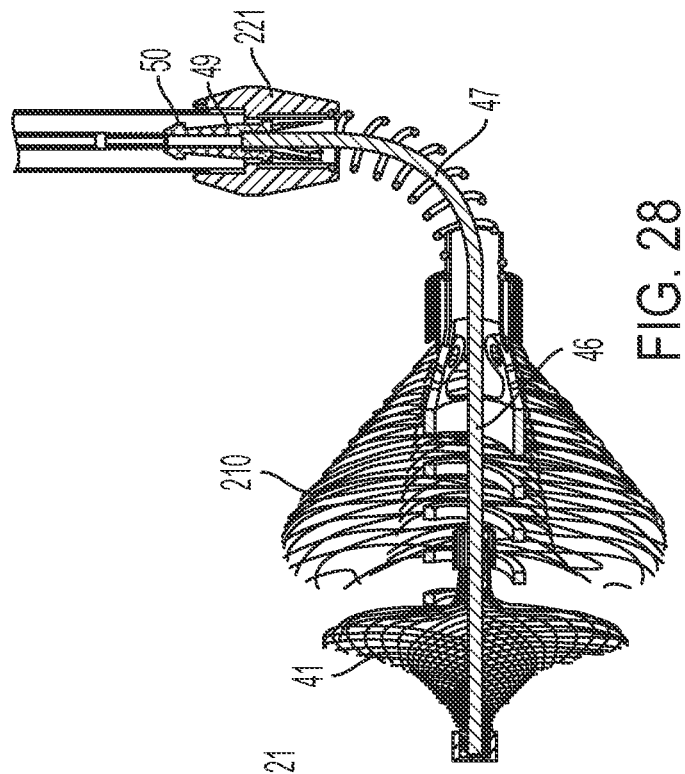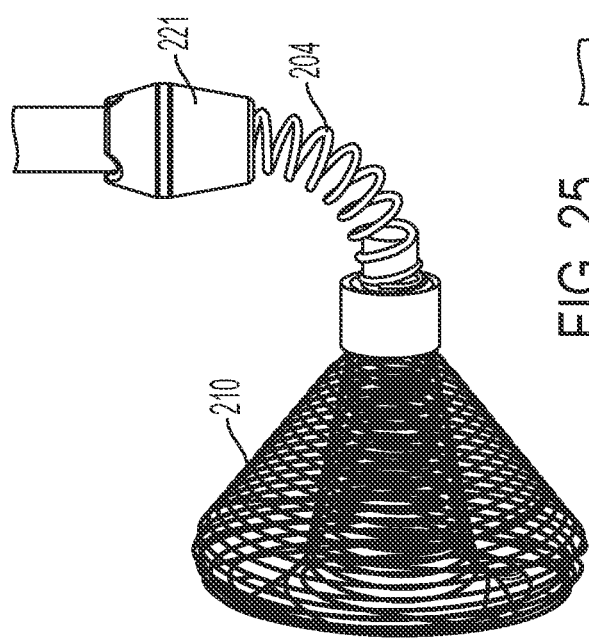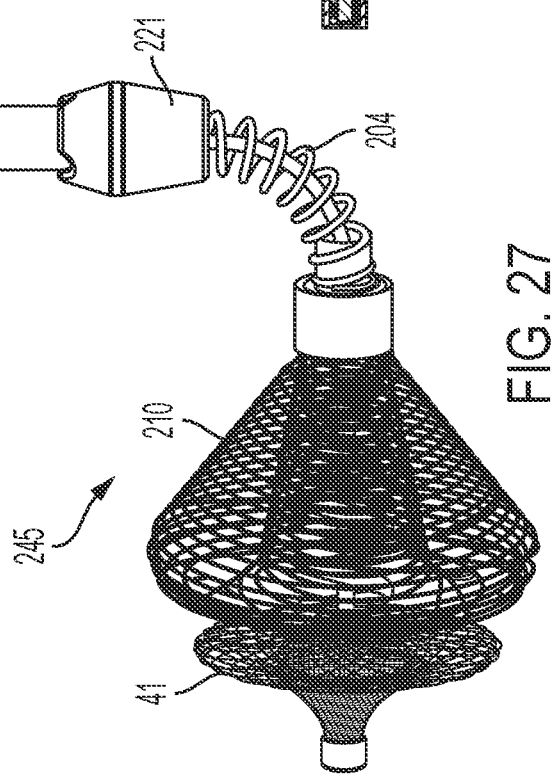

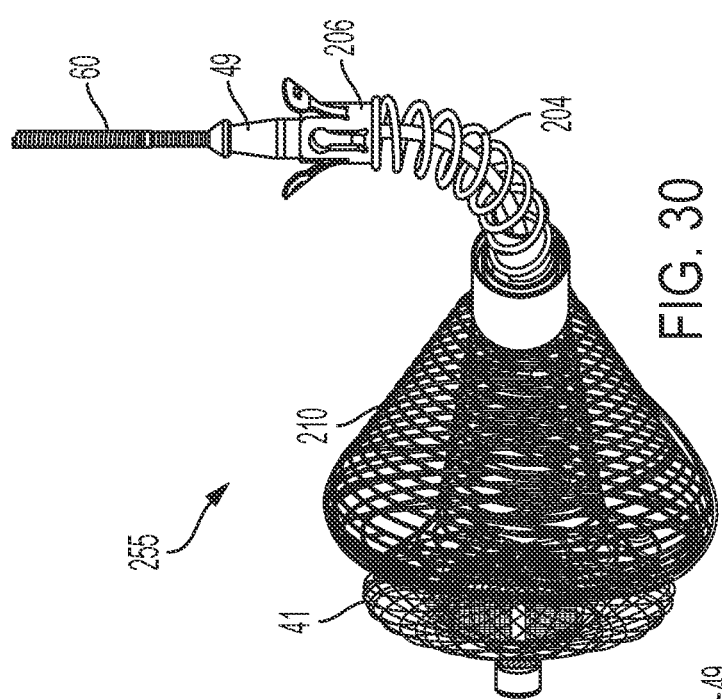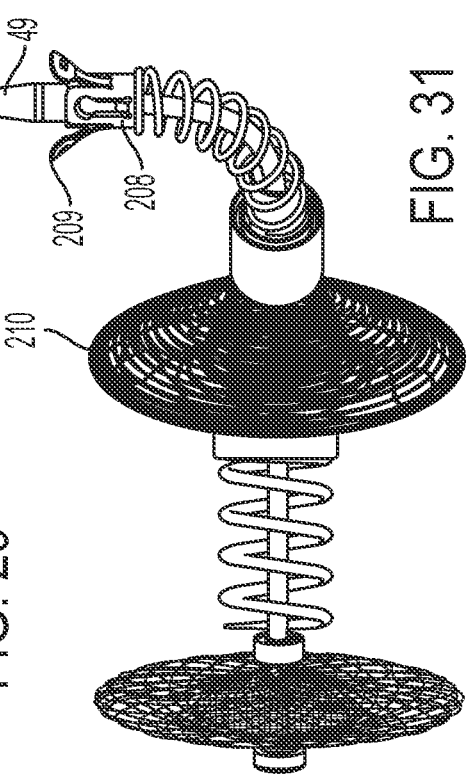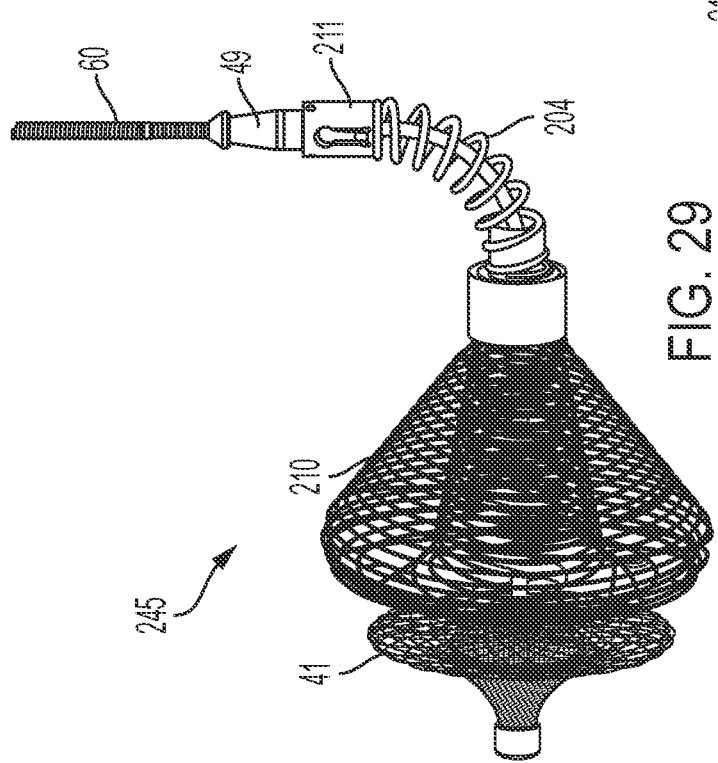

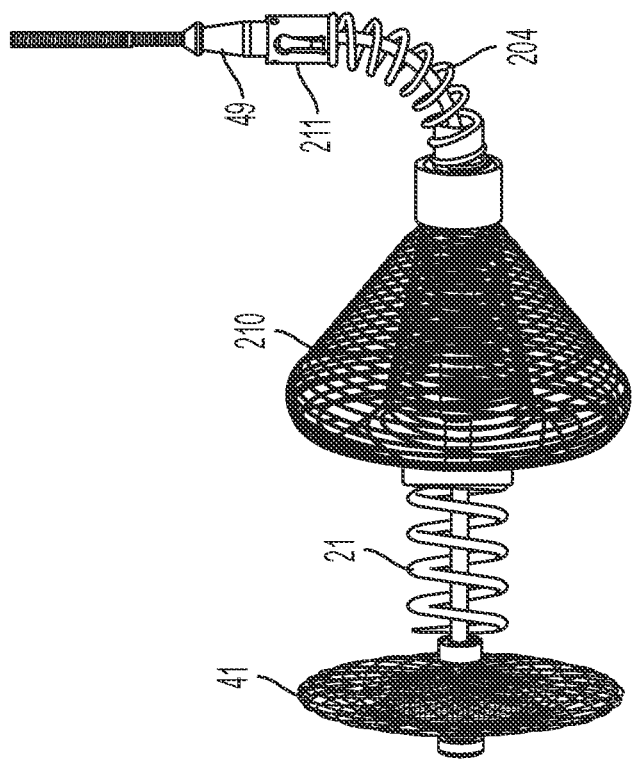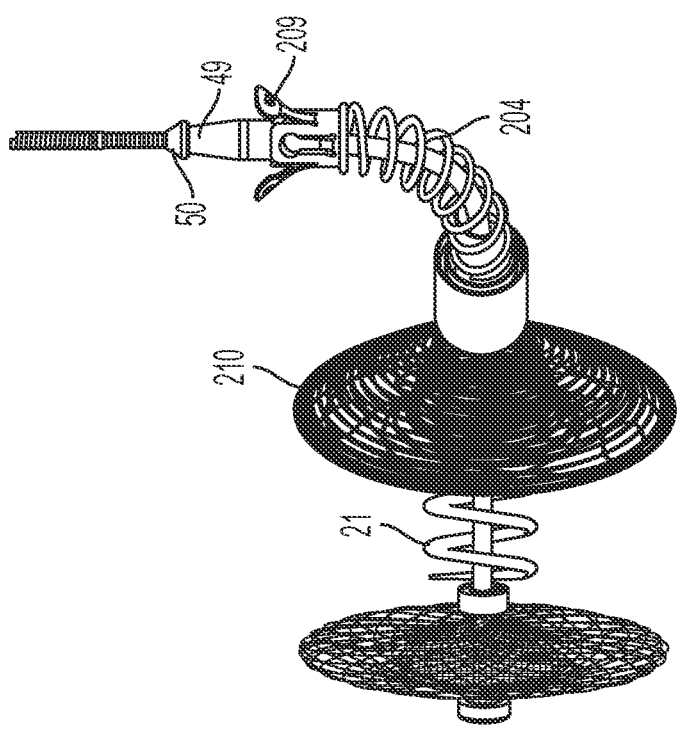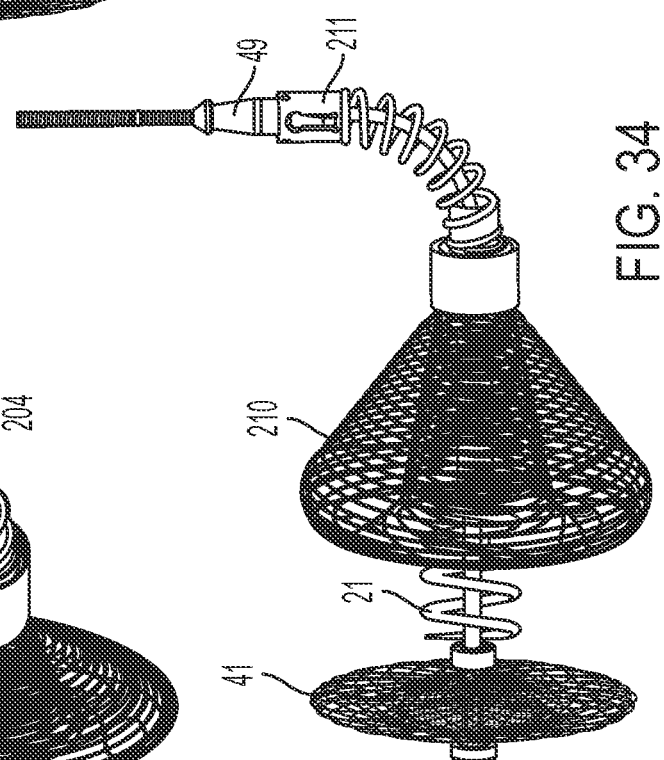

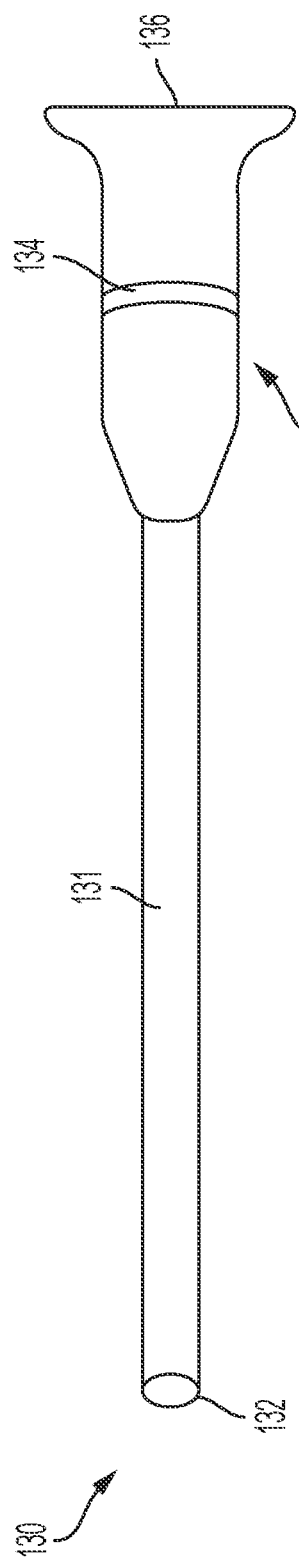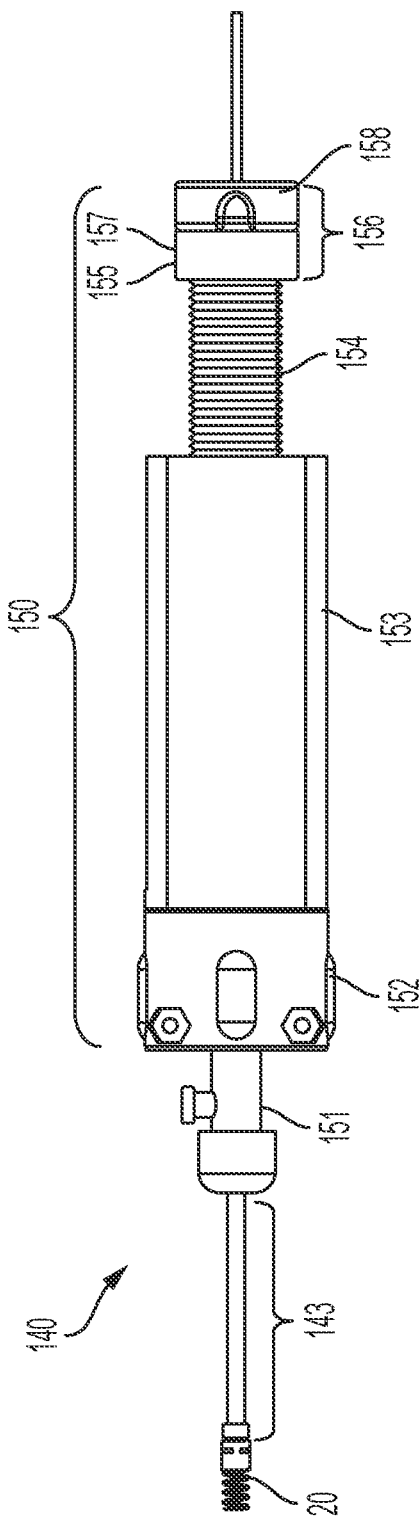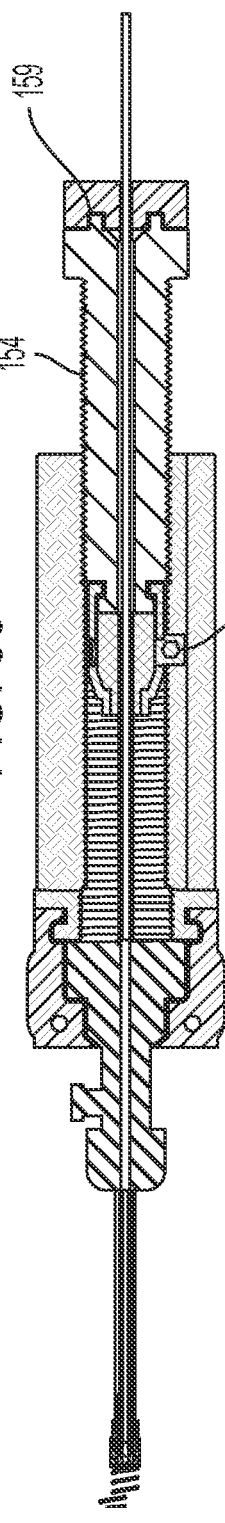

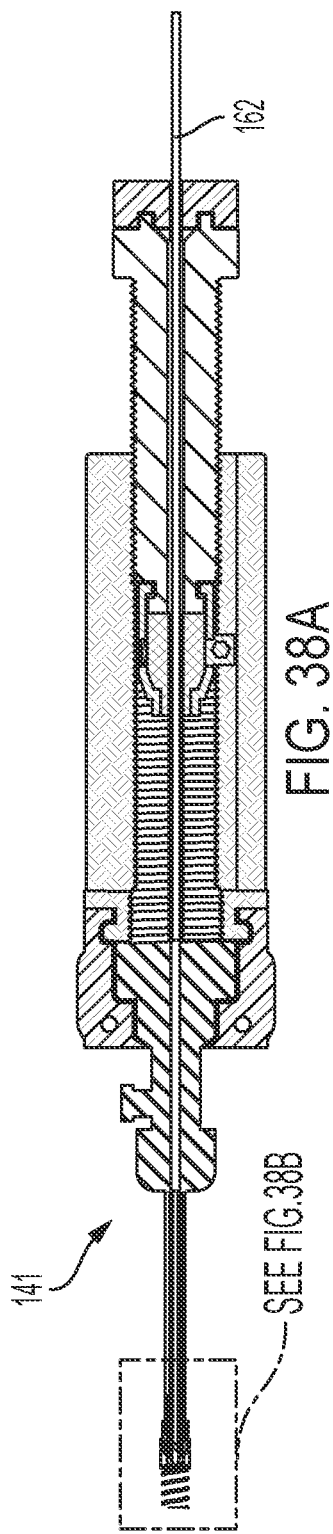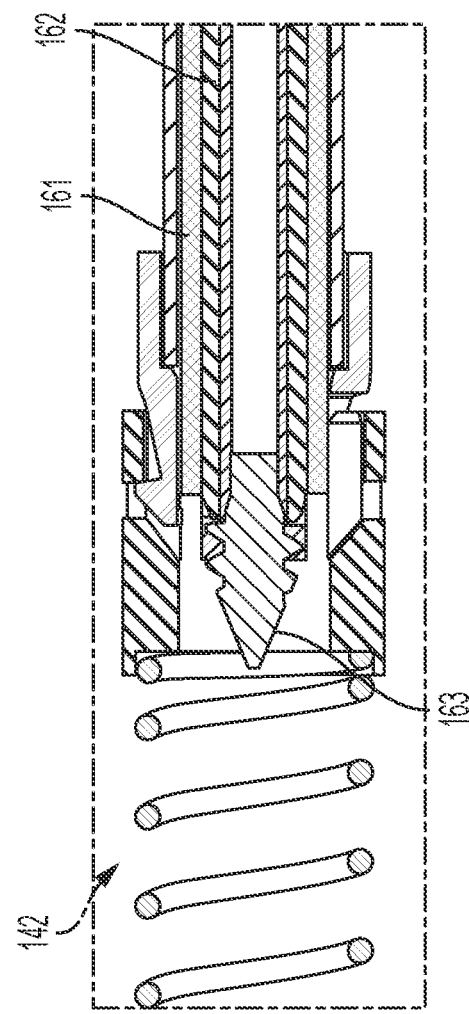

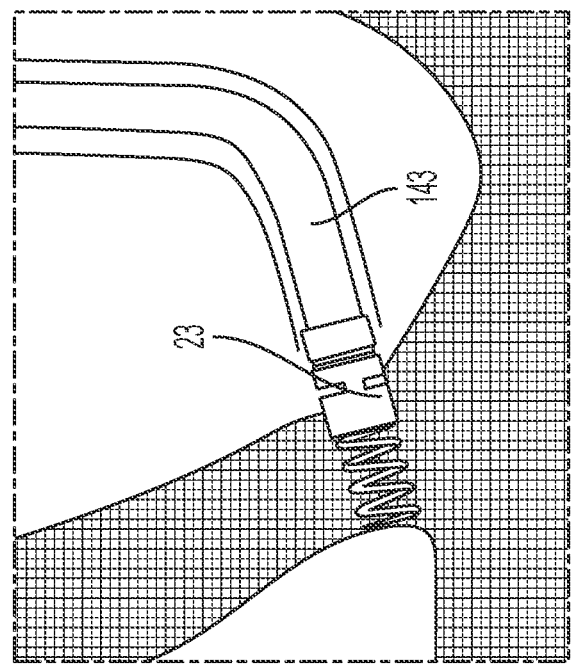
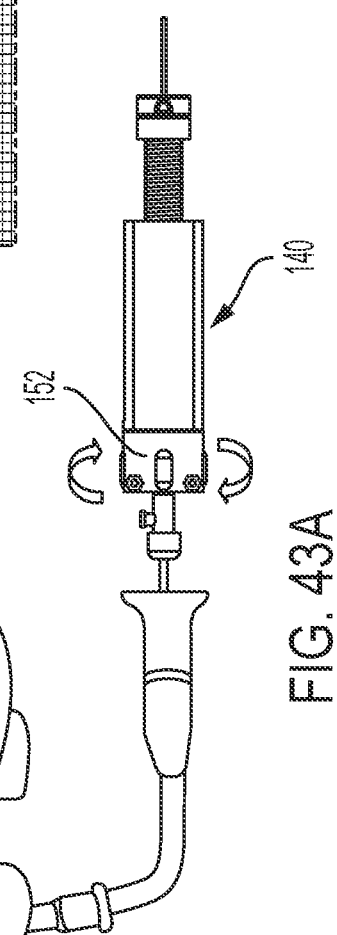
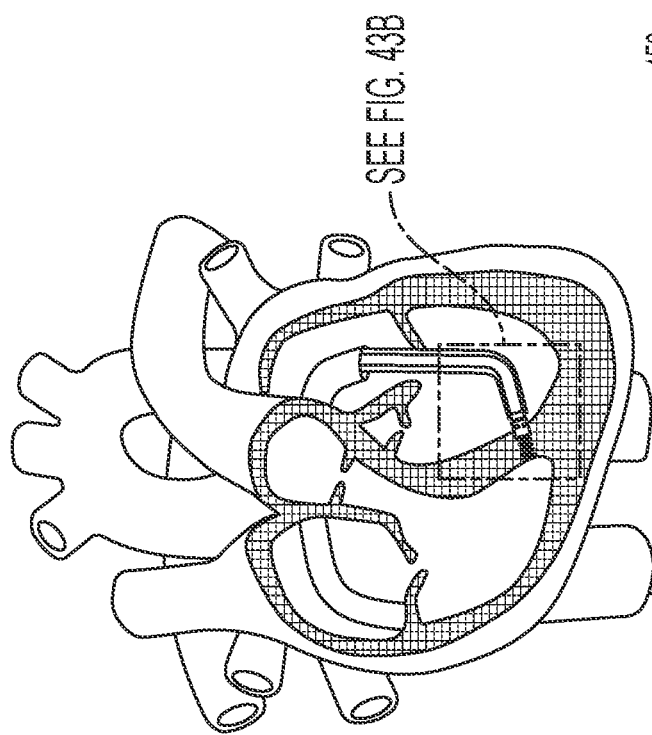
FIG. 43A
FIG. 43B

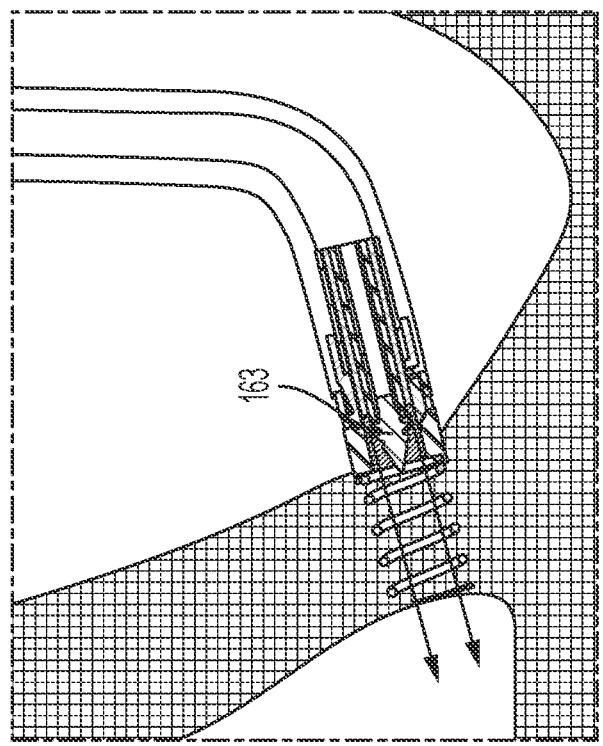
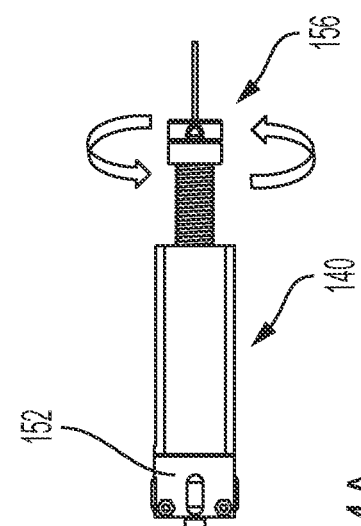
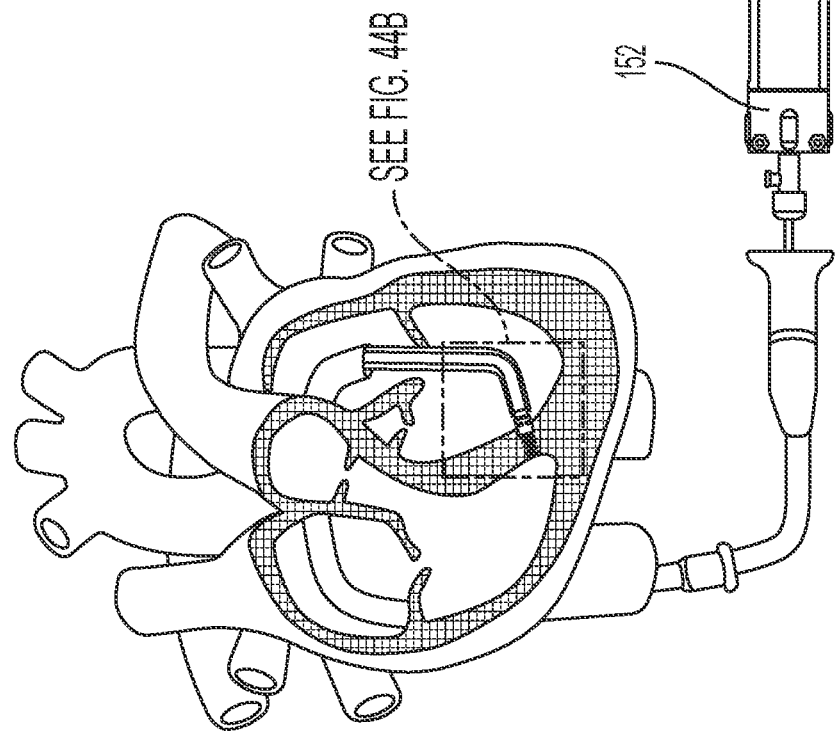
FIG. 44A
FIG. 44B

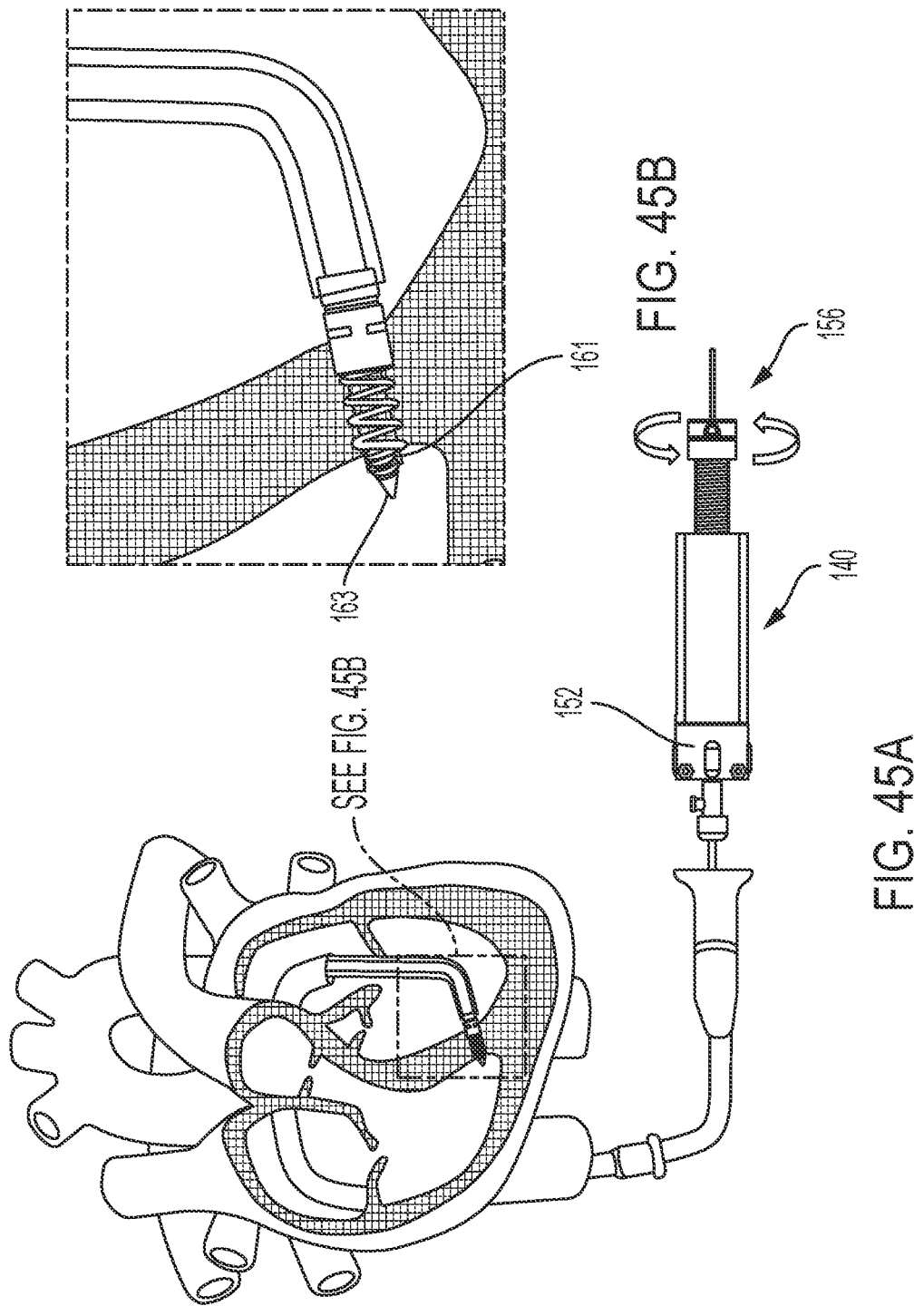

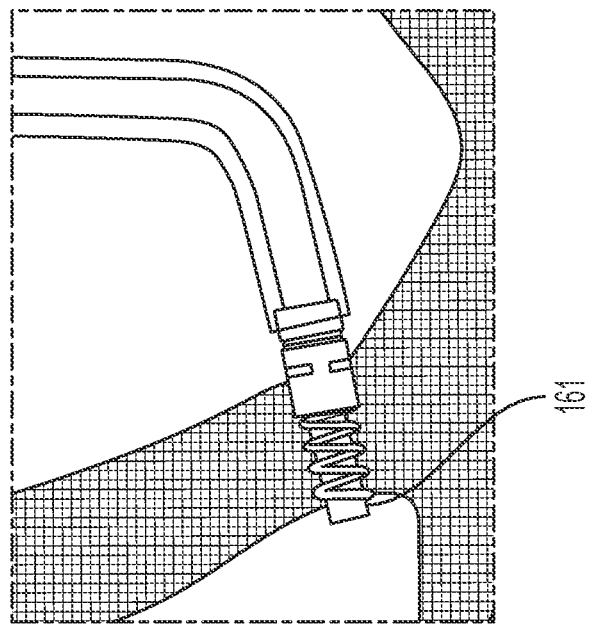
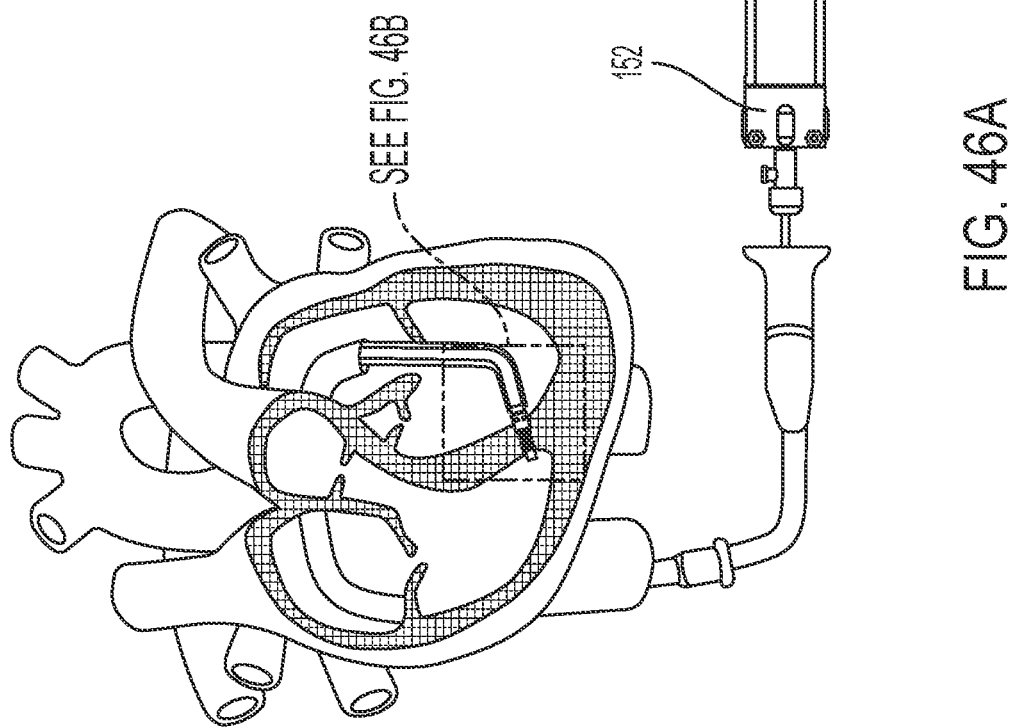
FIG. 46A
FIG. 46B

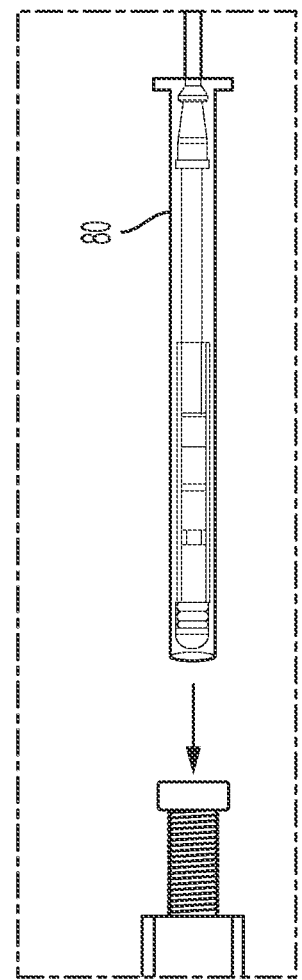
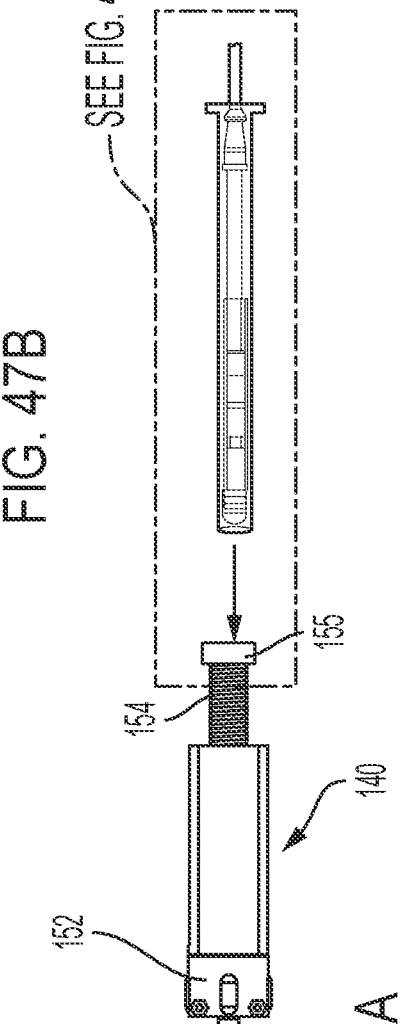
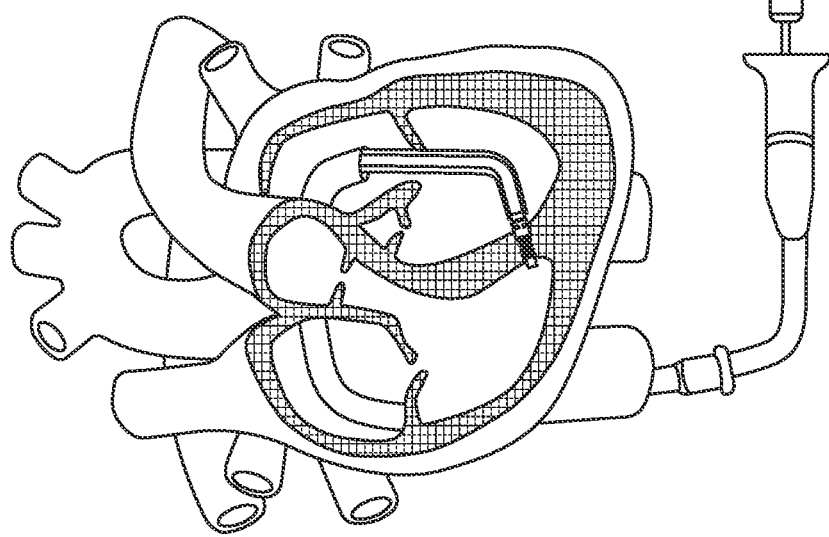
FIG. 47B
FIG. 47A

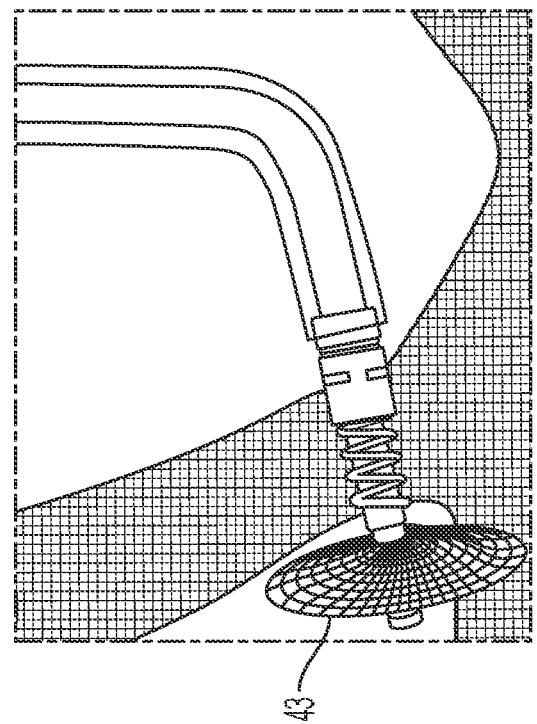
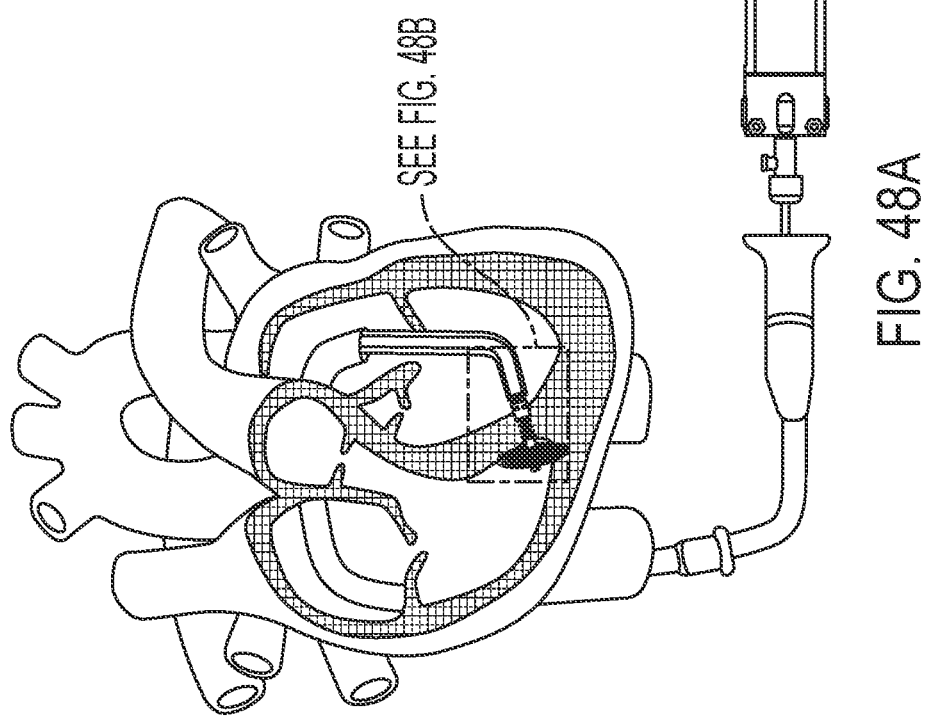
FIG. 48B
FIG. 48A

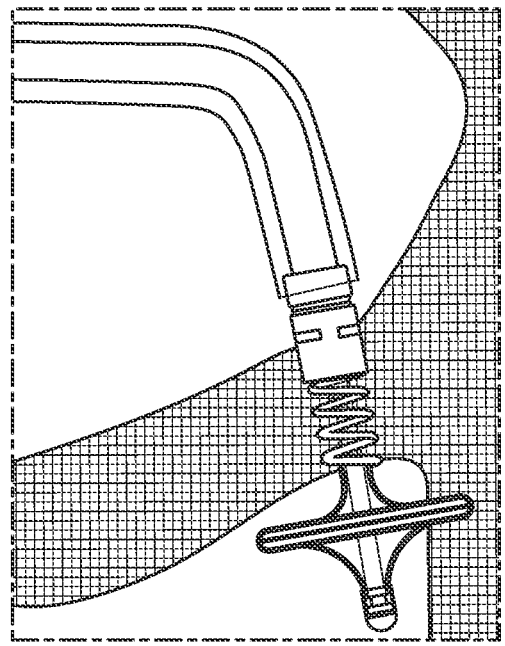
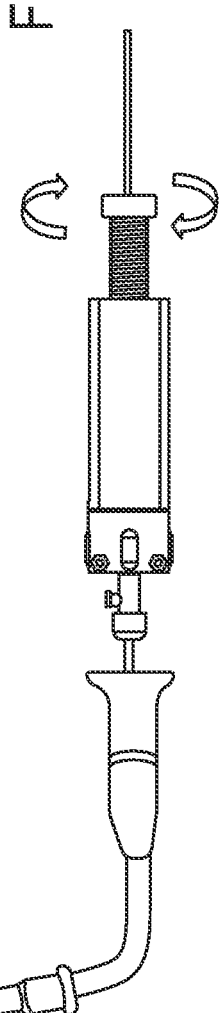
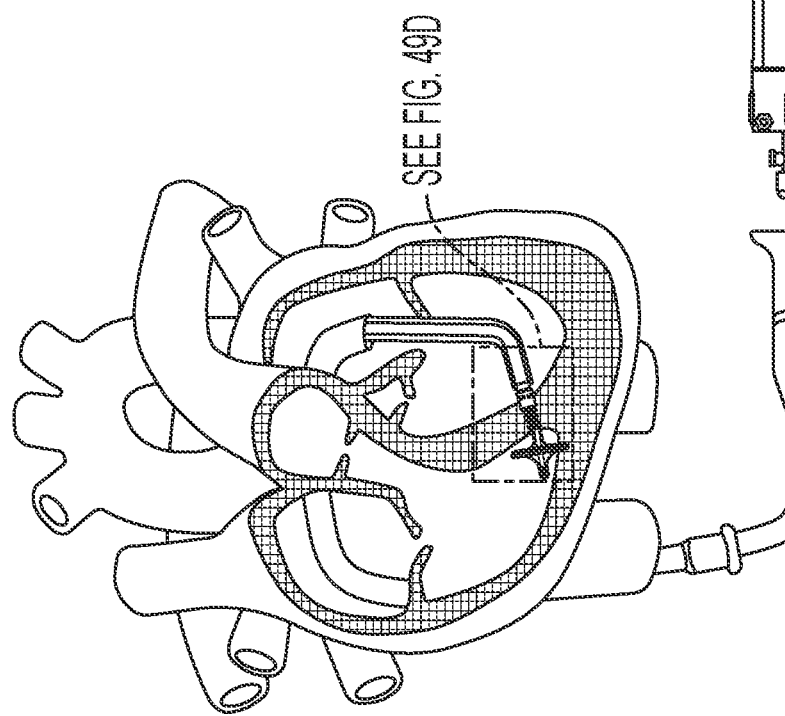
FIG. 49C
FIG. 49D

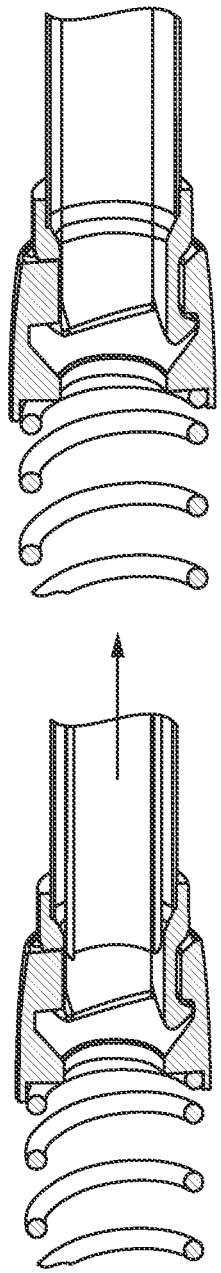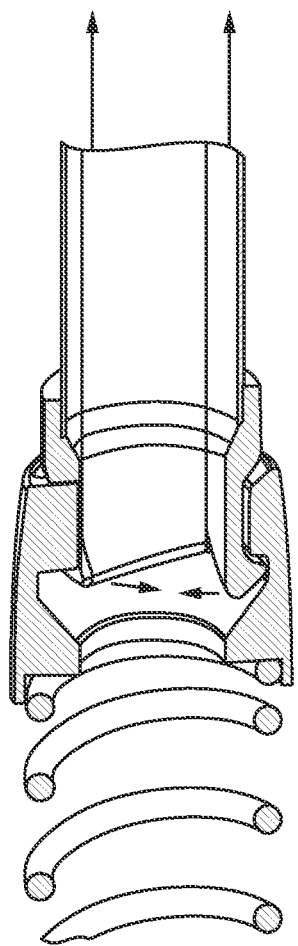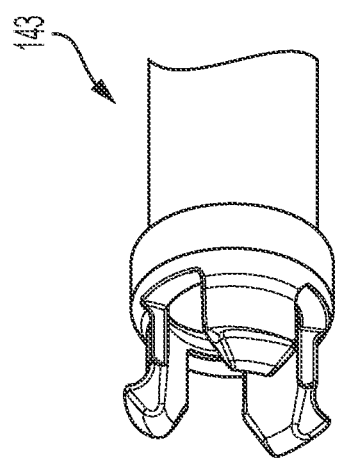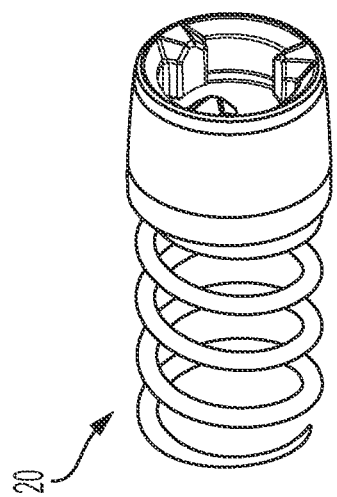
FIG. 50　　FIG. 51　　FIG. 52

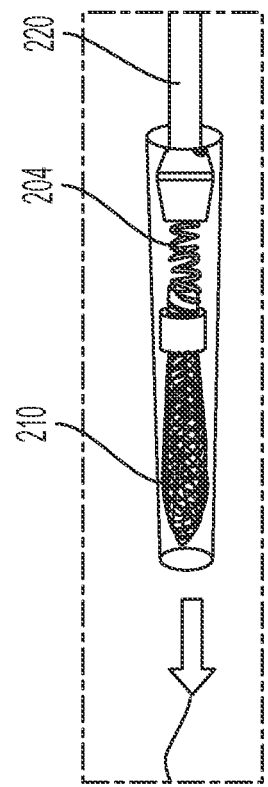
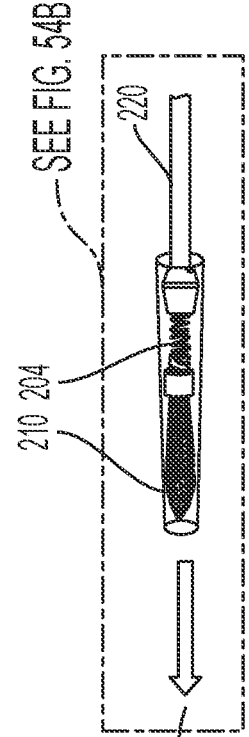
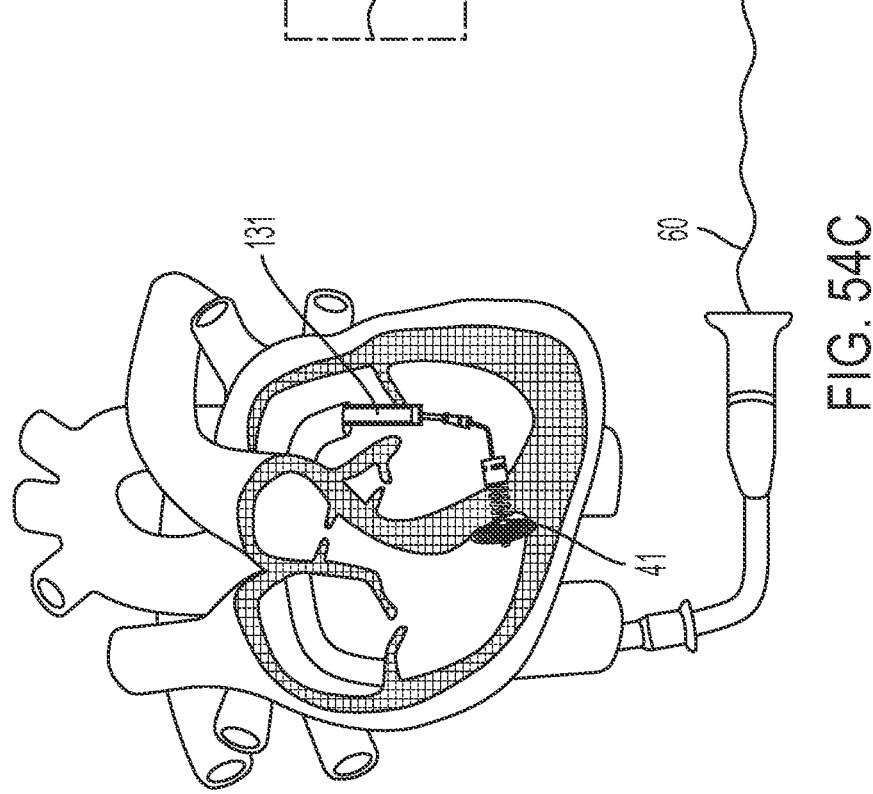

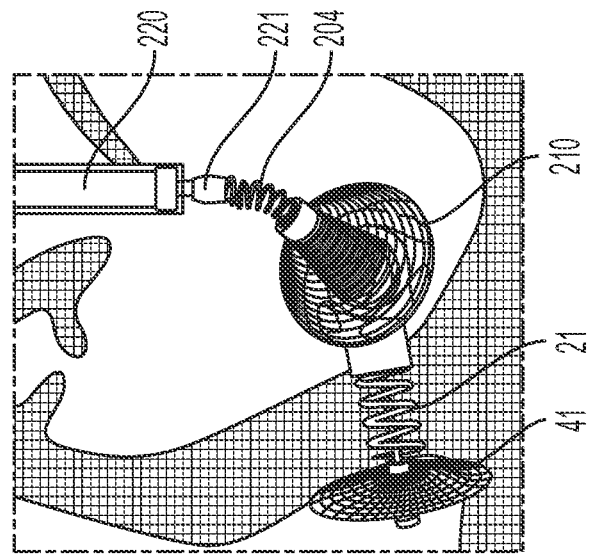
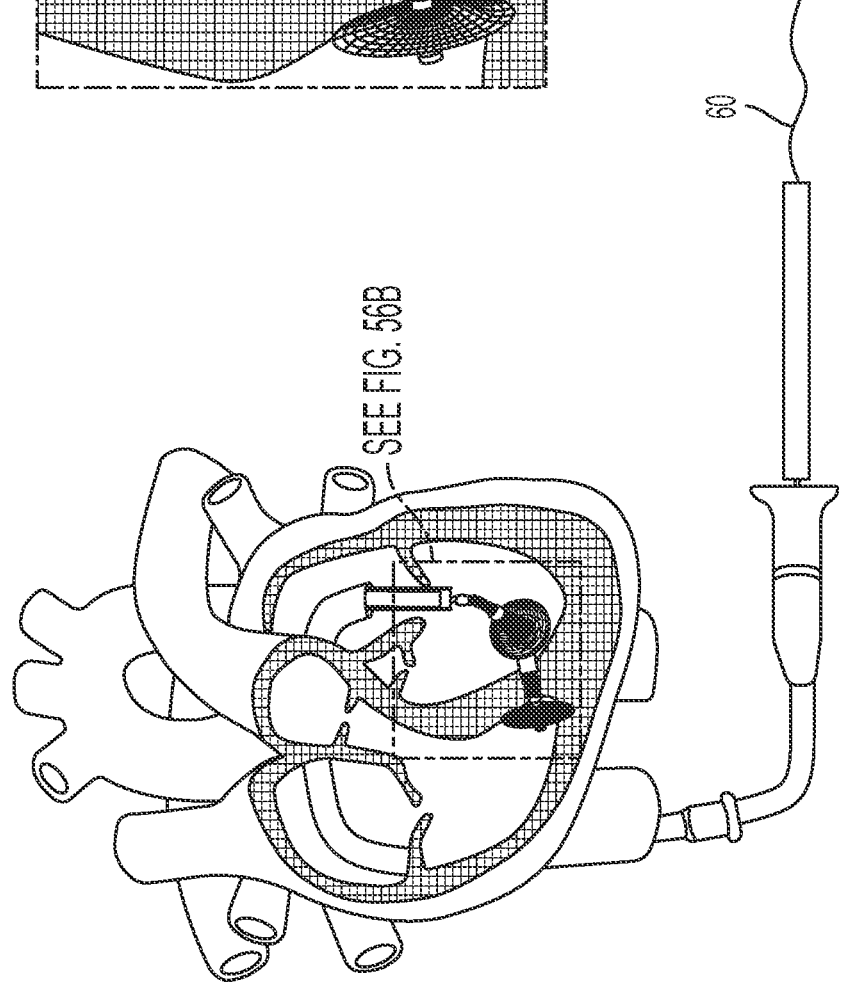
FIG. 56B
FIG. 56A

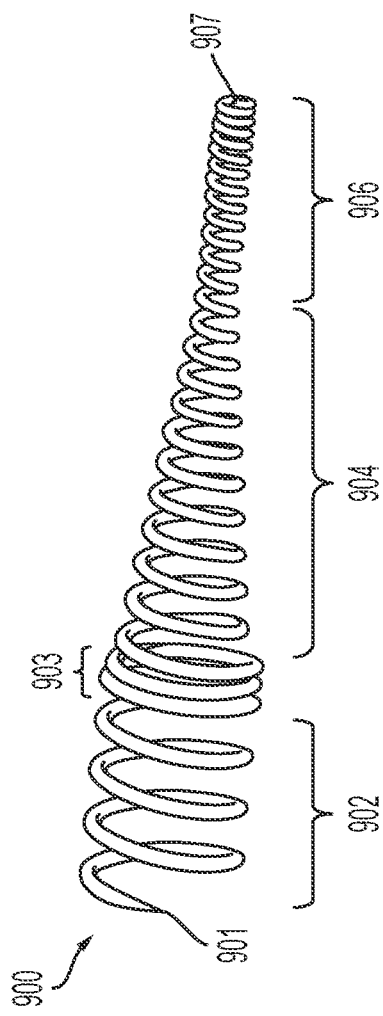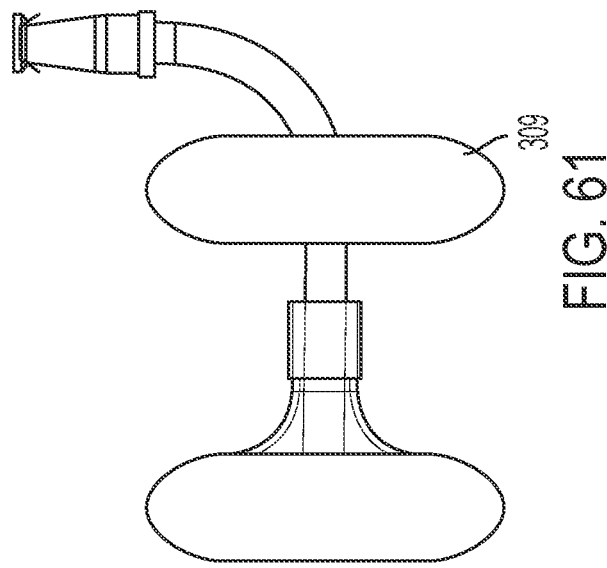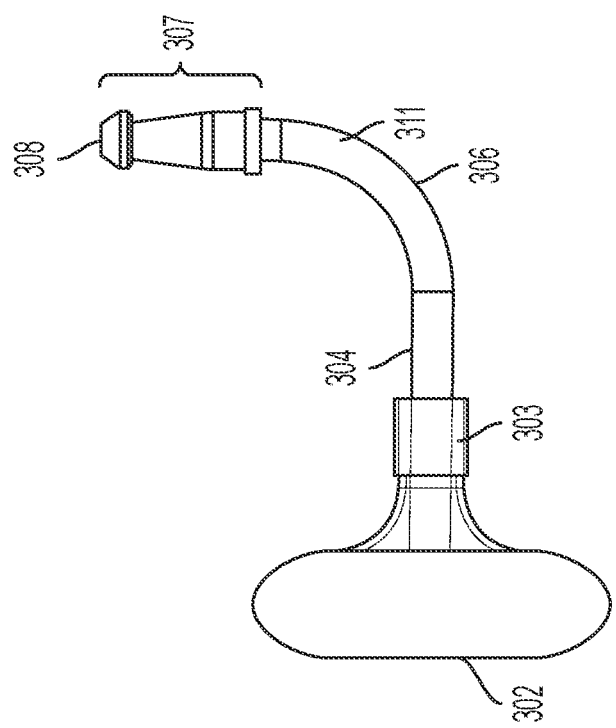

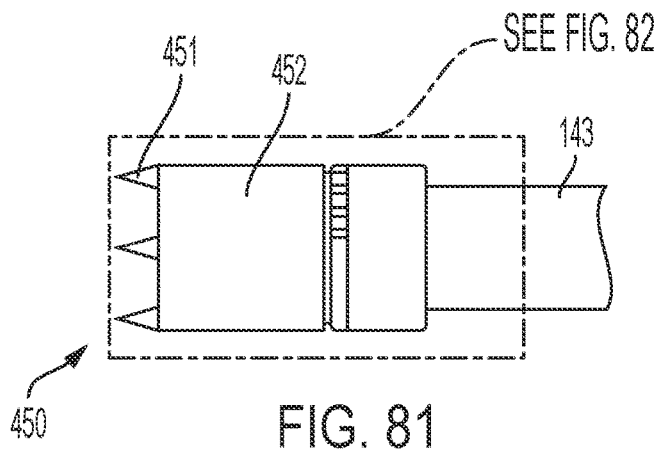
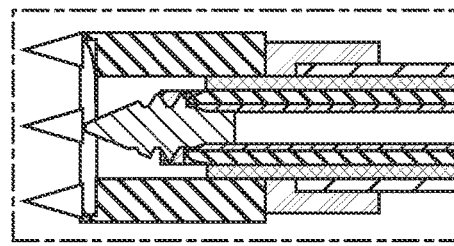
FIG. 81  FIG. 82
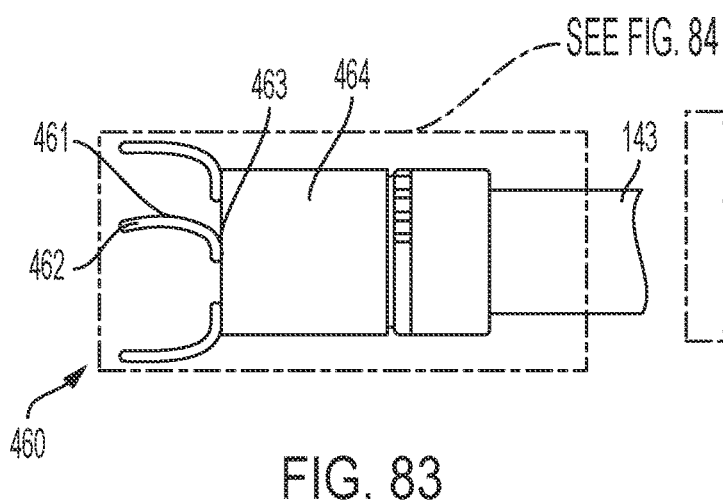
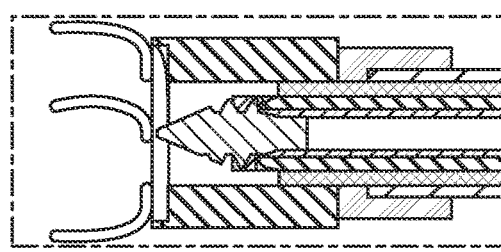
FIG. 83  FIG. 84
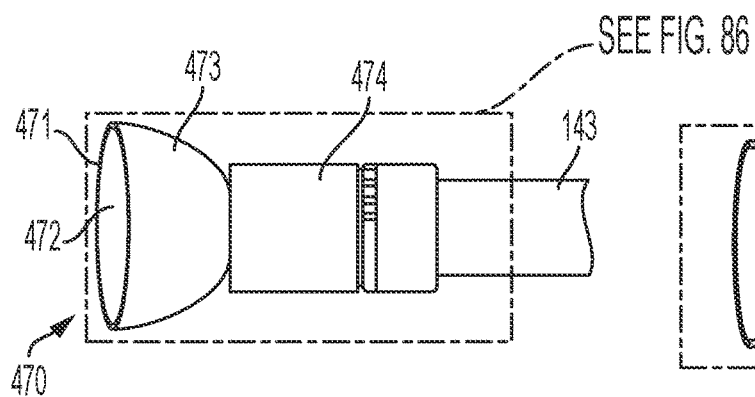
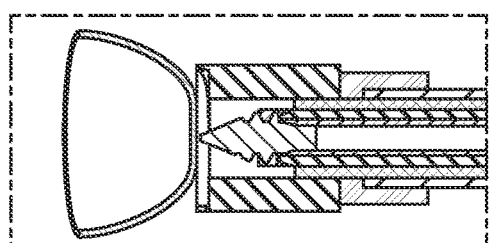
FIG. 85  FIG. 86

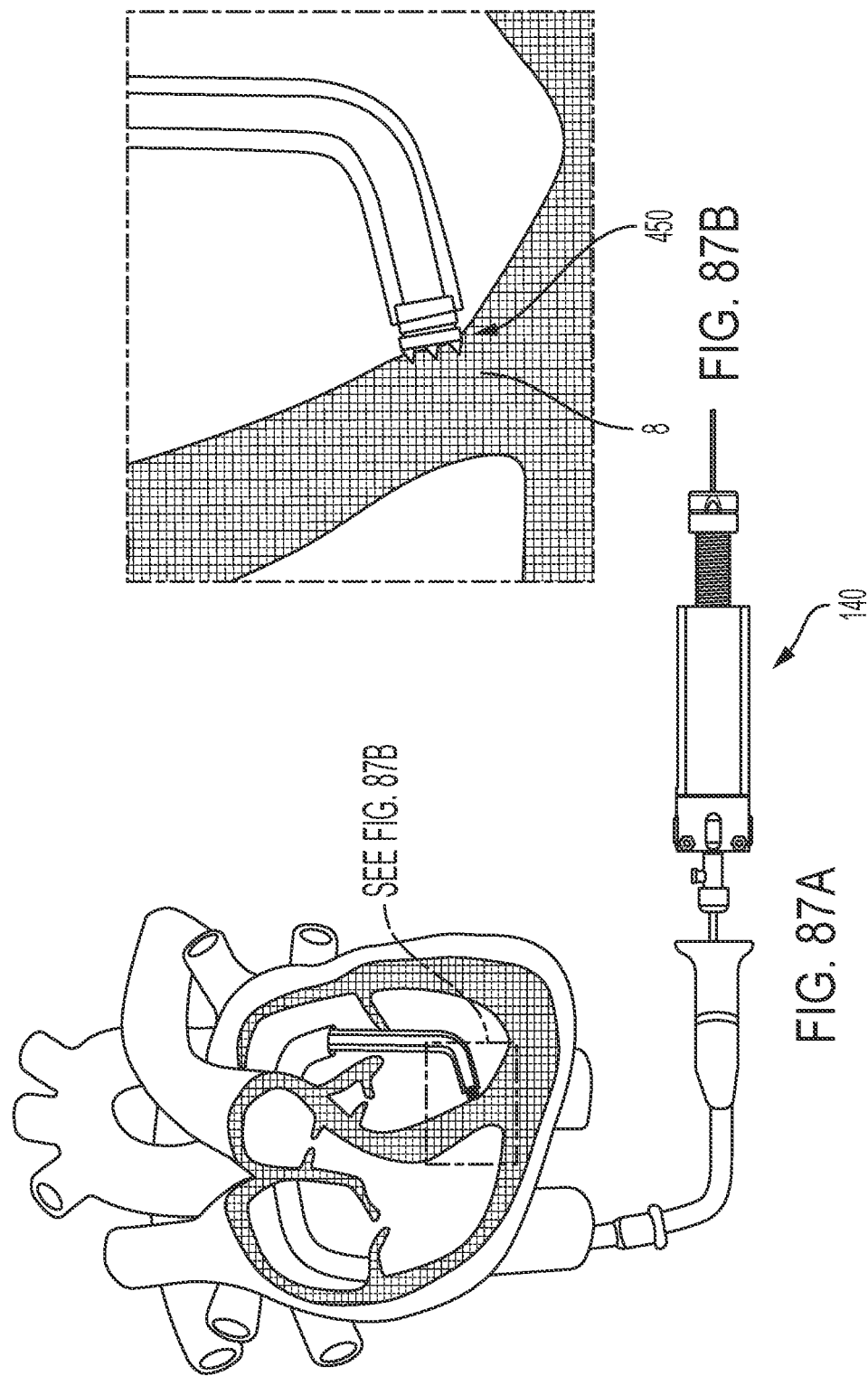

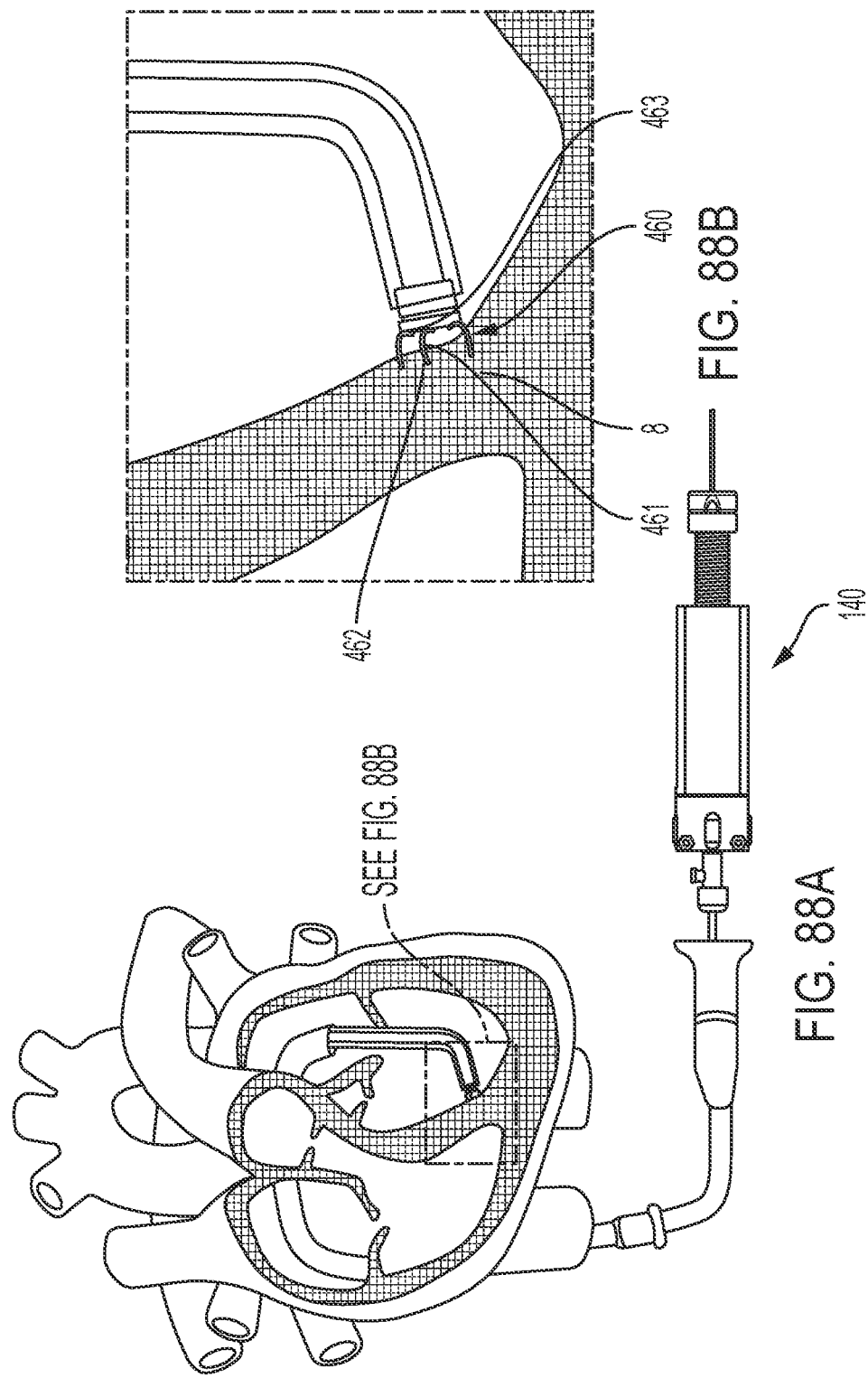

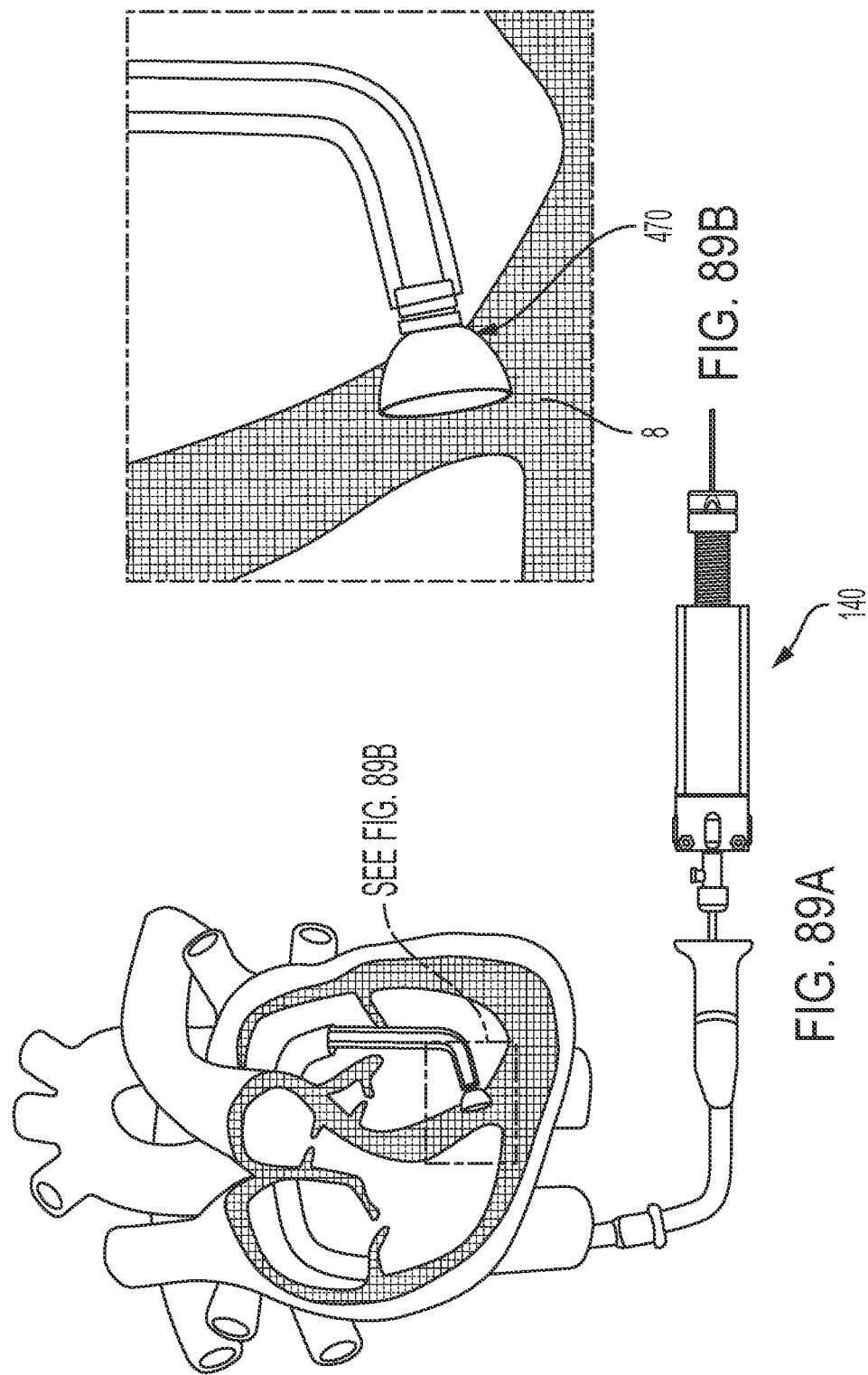

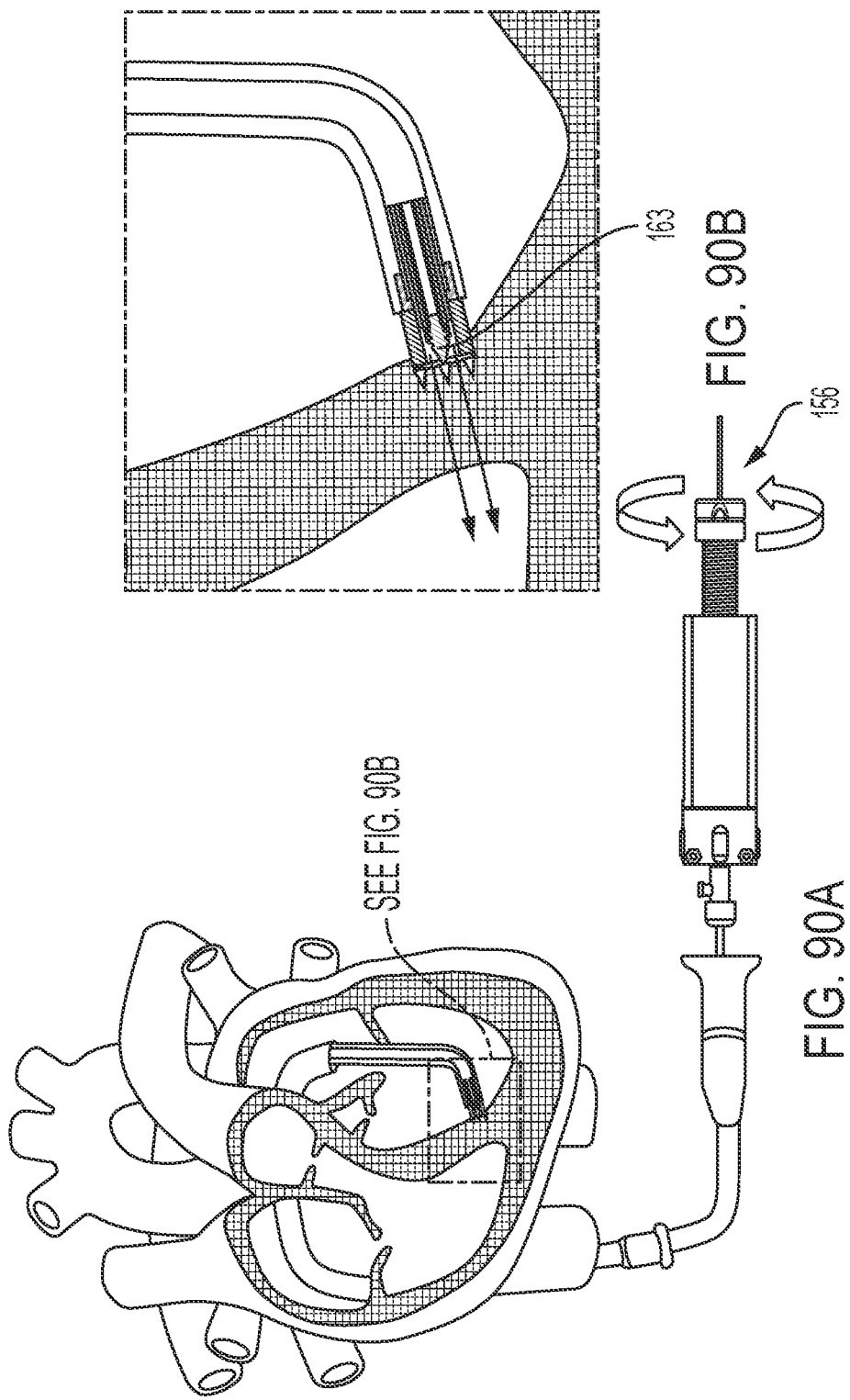

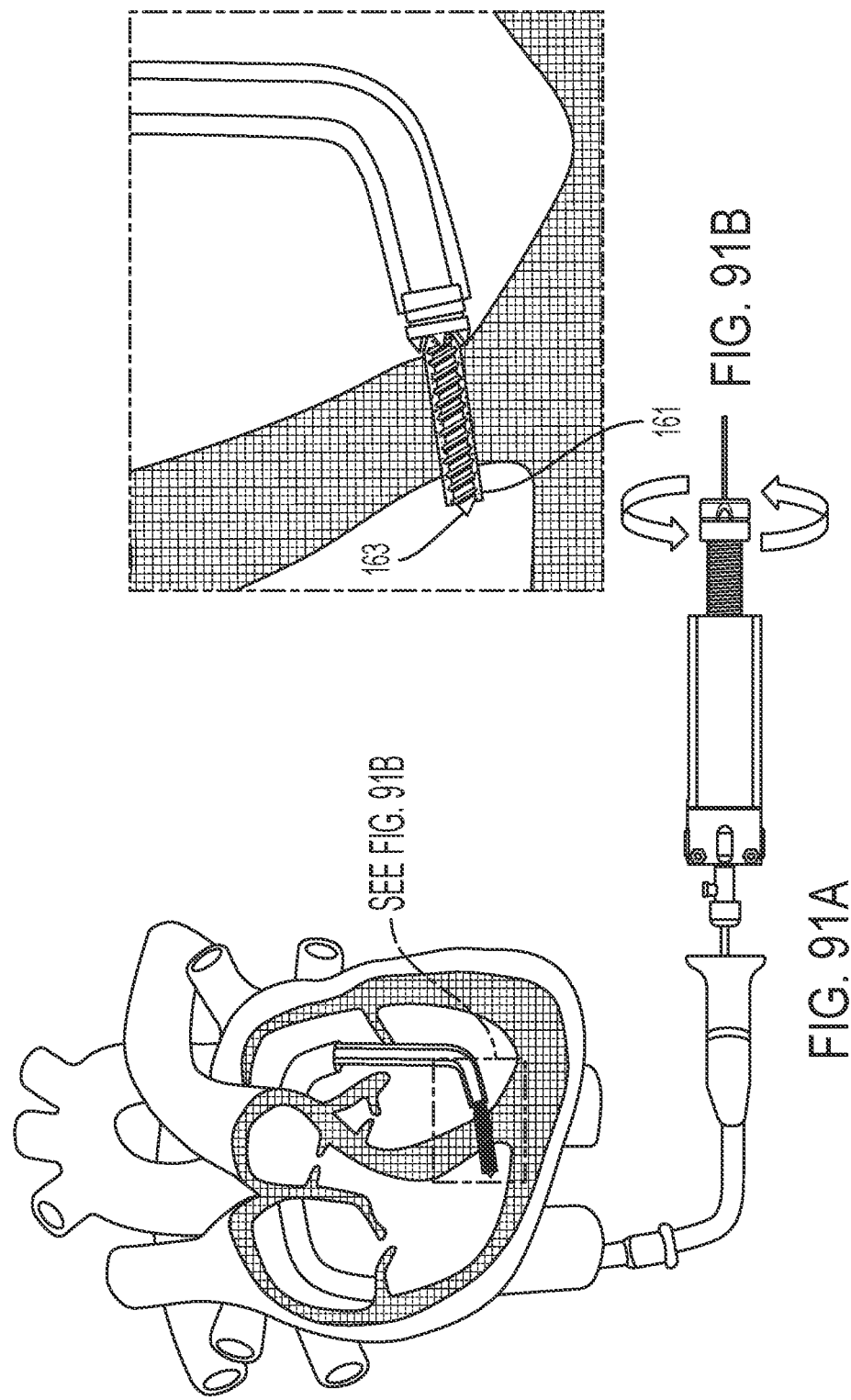

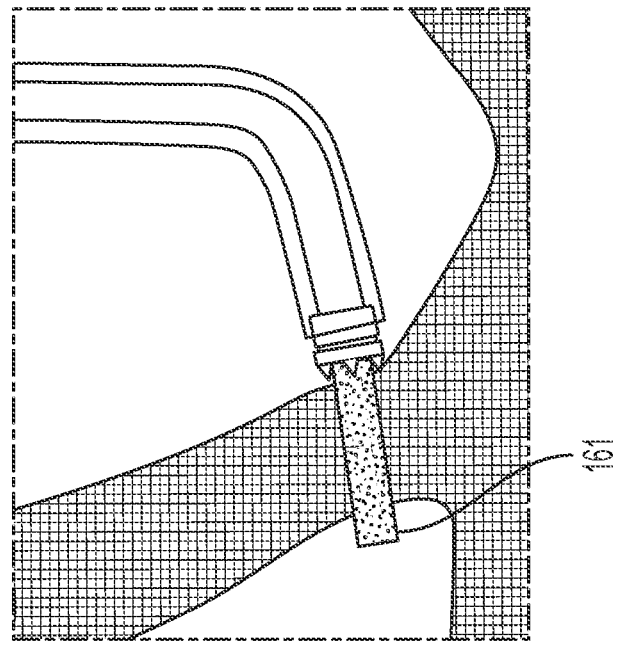
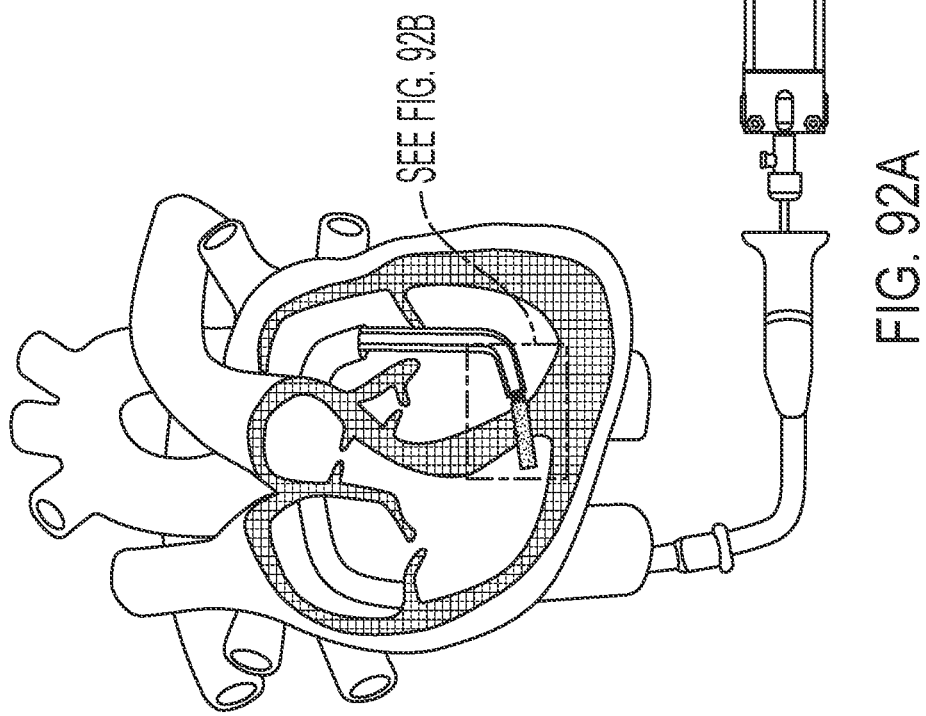
FIG. 92B
FIG. 92A

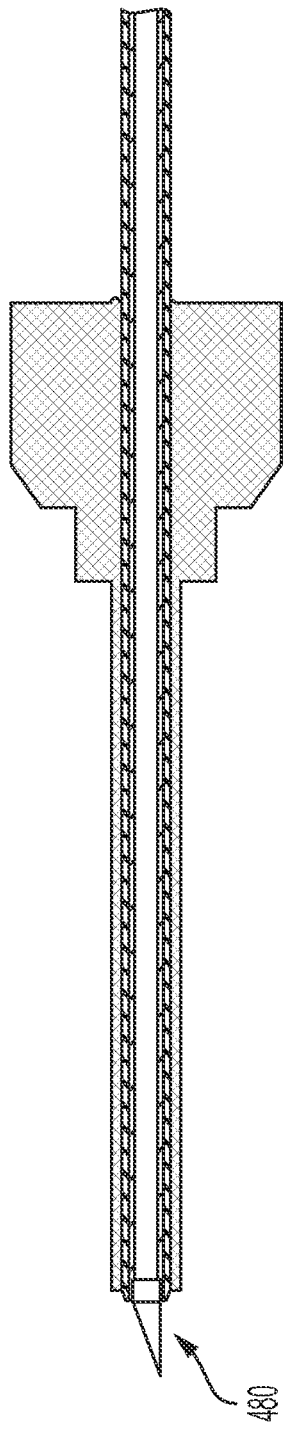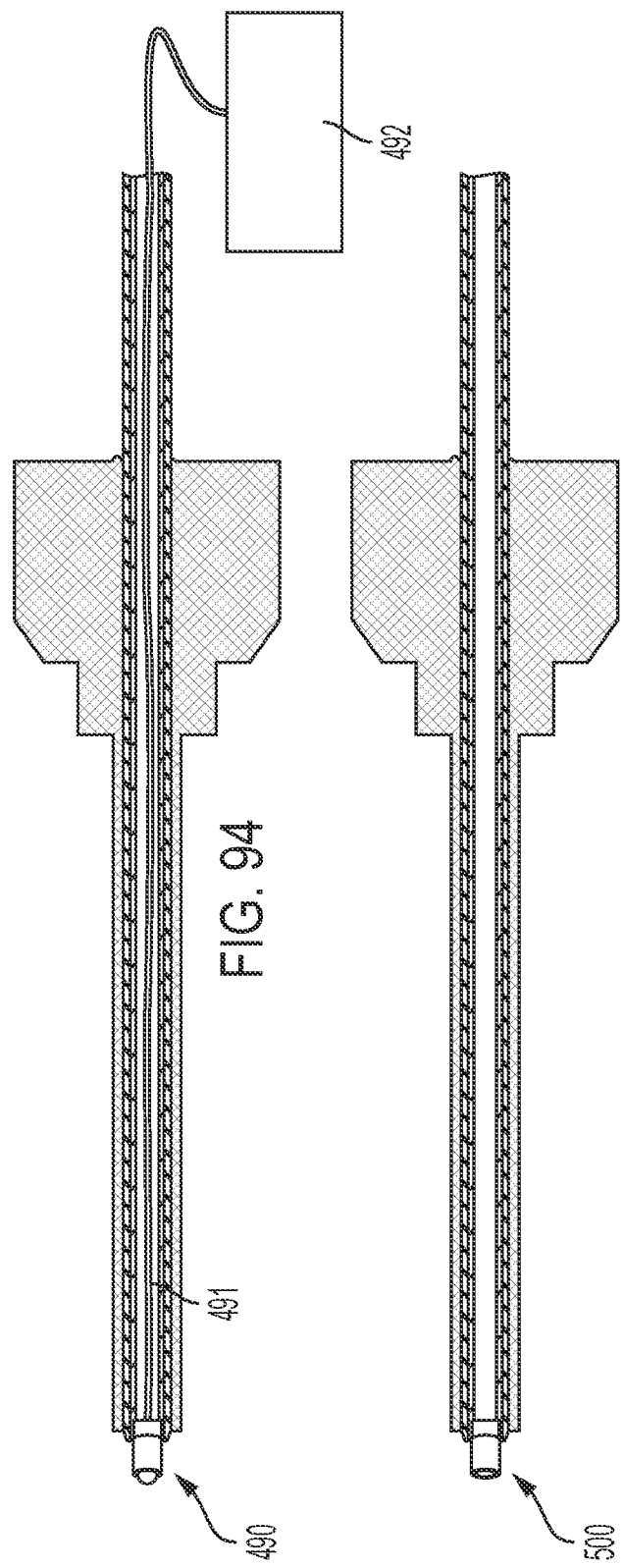
FIG. 93  FIG. 94  FIG. 95

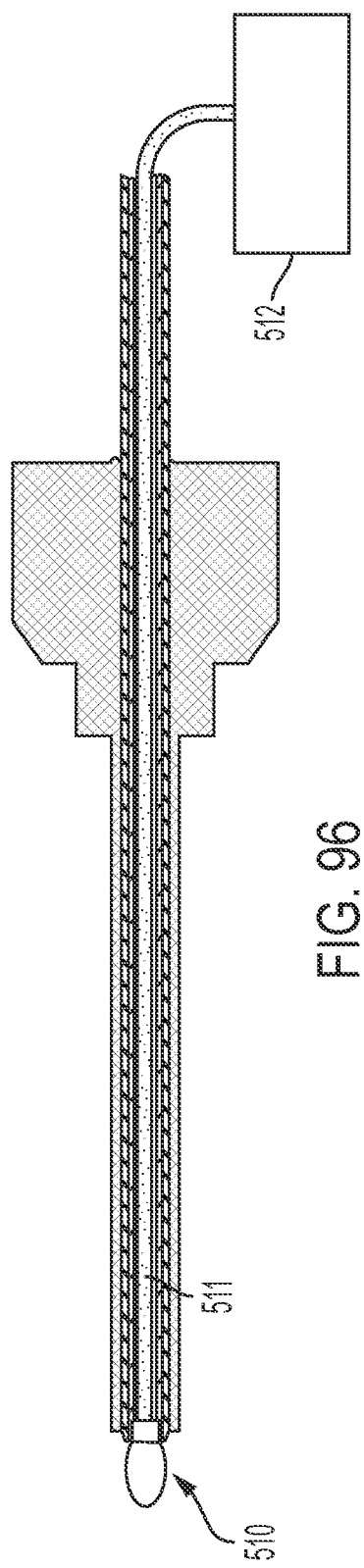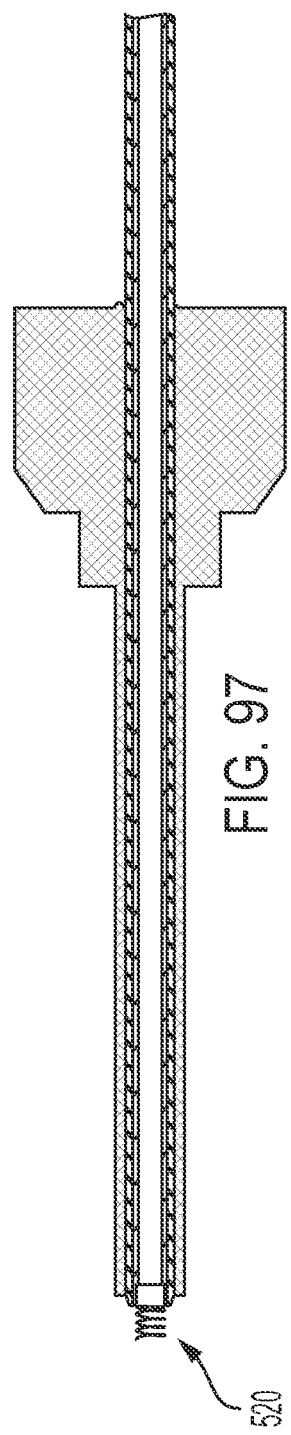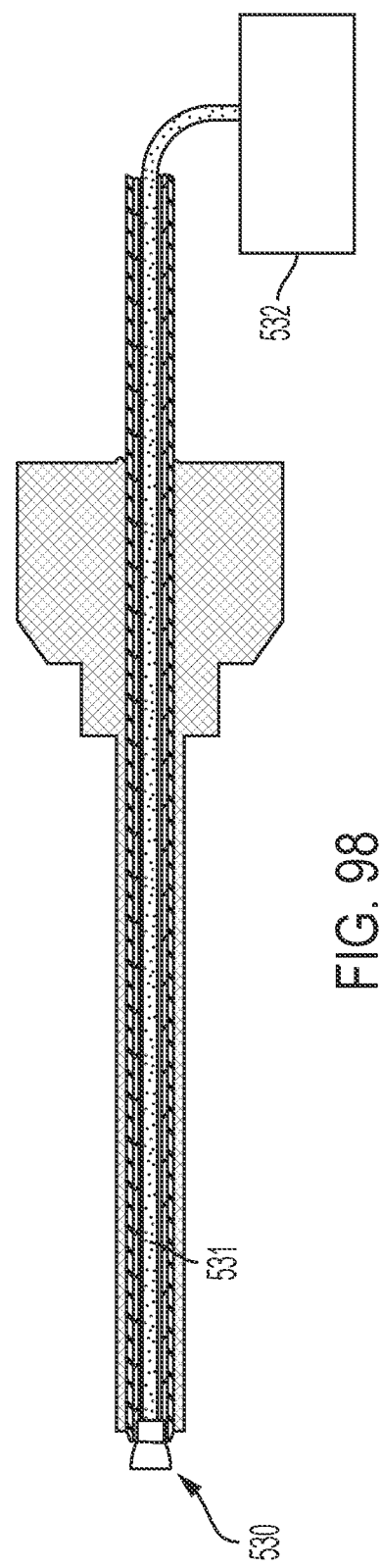

TRANSCATHETER ANCHOR SUPPORT, SYSTEMS AND METHODS OF IMPLANTATION

CROSS REFERENCE TO RELATED APPLICATIONS

This application claims the priority of U.S. App. Nos. 63/122,934 (filed Dec. 8, 2020), 63/058,763 (filed Jul. 30, 2020), 62/964,371 (filed Jan. 22, 2020) the disclosure of each are incorporated herein by reference.

FIELD OF INVENTION

The present invention relates generally to medical devices and systems for minimally invasively being implanted into the heart and methods of implantation of these devices and systems. More specifically, the invention pertains to medical devices and systems which are implanted minimally invasively into any wall of the heart, using one or more anchor supports.

SUMMARY OF INVENTION

Presented herein are medical devices and systems which are implanted minimally invasively into any wall of the heart, using one or more anchor supports. The valve anchoring system presented herein includes a single-stage anchor support or a two-stage anchor support, each consisting of a distal flange, and an anchor. The two-stage anchor support additionally includes a proximal flange. The anchor cooperates with an appropriate heart wall to implant the anchor support to the heart wall. The distal flange is introduced with a distal flange sheath through the anchoring member, such as the anchor coil, and through to the opposing side of the heart wall and expands within the cardiac space to secure the anchor support. Regarding the two-stage anchor support, a proximal flange delivery catheter delivers the proximal flange, to the proximal end of the distal flange and cooperates therewith to conform to the heart wall opposing the distal flange.

The anchor support including the anchor is configured to cooperate with an anchor support delivery cable, which can be used for delivery of a tether assembly; this system may connect to any type of intracardiac prosthesis including, but not limited to, a transcatheter valve replacement (complete of hemi-valve replacement), valve repair system (chordal replacement, coaptation element, leaflet augmentation device, or annuloplasty ring), myocardial remodeling device, or ventricular assist device, securely anchoring any of these devices to a respective intracardiac wall. In one aspect, the anchoring system is delivered completely endovascularly, using a support delivery system, without the need for chest or cardiac incisions.

With regard to the two-stage anchor support, the distance between the distal and proximal flanges is not fixed and is variable depending on the heart wall thickness or application. Additionally, the physical properties of the distal and proximal flanges may selectively differ. The flexible compression element of the proximal flange allows it to be positioned securely at a variable distance from the distal flange depending on the thickness of the intracardiac wall. Additionally, as the flex connector of the distal flange is pulled in tension by the tethering system, the flexible compression element pushes the proximal flange away from flex connector base towards the intracardiac tissue. This system of forces increases mechanical stability of the anchor support and replicates the effect of a cantilevered beam, enabling redirection of the tensile force as displaced from the intracardiac wall anchoring site.

The system including the anchor support comprises a trans-septal guide catheter, anchor delivery guide, and an anchor support delivery system. The anchor support delivery system comprises an anchor, anchor torque driver, microcatheter with screw tip dilator, support delivery control handle, and anchor support.

According to the single-stage anchor support, the anchor support is composed of a distal flange and according to the two-stage anchor support, the anchor support is composed of a distal and proximal flange. According to both aspects, the distal flange may take various geometric forms, including, but not limited to, a generally disc-like form or a three-dimensional form. The distal flange includes an anchor restraint (shown as a disk and other configurations), support rod, flex connector (in the form of a wire or flexible coil), and flex connector base. In the single-stage anchor support, the distal flange connects, via the support rod, to the flex connector, which connects to the flex connector cap, which serves as a docking element for the tether assembly. The two-stage anchor support incorporates all the elements of the distal flange, but also has a proximal flange, which is composed of an anchor restraint (for example, disk) flexible compression element, and docking element to secure the proximal portion of the flexible compression element to the flex connector of the distal flange, just under the flex connector cap The distal flange has a cap at its terminal end, and the cap may take the shape of a portion of a sphere or of any polyhedron. Each face of the disk comprises a variable thickness or diameter, and may be shaped like a circle, ellipse, any polygon. In either the one or two-stage anchor support, attached to the distal flange is a rod, which can be of variable thickness and length, taking the shape of a circular or elliptical cylinder, or taking the shape of a prism with any polygonal cross-sectional shape. The distal flange selectively includes additional metal or plastic fixation elements that lock the position of the anchor support relative to the anchor. The proximal end of the rod connects to the flex connector.

The flex connector is selectively composed of any metal alloy such as a flexible nitinol wire or a variably pitched nitinol spring with variable thickness and length has variable flexibility along its length. The flex connector optionally is also covered by any biological or synthetic membrane as described above. The flex connector base is composed of a preselected material including any metal alloy and be of any shape. Further, the proximal end of the tether cap may define an internal "female" thread, which can accept "male" threads of a distal end of an anchor support delivery cable, although other means of attaching the anchor support delivery cable to the flex connector base are not excluded. Finally, the flex connector base can serve as a docking member for a tether assembly to connect the tether swivel to an intracardiac prosthesis such as a valve replacement.

The proximal flange is distal to the flex connector base and extends around the flex connector and the connector rod of the distal flange. The proximal flange has a restraint, abutting the anchor base of the anchor and around the proximal portion of support rod and distal portion of the flex connector of the distal flange, has a restraint face that may be of variable thickness or diameter, and may be shaped like a circle, ellipse, or any polygon. Also, the proximal flange restraint may take the same or different shape and may bend in a concave or convex fashion towards the intracardiac wall. The proximal flange restraint has a central lumen of any shape or diameter such that the it can be advanced over the flex connector and support rod. Extending from this lumen on the proximal side of the proximal flange restraint is a flexible compression element, which may be a helical coil or conical coil of any thickness, radius, pitch, helix angle, or cone angle. Alternatively, the flexible compression element may take the shape of any spring with an alternative cross-sectional shape, such as a square, rectangle, or any polygon, or take the form of any compression element designed to handle an axial load. Attached to the proximal portion of the compression element is a docking element in the shape of a circular or elliptical cylinder or taking the shape of a prism with any polygonal cross-sectional shape. The docking element may have, anywhere along its length or radius, one or more extension members of any shape, and the element has a lumen of any diameter or shape that allows the element to go over the flex connecter base. Once the element has advanced over the flex connector base, either the shape of the element or extension members external or internal to the element's lumen prevent the element from moving proximal to the base of the flex connector base.

The anchor support or portions thereof may be formed of an appropriate material including any metal alloy, such as, but no limited to, nitinol, stainless steel, titanium, or cobalt chromium, and any portion of the anchor support is optionally covered with biological tissue, such as bovine, ovine, porcine, or equine pericardium, or synthetic membranes such as, but not limited to, polytetrafluoroethylene (PTFE) or polyethylene terephthalate (PET).

According to various aspects, the anchor comprises an anchor coil and an anchor base. The anchor coil may comprise any appropriate helical device, or the anchor coil may be an inclined plane wrapped around a nail-like head, or a type of Archimedes-type screw, and be "right-handed" or "left-handed". The anchor coil is composed of any appropriate material including a metal alloy, such as, but not limited to, nitinol, stainless steel, titanium, or cobalt-chromium, and is optionally covered by any biological or synthetic membranes as is possible for anchor support described above. To facilitate penetration of the tissue, the tip of the anchor coil has, according to one aspect, a different diameter or cross-sectional shape as the rest of the coil; for example, the tip is, but is not limited to, the shape of a barb, hook, prong, or the like.

According to various aspects, the tether assembly consists of a tether swivel, composed of any metal or metallic alloy, and tethers, composed of, but without limitation, expanded polytetrafluoroethylene (ePTFE), ultra-high molecular-weight polyethylene (UHNWPE or UHNW), nitinol wire, or any known surgical suture. The tether swivel further consists of a tether ring, one or more locking arms, with or without one or more tether arms. The locking arms and tether arms have a variable length and thickness and are spaced equally or at variable distances along the circumference of the tether ring. The tether arms have distal coupling members, in the shape of eyelets, but without limitation in shape, that attach to tethers.

In one aspect, prior to docking of the tether system, the anchor torque driver remains attached to the anchor coil during fixation of the anchor coil to the cardiac wall. Fixation occurs by rotation of the anchor coil knob of the anchor support delivery control handle, thereby rotating the torque driver, which rotates the anchor coil via engagement with the anchor base. In another aspect, after fixation of the anchor coil to the wall, rotation of the microcatheter delivery knob of the anchor support delivery control handle rotates the microcatheter with screw tip dilator, driving the screw tip dilator and associated microcatheter across the interventricular septum (or another cardiac wall). Once microcatheter has traversed the septum (or other cardiac wall), the screw tip dilator is removed. In a further aspect, the distal flange of either the single or two-stage anchor support is pushed by the support delivery cable through the microcatheter until the anchor restraint exits the end of the microcatheter and is deployed. After deployment, the microcatheter is removed, allowing the anchor torque driver to be disengaged from the anchor base of the anchor coil, which remains fixed into the cardiac wall.

In another aspect, the anchor support delivery cable is used as a guidewire for delivery of the proximal flange. Over the guidewire, the proximal flange delivery sheath, attached to the docking element of the proximal flange, pushes the proximal flange to the end of anchor delivery guide. Once the proximal flange exits the distal end of the anchor delivery guide, the proximal flange restraint expands, and is pushed by the proximal flange delivery sheath (attached to disk via the flex coil and docking element) until the proximal flange restraint abuts the intracardiac wall near the anchor base. Continued pushing of the proximal flange advances the docking element and flexible compression element over the flex connector until the docking element goes past the flex connector base, at which point the element cannot be retracted past the flex connector base. The proximal flange delivery sheath is disengaged from the docking element, leaving the proximal flange and anchor support delivery cable in place.

In another aspect, the anchor support delivery cable is used as a guidewire for the docking of the tether assembly onto the flex connector base of the flex connector. After docking of the tether assembly and associated intracardiac device, the anchor support delivery cable is unscrewed or otherwise disengaged from the flex connector base, thereby fully deploying anchor support system.

In another aspect, before deployment of distal flange according to one aspect of the invention, the anchor is retrieved and redeployed if an alternative anchoring site is desired. Specifically, the anchor torque driver is rotated in opposite direction, thereby turning the anchor base and attached anchor coil so that the anchor coil disengages from the tissue. After anchor and anchor support delivery, the anchor support is capable of being retrieved and redeployed if it is interfering with intracardiac structures such as papillary muscles, chordal or valvular apparatus. Alternatively, the anchor support may be removed, leaving the anchor in position, and another anchor and support may be deployed at an alternative site.

Presented herein are anchor supports for supporting medical devices and systems which are implanted minimally invasively into any wall of the heart, such as a heart valve to replace a native heart valve. The anchoring devices includes an anchor support, with or without an anchor, and a tether assembly. According to one aspect, the distal end of the anchor support cooperates with an anchor and the proximal end of the anchor support cooperates with a tether assembly. According to another aspect, the distal end of the anchor support connects to a cardiac wall directly and connects to the tether assembly. The anchor support thus connects to a tether assembly that connects to the intracardiac device or implant, such as a transcatheter valves, and securely anchors the to a respective intracardiac wall. In one aspect, the anchor support is delivered completely endovascularly, using a support delivery system, followed by delivery of the tether assembly without the need for chest or cardiac incisions. In one aspect, the system comprises a trans-septal guide catheter, anchor delivery sheath, and an anchor support delivery system. The anchor support delivery system comprises an anchor, anchor torque driver, microcatheter with screw tip dilator, support delivery control handle, and anchor support. In another aspect, the system comprises a trans-septal guide catheter, anchor delivery sheath, and anchor support delivery system without an anchor. In this aspect, instead of being secured to the wall with an anchor, the anchor delivery sheath is secured to the cardiac wall by protrusions, spikes, barbs, claws, microneedles, or suction mechanisms. In another aspect, the anchor support delivery system comprises a microcatheter that functions without a screw tip dilator, but with an alternative dilator. In this aspect, the microcatheter is coupled with either a radiofrequency tip dilator, helical coil tip dilator, needle tip dilator, rotating tip drill dilator, oscillating tip dilator, or laser tip dilator.

Related methods of operation are also provided. Other apparatuses, methods, systems, features, and advantages of the medical devices and systems that are implanted minimally invasively in the heart will be or become apparent to one with skill in the art upon examination of the following Figures and detailed description. It is intended that all such additional apparatuses, methods, systems, features, and advantages be included within this description, be within the scope of the medical devices and systems that are implanted minimally invasively in the heart and be protected by the accompanying claims.

BRIEF DESCRIPTION OF THE FIGURES

FIG. 7 is a cut-away perspective view of a heart showing a transcatheter left ventricular remodeling device with both cardiac wall implants secured to the interventricular septum and cardiac wall by the two-stage anchor support;

FIG. 8 is a side-elevational view of an anchoring member according to one aspect of the present invention;

FIG. 9 is a side-elevational view of an anchor torque driver;

FIG. 10 is a cross-sectional view of the anchor torque driver of FIG. 9;

FIG. 11 is a side-elevational view of the anchor attached to the anchor torque driver;

FIG. 12 is a cross-section view of FIG. 11;

FIG. 13A is a schematically represented, cross-sectional view of a microcatheter for piercing the heart wall and for inserting the distal flange;

FIG. 13B is a schematically represented view of the microcatheter of FIG. 13A and including a screw tip dilator within its lumen;

FIG. 17 is a schematic view of a distal flange loader for facilitating distal flange introduction;

FIG. 18 is a side elevational view, partially schematic, of the anchor support collapsed inside the support loader and connected to the support delivery cable;

FIG. 19A is a side elevational view of a distal flange having one configuration with support rod through the associated anchor and the wire flex connector extending from the support rod;

FIG. 19B is a side elevational view of the distal flange of FIG. 19A having another configuration;

FIG. 19C is a side elevational view of a distal flange having one configuration with support rod through the associated anchor and the coil flex connector extending from the support rod;

FIG. 20A is a perspective view of a distal flange with support rod through the associated anchor with the flex connector of distal flange attached to the support delivery cable;

FIG. 20B is a side elevational view of the distal flange with the wire flex connector and associated anchor with the delivery cable attached;

FIG. 20C is a side elevational view of the distal flange with the spring flex connector and associated anchor with the delivery cable attached;

FIG. 25 is a perspective view of a proximal flange delivery catheter connected to a proximal flange;

FIG. 26 is a side elevational view, partially schematic, of the proximal flange collapsed inside the proximal flange loader;

FIG. 27 is a perspective view of a proximal flange delivery catheter docking a proximal flange onto a distal flange;

FIG. 28 is a cross-sectional view of FIG. 27;

FIG. 29 is a perspective view of a distal flange coupled to a proximal flange of with the flex connector of the distal flange attached to the support delivery cable;

FIG. 30 is a perspective view of a distal flange coupled to a proximal flange with the flex connector of the distal flange attached to the support delivery cable;

FIG. 31 is a perspective view of a distal flange with support rod through the associated anchor, coupled to a proximal flange, with the flex connector of distal flange attached to the support delivery cable, demonstrating the restraints of the two flanges separated to accommodate an intracardiac wall;

FIG. 32 is a perspective view of FIG. 31 with the proximal flange more advanced toward the distal flange than in FIG. 31, demonstrating the restraints of the two flanges configured to accommodate a thinner intracardiac wall;

FIG. 33 is a perspective view of a distal flange with support rod through the associated anchor, coupled to the proximal flange, with the flex connector of the distal flange attached to the support delivery cable;

FIG. 34 is a perspective view of FIG. 33 with the proximal flange more advanced toward the distal flange than in FIG. 33, demonstrating the restraints of two flanges configured to accommodate a thinner intracardiac wall;

FIG. 35 is a schematic illustration of an anchor delivery guide according to the present invention;

FIG. 36 is a side-elevational view of the anchor support delivery system;

FIG. 37 is a cross-sectional view of the anchor support delivery system;

FIG. 38A is a cross-sectional view of the anchor support delivery system;

FIG. 38B is an enlarged, cross-sectional view of the distal end of the support delivery system of FIG. 38A, showing the anchor attached to the anchor torque driver and the microcatheter with screw tip dilator;

FIG. 43A is a cut-away perspective view of a heart with the anchor coil being screwed into the interventricular septum by the torque driver;

FIG. 43B is a magnified cut-away perspective view of a heart with the anchor coil being screwed into the interventricular septum by the torque driver;

FIG. 44A is a cut-away perspective view of a heart with the anchor coil screwed into the interventricular septum and microcatheter with screw dilator being advanced;

FIG. 44B is a magnified cut-away perspective of a heart with the anchor coil screwed into the interventricular septum and microcatheter with screw dilator being advanced;

FIG. 45A is a cut-away perspective view of a heart with the anchor coil screwed into the interventricular septum and the microcatheter screw dilator penetrating the septum;

FIG. 45B is a magnified cut-away perspective view of a heart with the anchor coil screwed into the interventricular septum and the microcatheter screw dilator penetrating the septum;

FIG. 46A is a cut-away perspective view of a heart with the anchor coil screwed into the interventricular septum and the microcatheter across the septum with the screw dilator removed;

FIG. 46B is a magnified cut-away perspective view of a heart with the anchor coil screwed into the interventricular septum and the microcatheter across the septum with the screw dilator removed;

FIG. 47A is a cut-away perspective view of a heart with a microcatheter across the interventricular septum and the distal flange of the two-stage anchor support being inserted into a microcatheter;

FIG. 47B is a magnified side-elevational view of the distal flange of the two-stage anchor support being inserted into the microcatheter;

FIG. 48A is a cut-away perspective view of a heart with the microcatheter across the interventricular septum and the anchor restraint of the distal flange of the two-stage anchor support deployed against the interventricular septum;

FIG. 48B is a magnified cut-away perspective view of a heart with the microcatheter across the interventricular septum and the anchor restraint of the distal flange of the two-stage anchor support deployed against the interventricular septum;

FIG. 49C is a cut-away perspective of a heart with the single-stage anchor support deployed and microcatheter being retracted;

FIG. 49D is a magnified cut-away perspective of a heart with the single stage anchor support deployed and microcatheter being retracted;

FIG. 50 is a magnified cut-away perspective of the anchor with microcatheter being retracted;

FIG. 51 is a magnified cut-away perspective of the anchor with microcatheter being retracted and end of torque driver bending inwards;

FIG. 52 is a perspective view of the torque driver being disengaged and retracted from the anchor;

FIG. 54C is a cut-away perspective view of a heart with a distal flange of the two-stage anchor support across the interventricular septum and a proximal flange being inserted into the anchor delivery guide;

FIG. 54D is a magnified side-elevational view of the proximal flange being inserted into the anchor delivery guide;

FIG. 56A is a cut-away perspective view of a heart with a proximal flange being advanced over the flex connector of the distal flange;

FIG. 56B is a magnified cut-away perspective view of a heart with a proximal flange being advanced over the flex connector of the distal flange;

FIG. 59 is a perspective view of a tapered anchor according to another aspect of the present invention;

FIG. 60 is a side elevational view of an anchor support with distal inflatable element;

FIG. 61 is a side elevational view of an anchor support with both distal and proximal inflatable elements;

FIG. 81 is a side elevational view of a fixation element with protrusions, attached to the anchor torque driver;

FIG. 82 is a cross sectional view of FIG. 81;

FIG. 83 is a side elevational view of a fixation element with extension members, attached to the anchor torque driver;

FIG. 84 is a cross sectional view of FIG. 83;

FIG. 85 is a side elevational view of a fixation element with suction cup, attached to the anchor torque driver;

FIG. 86 is a cross sectional view of FIG. 85;

FIG. 87A is a cut-away perspective view of a heart with the fixation element with protrusions of FIG. 81 positioned outside tip of the anchor delivery sheath next to the interventricular septum;

FIG. 87B is a magnified cut-away perspective view of a heart with the fixation element with protrusions of FIG. 81 positioned outside tip the anchor delivery sheath next to the interventricular septum;

FIG. 88A is a cut-away perspective view of a heart with the fixation element with extension members of FIG. 83 positioned outside tip of the anchor delivery sheath next to the interventricular septum;

FIG. 88B is a magnified cut-away perspective view of a heart with the fixation element with extension members of FIG. 81 positioned outside tip of the anchor delivery sheath next to the interventricular septum;

FIG. 89A is a cut-away perspective view of a heart with the fixation element with suction cup of FIG. 85 positioned outside tip of the anchor delivery sheath next to the interventricular septum;

FIG. 89B is a magnified cut-away perspective view of a heart with the fixation element with suction cup of FIG. 85 positioned outside tip of the anchor delivery sheath next to the interventricular septum;

FIG. 90A is a cut-away perspective of a heart with the fixation element secured to the interventricular septum and microcatheter with screw dilator being advanced; FIG. 90B is a magnified cut-away perspective of a heart with the fixation element secured to the interventricular septum and microcatheter with screw dilator being advanced;

FIG. 91A is a cut-away perspective view of a heart with the fixation element secured to the interventricular septum and the microcatheter screw dilator penetrating septum;

FIG. 91B is a magnified cut-away perspective view of a heart with the fixation element secured to the interventricular septum and the microcatheter screw dilator penetrating septum;

Figures 62, 63:
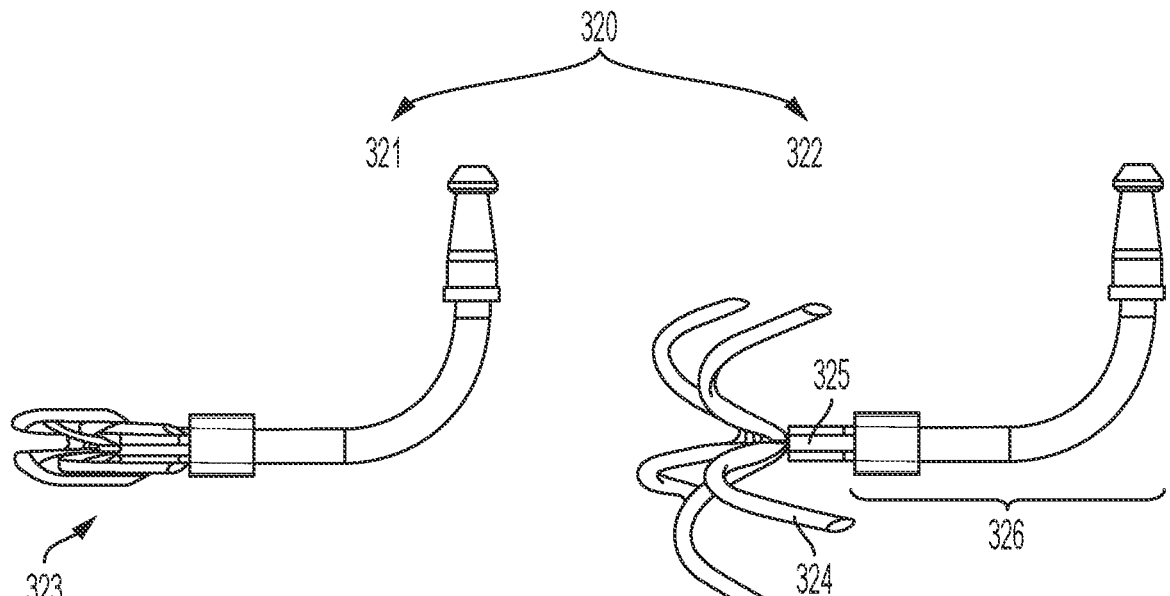
FIG. 62 is a side elevational view of an anchor support with radially extending elements with concave bend, in its undeployed form.
FIG. 63 is a side elevational view of an anchor support with radially extending elements with concave bend, in its deployed form.
Figures 64, 65:
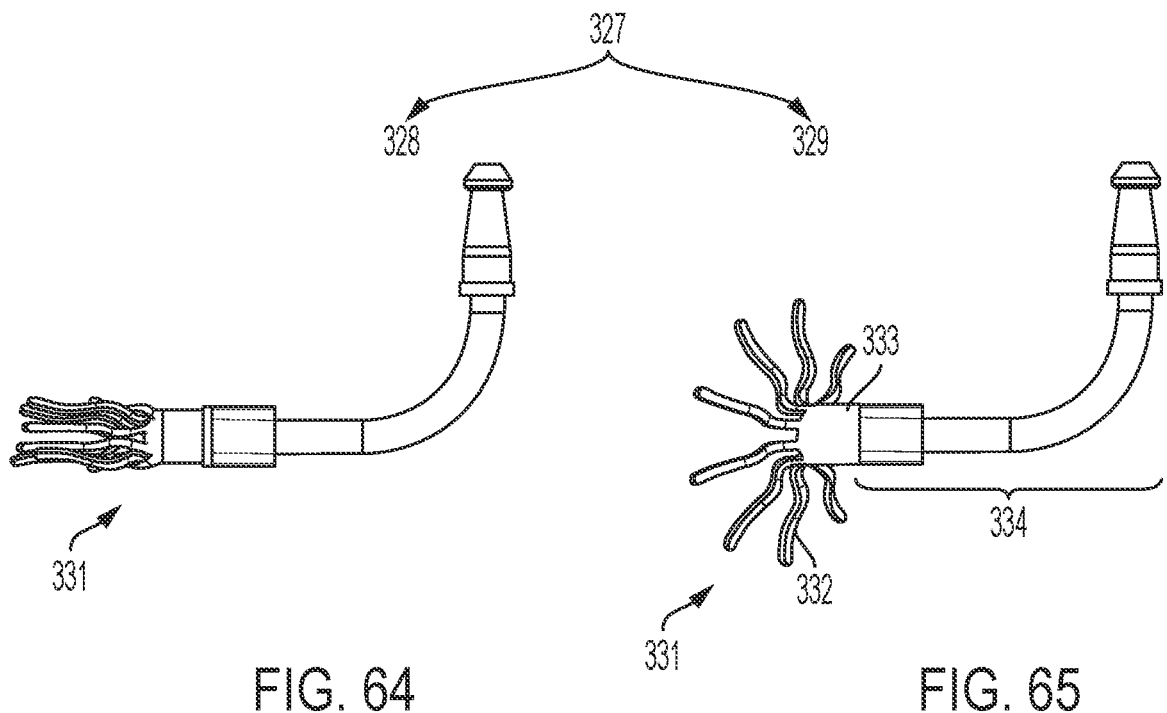
FIG. 64 is a side elevational view of an anchor support with radially extending elements with convex bend, in its undeployed form.
FIG. 65 is a side elevational view of an anchor support with radially extending elements with convex bend, in its deployed form.
Figures 66, 67:
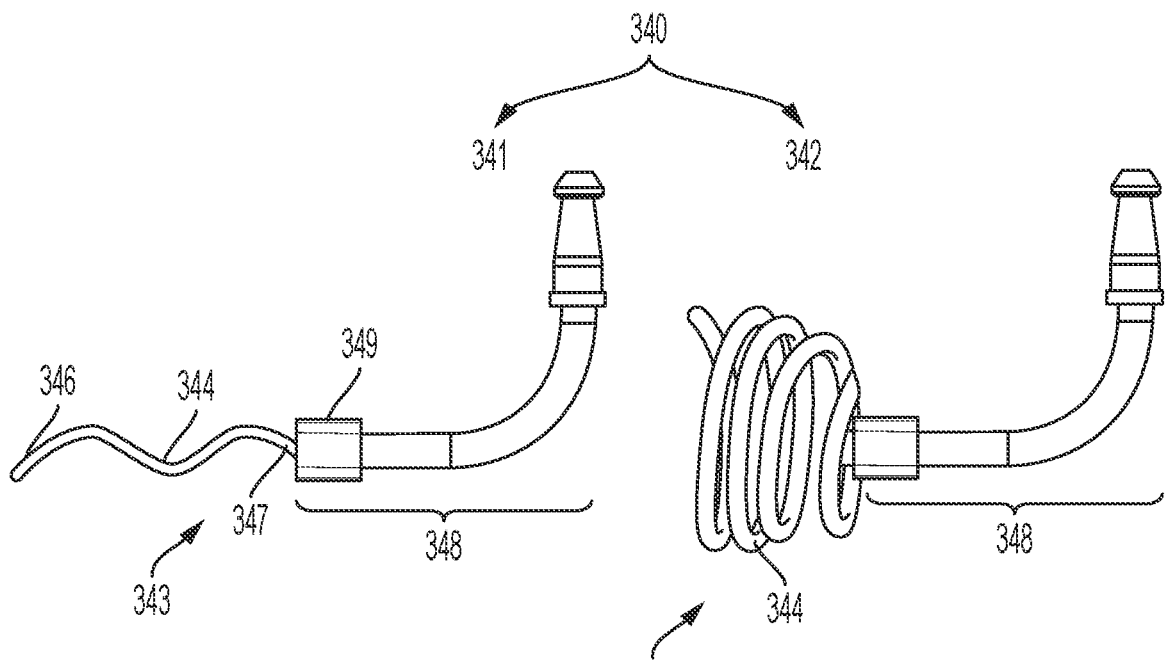
FIG. 66 is a side elevational view of an anchor support with a helical coil, in its undeployed form.
FIG. 67 is a side elevational view of an anchor support with a helical coil, in its deployed form.
Figures 70, 71:
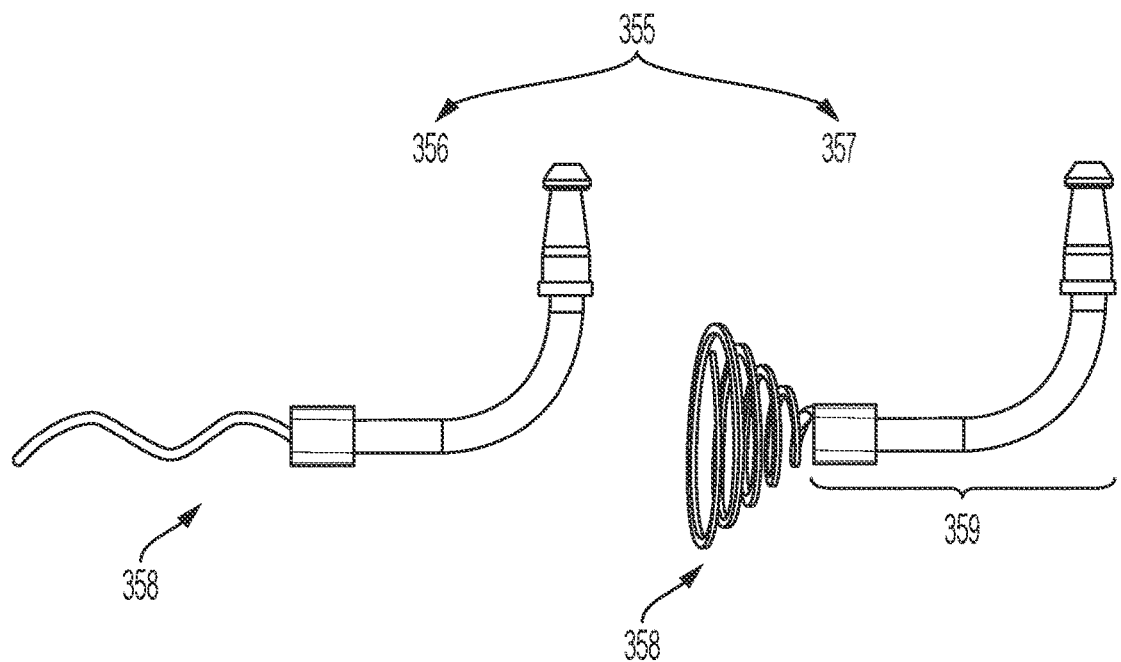
FIG. 70 is a side elevational view of an anchor support with a helical coil in a conical shape, in its undeployed form.
FIG. 71 is a side elevational view of an anchor support with a helical coil in a conical shape, in its deployed form.
Figures 73, 74:
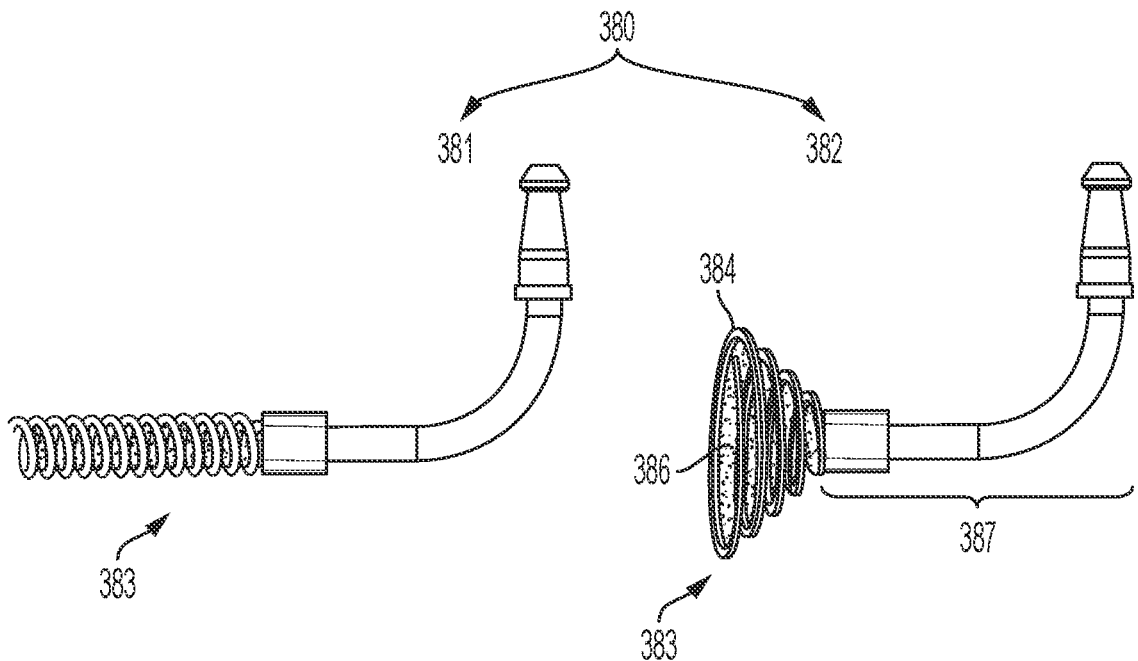
FIG. 73 is a side elevational view of an anchor support with covered helix, in its undeployed form.
FIG. 74 is a side elevational view of an anchor support with covered helix, it is deployed form.
Figures 75, 76:
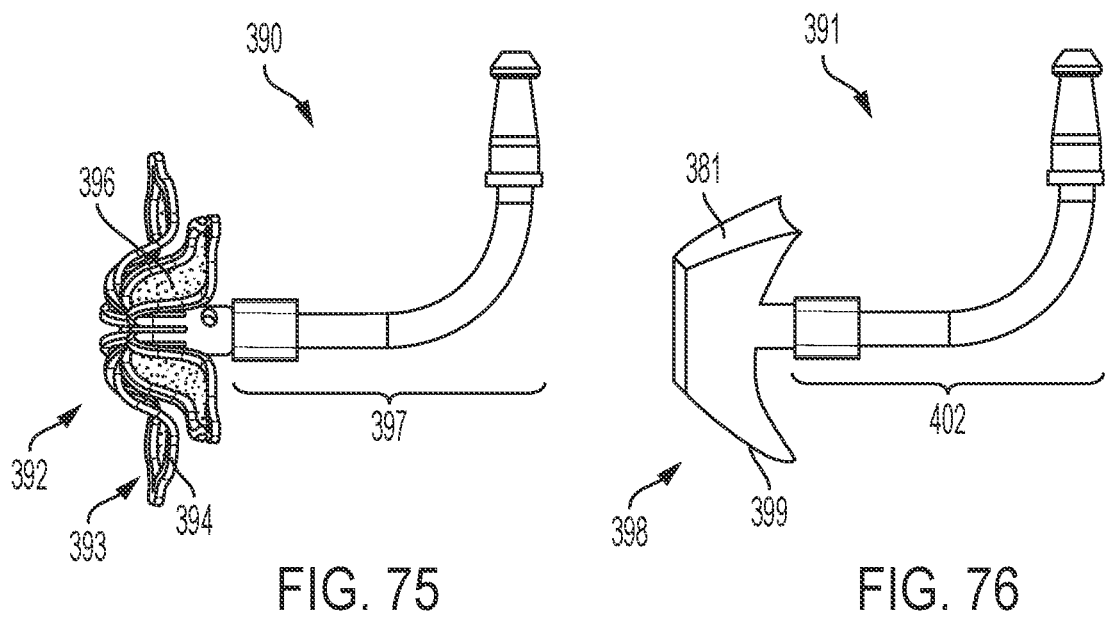
FIG. 75 is a side elevational view of an anchor support with umbrella-like petals.
FIG. 76 is a side elevational view of an anchor support with umbrella-like member.
Figures 77, 78:
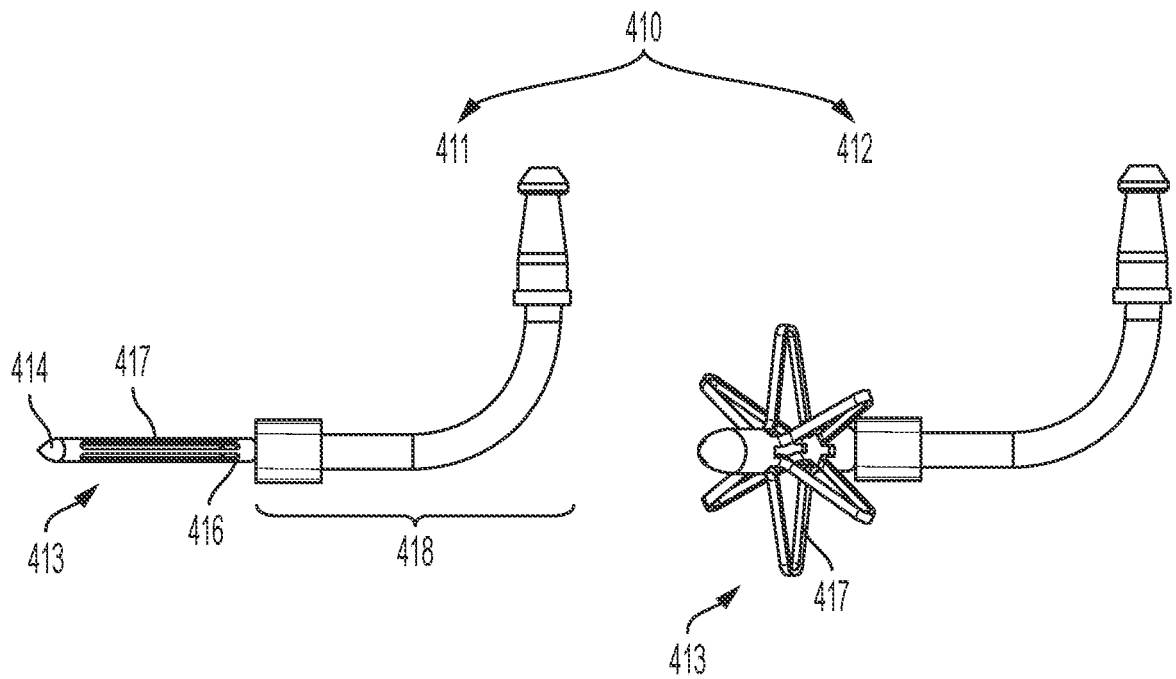
FIG. 77 is a side elevational view of an anchor support with star-like element in the its undeployed form.
FIG. 78 is a side elevational view of an anchor support with star-like element in its deployed form.
Figures 79, 80:
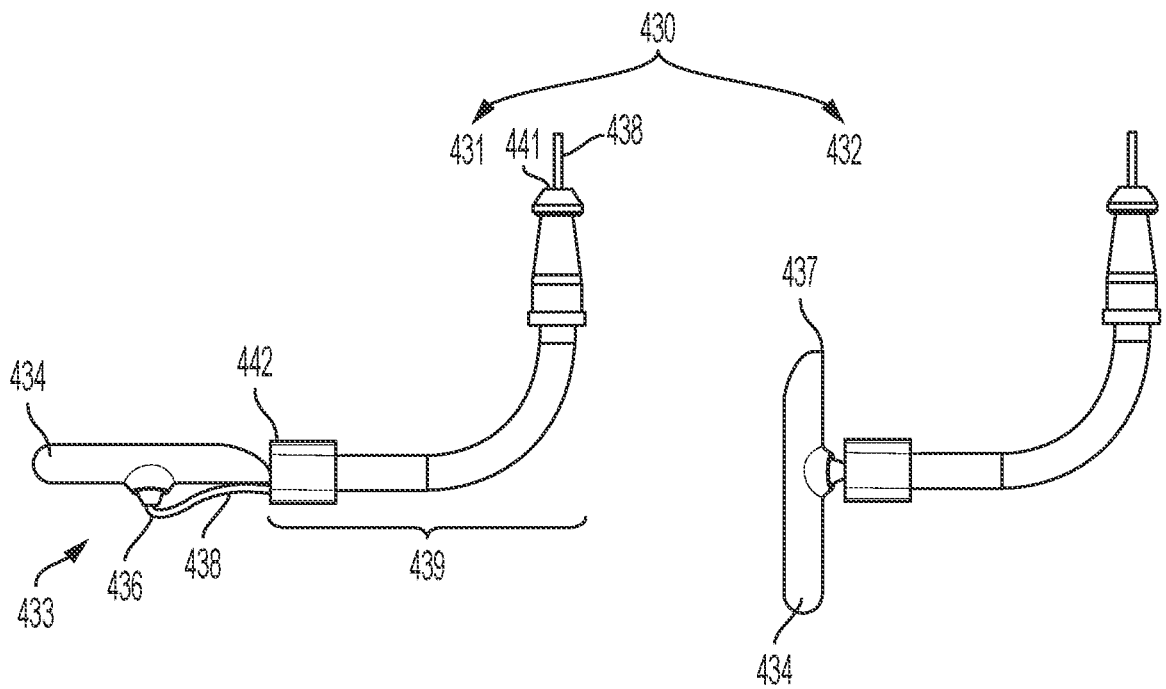
FIG. 79 is a side elevational view of an anchor support with pivoting bar in undeployed position.
FIG. 80 is a side elevational view of an anchor support with pivoting bar in deployed position.
Figure 99:
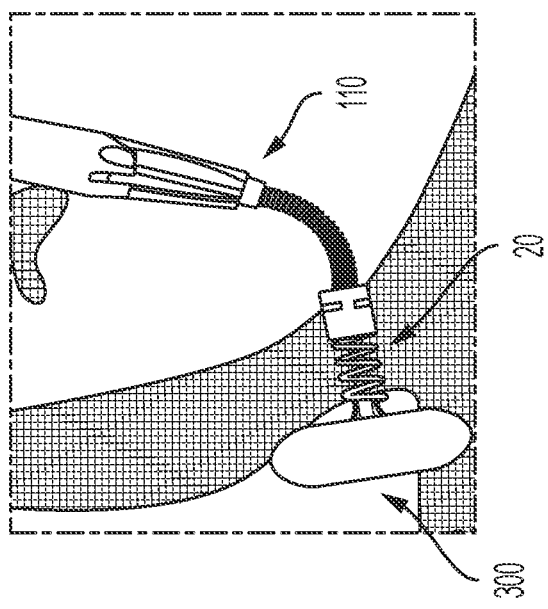
Figure 100:
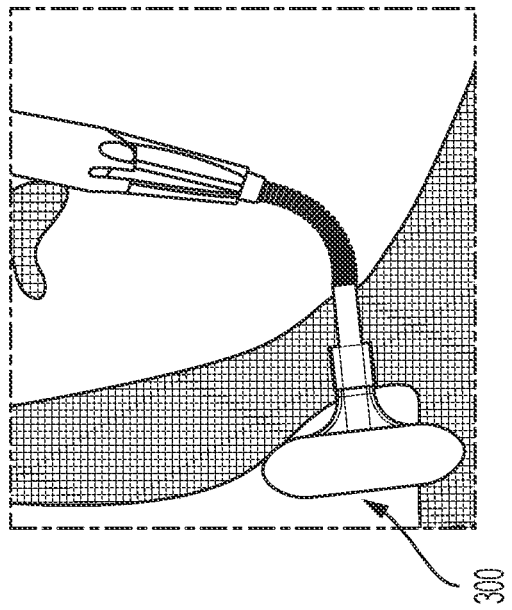
Figure 101:
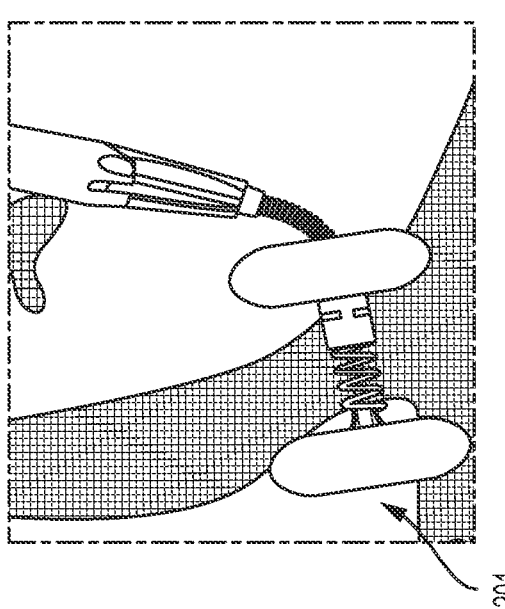
Figure 102:
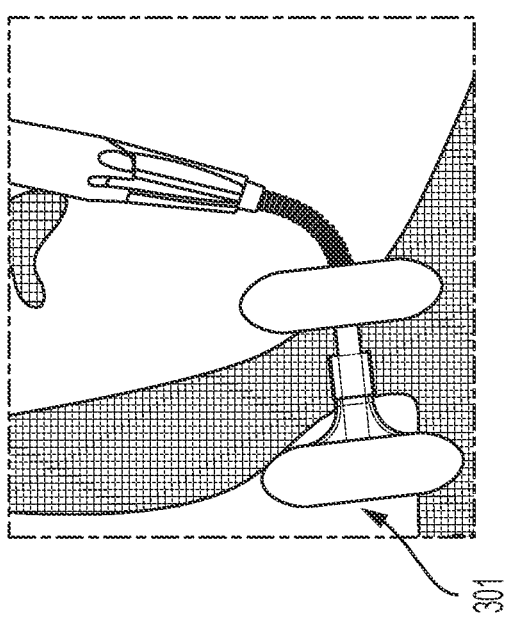
Figure 103:
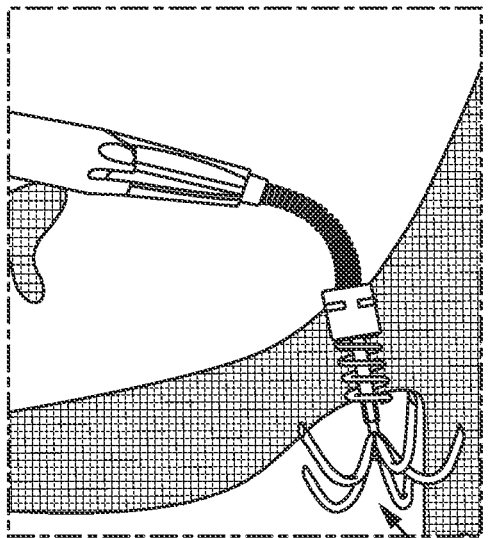
Figure 104:
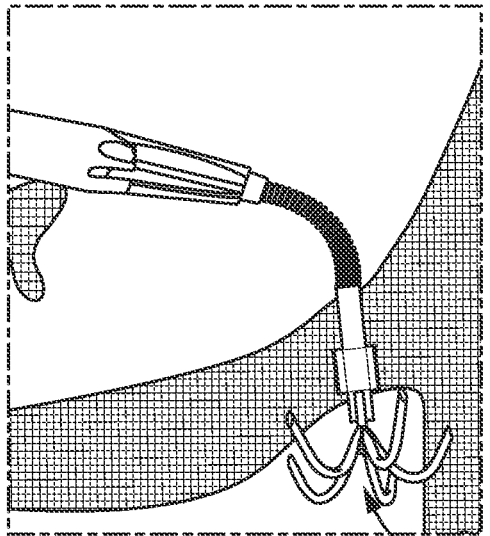
Figure 105:
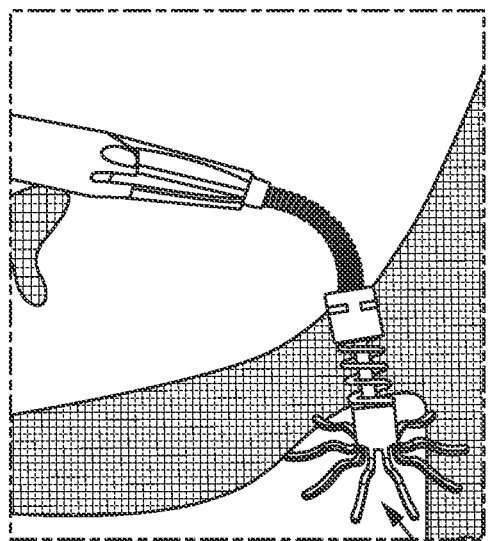
Figure 106:
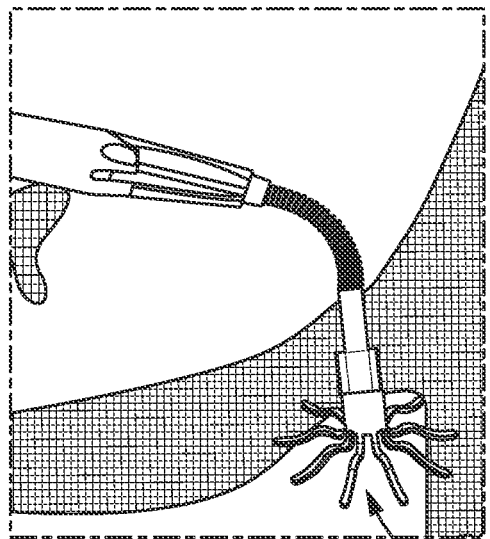
Figure 107:
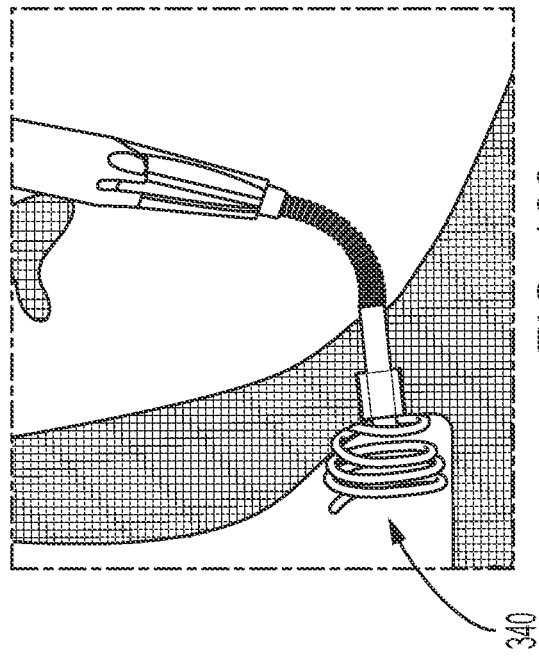
Figure 108:
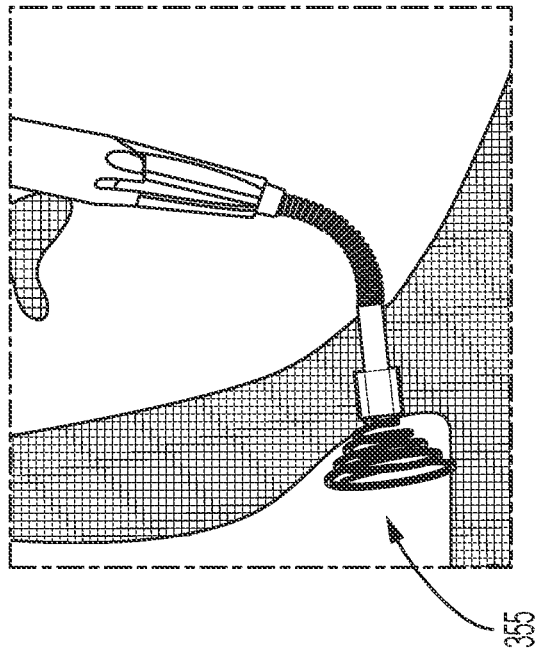
Figure 109:
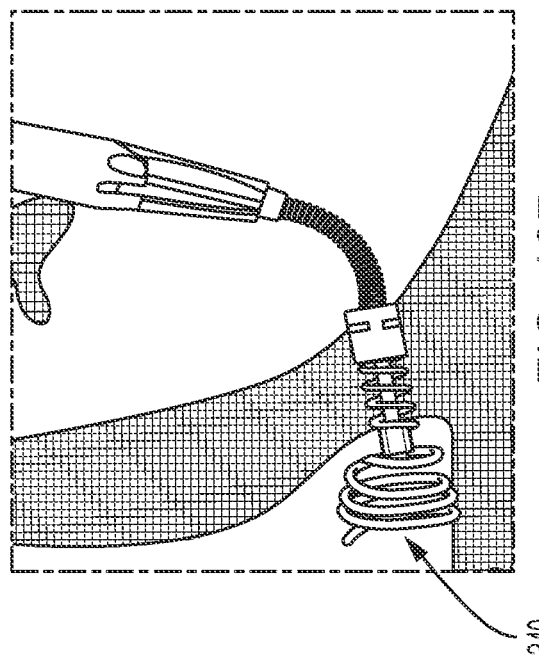
Figure 110:
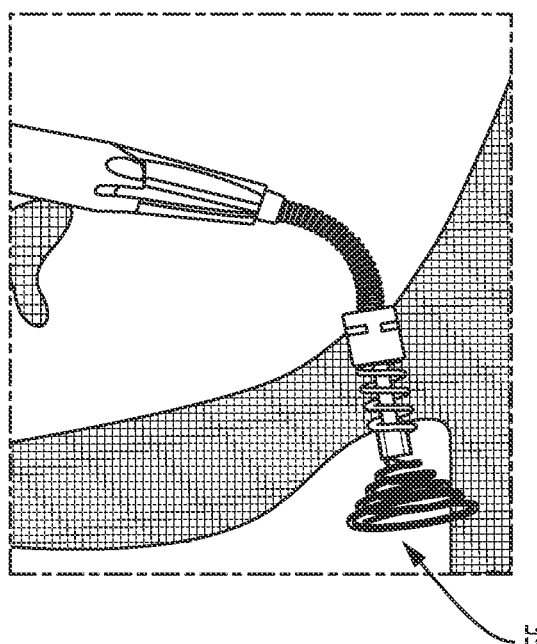
Figure 111:
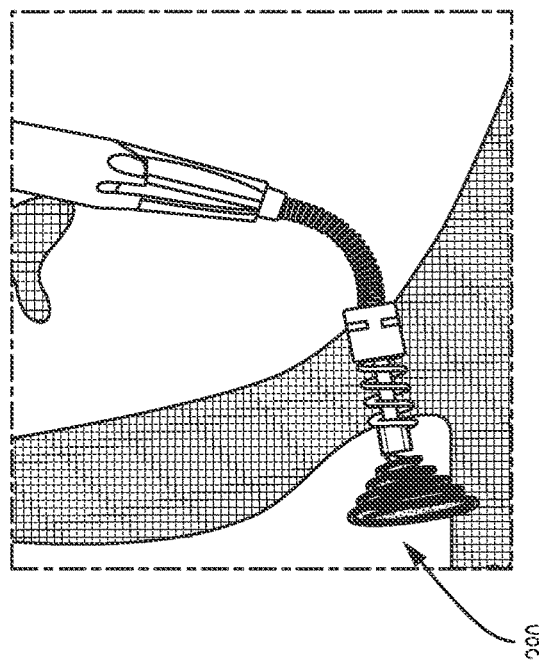
Figure 112:
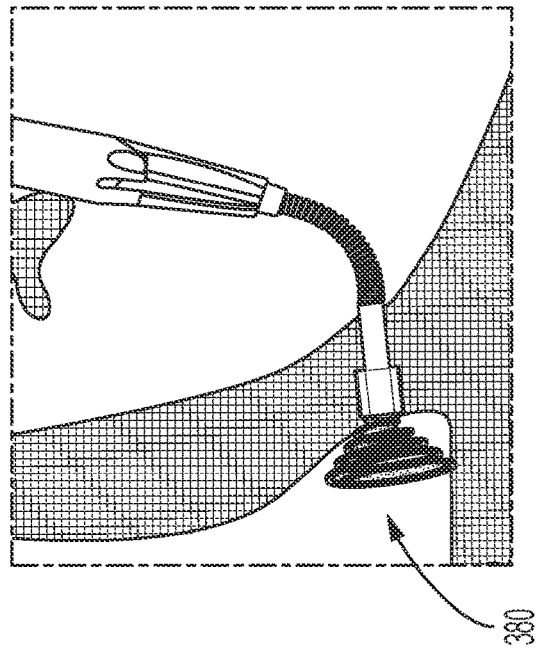
Figure 113:
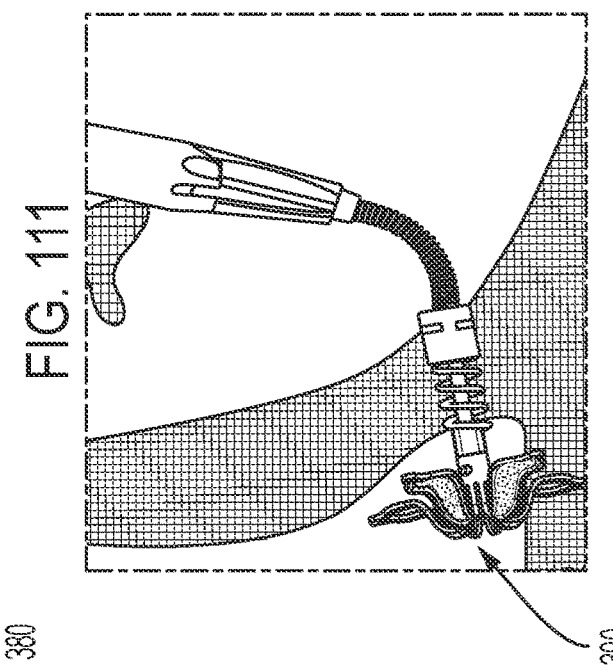
Figure 114:
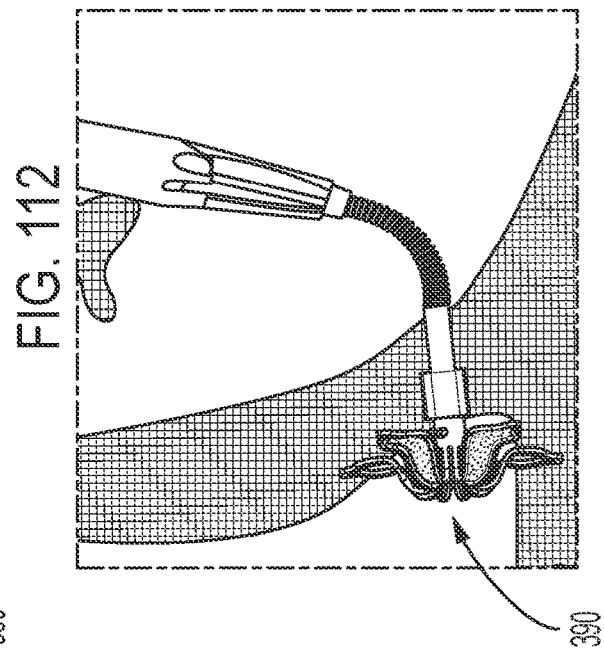
Figure 115:
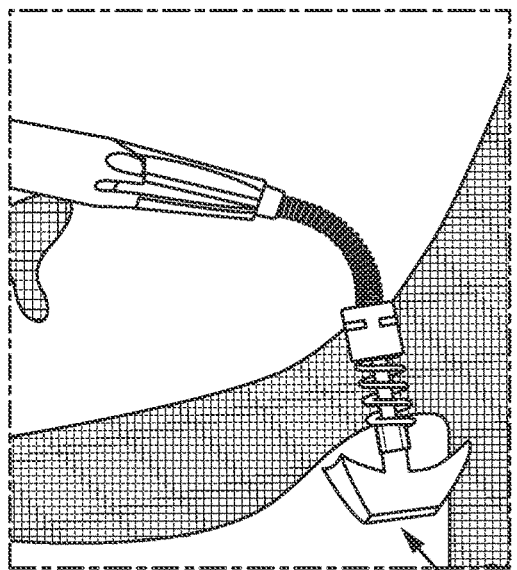
Figure 116:
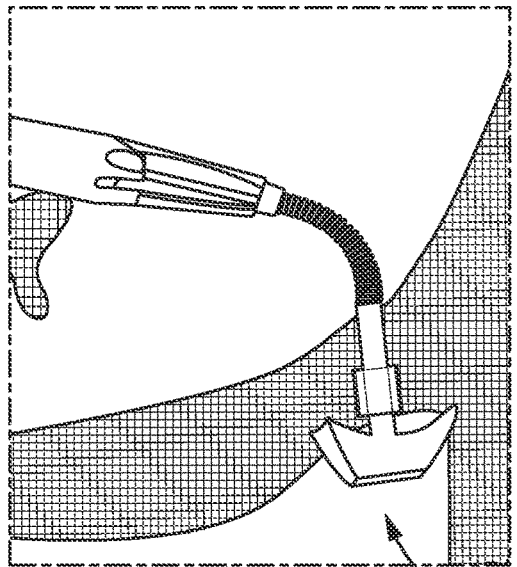
Figure 117:
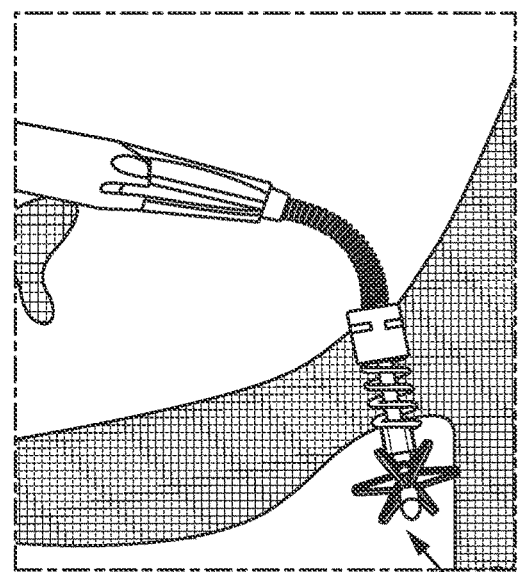
Figure 118:
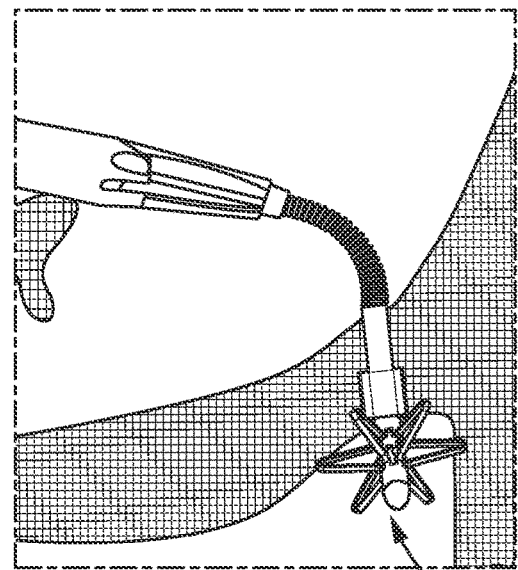
Figure 119:
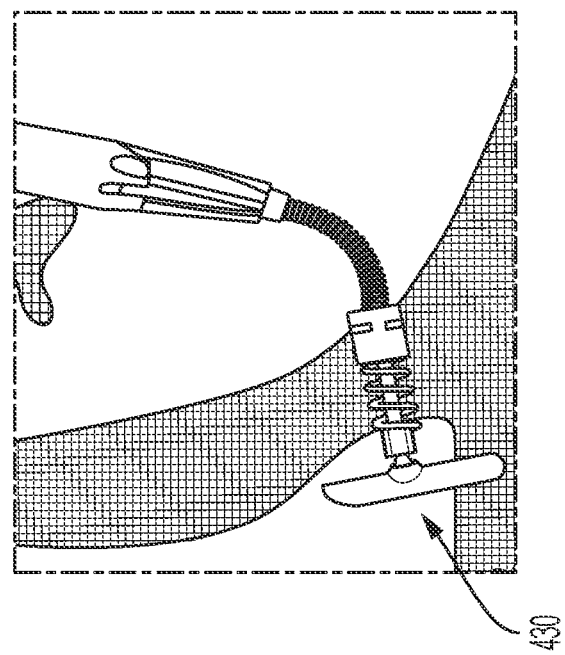
Figure 120:
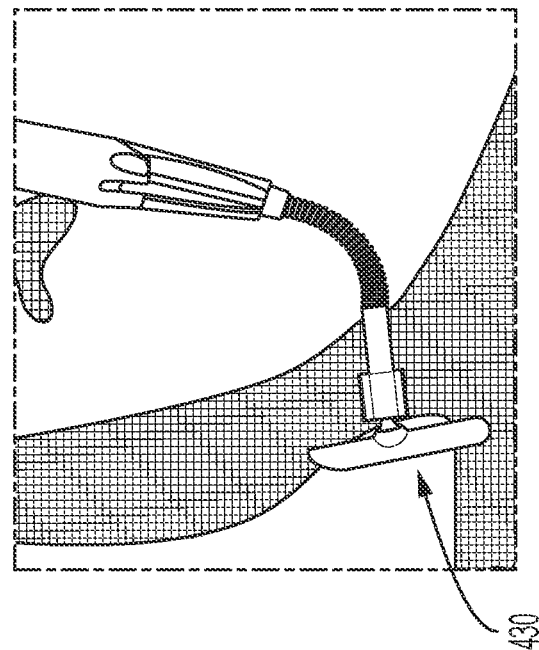

FIG. 92A is a cut-away perspective of a heart with the fixation element secured to the interventricular septum and the microcatheter across the septum with the screw dilator removed;

FIG. 92B is a magnified cut-away perspective of a heart with the fixation element secured to the interventricular septum and the microcatheter across the septum with the screw dilator removed;

FIG. 93 is a schematically represented view of a microcatheter having a needle tip dilator;

FIG. 94 is a schematically represented view of a microcatheter having a radiofrequency tip dilator;

FIG. 95 is a schematically represented view of a microcatheter having a laser tip dilator;

FIG. 96 is a schematically represented view of a microcatheter having a rotating burr dilator;

FIG. 97 is a schematically represented view of a microcatheter having a helical coil dilator;

FIG. 98 is a schematically represented view of a microcatheter having an oscillating tip dilator;

FIG. 99 is a cut-away perspective view of the anchor support with distal inflatable element of FIG. 60 with an anchor, connected to the tethering system;

FIG. 100 is a cut-away perspective view of the anchor support of FIG. 60 not associated with an anchor, connected to the tethering system;

FIG. 101 is a cut-away perspective view of the anchor support with distal and proximal inflatable elements of FIG. 61 associated with an anchor, connected to the tethering system FIG. 102 is a cut-away perspective view of the anchor support of FIG. 61 not associated with an anchor, connected to the tethering system;

FIG. 103 is a cut-away perspective view of the anchor support of FIG. 63 associated with an anchor, connected to the tethering system;

FIG. 104 is a cut-away perspective view of the anchor support of FIG. 63 not associated with an anchor, connected to the tethering system;

FIG. 105 is a cut-away perspective view of the anchor support of FIG. 65 associated with an anchor, connected to the tethering system;

FIG. 106 is a cut-away perspective view of the anchor support of FIG. 65 not associated with an anchor, connected to the tethering system;

FIG. 107 is a cut-away perspective view of the anchor support of FIG. 67 associated with an anchor, connected to the tethering system;

FIG. 108 is a cut-away perspective view of the anchor support of FIG. 67 not associated with an anchor, connected to the tethering system;

FIG. 109 is a cut-away perspective view of the anchor support of FIG. 71 associated with an anchor, connected to the tethering system;

FIG. 110 is a cut-away perspective view of the anchor support of FIG. 71 not associated with an anchor, connected to the tethering system;

FIG. 111 is a cut-away perspective view of the anchor support of FIG. 74 associated with an anchor, connected to the tethering system;

FIG. 112 is a cut-away perspective view of the anchor support of FIG. 74 not associated with an anchor, connected to the tethering system;

FIG. 113 is a cut-away perspective view of the anchor support of FIG. 75 associated with an anchor, connected to the tethering system;

FIG. 114 is a cut-away perspective view of the anchor support of FIG. 75 not associated with an anchor, connected to the tethering system;

FIG. 115 is a cut-away perspective view of the anchor support of FIG. 76 associated with an anchor, connected to the tethering system;

FIG. 116 is a cut-away perspective view of the anchor support of FIG. 76 not associated with an anchor, connected to the tethering system;

FIG. 117 is a cut-away perspective view of the anchor support of FIG. 78 associated with an anchor, connected to the tethering system;

FIG. 118 is a cut-away perspective view of the anchor support of FIG. 78 not associated with an anchor, connected to the tethering system;

FIG. 119 is a cut-away perspective view of the anchor support of FIG. 80 associated with an anchor, connected to the tethering system; and FIG. 120 is a cut-away perspective view of the anchor support of FIG. 80 not associated with an anchor, connected to the tethering system.

DETAILED DESCRIPTION OF THE INVENTION

The present invention is understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "tether" includes aspects having two or more tethers unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not. For the purposes of describing and defining the present invention it is noted that the use of relative terms, such as "substantially", "generally", "approximately", and the like, are utilized herein to represent an inherent degree of uncertainty that is attributed to any quantitative comparison, value, measurement, or other representation. These terms are also utilized herein to represent the degree by which a quantitative representation may vary from a stated reference without resulting in a change in the basic function of the subject matter at issue.

As used herein, "distal" refers generally to the operative end of a member or facing the direction of implantation and "proximal" refers generally to the end of a member facing direction of introduction or facing the user performing the implantation. As used herein, a "restraint" in terms of the anchor restraint 43 of the distal flange 41 and the anchor restraint of the proximal flange 210 may be of various geometric configurations, planar or multi-dimensional, without departing from the scope of the application. Particularly with regard to the distal flange 41, for the sake of discussion, a distal anchor restraint in the form of a disk is often shown and described.

The anchor support 40, and medical systems and methods including the anchor support 40, comprises either a single-stage anchor support 45 or a two-stage anchor support 245. The anchor support 40, either a single-stage 45 or two-stage 245, includes a distal flange 41 which is implanted with a single-stage flange delivery step. The anchor support 40 having a two-stage anchor support 245, also includes a proximal flange 210 and a second-stage delivery step for its implantation. The anchor support 40 thus includes at least a distal flange 41 and an anchor securing member 20 such as coil 21 extending distally from an anchor cap 23. The distal flange 41 is implanted into the heart wall through the center lumen of the anchor coil 21 as explained below. Extending proximally from the distal flange 41 is a flex connector 47 which may be either a wire 47 or a coil 48. With regards to the two-stage anchor support 245, the flex connector 47 extends between the distal 41 and proximal 210 flanges and a flexible compression element 204 extends proximally from the proximal flange 210 and a docking element 206/211 is positioned on its proximal end. The proximal flange is introduced over the flexible connector 47 and the flex connector base 49 wherein the docking element 206/211 is pushed over the flex connector base 49 and the docking arms 208/213 spring inward to secure the proximal flange 210. In all aspects, the system including the anchor support 40 is minimally invasively endovascularly implanted in the heart 1. The distal flange 41 and proximal flange 210 possesses different configurations as represented in the various Figures and discussed below. The anchor support 40 may also be secured with means of a any distal flange shown in FIGS. 60-80 as explained below, with or without an anchor coil 21.

Figure 1A:
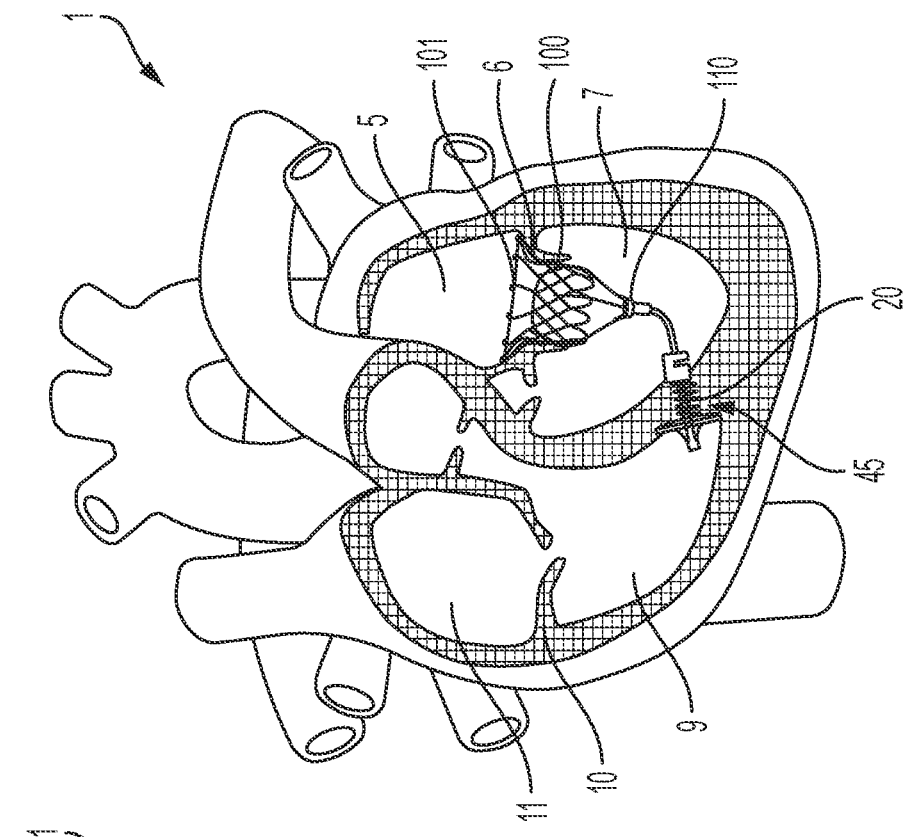
FIG. 1A is a cut-away perspective view of a heart showing a transcatheter heart valve positioned across the mitral valve in the heart and secured to the interventricular septum by the two-stage anchor support according to one aspect of the present invention.
Figure 1B:
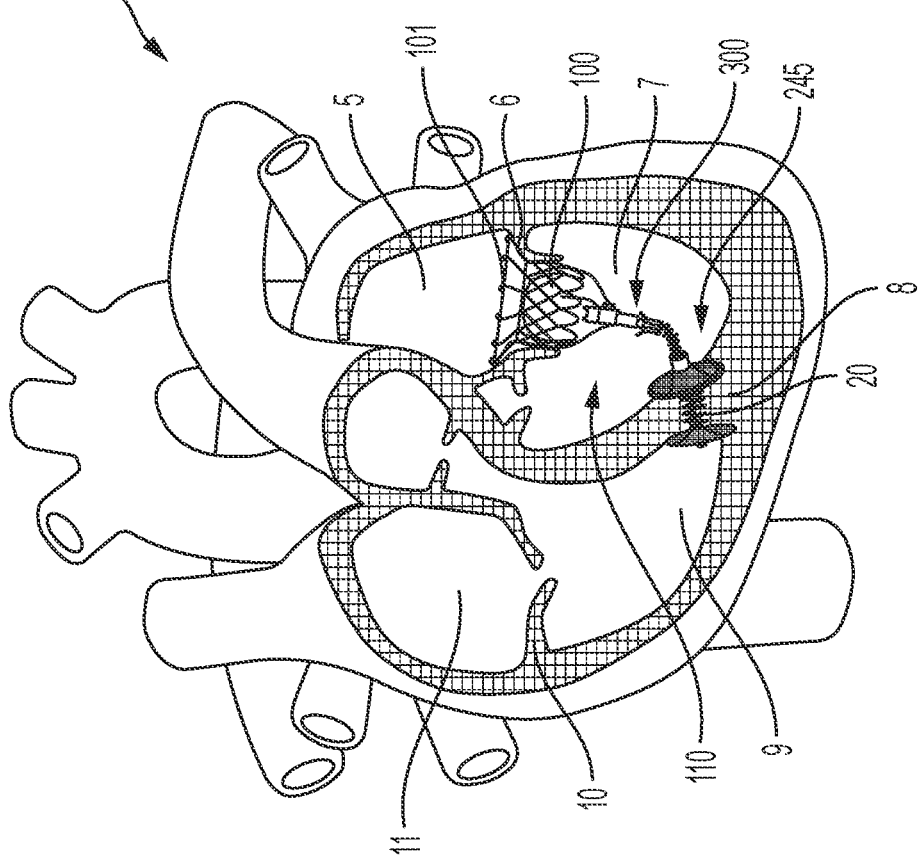
FIG. 1B is a cut-away perspective view of a heart showing a transcatheter heart valve positioned across the mitral valve in the heart and secured to the interventricular septum by the single-stage anchor support according to another aspect of the present invention
Figure 2A:
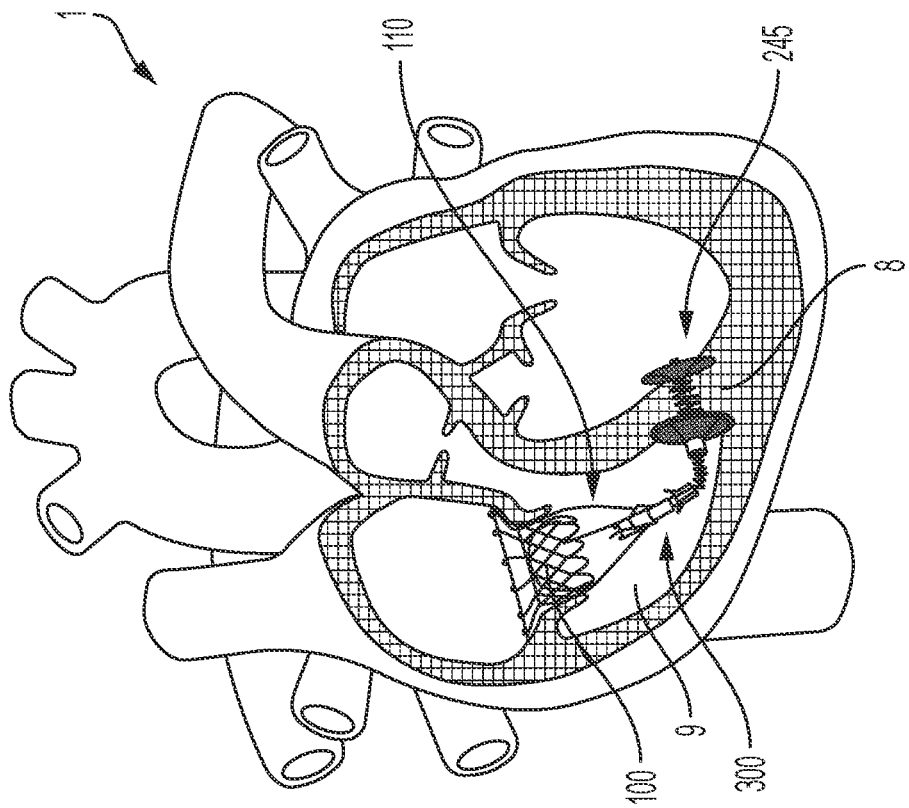
FIG. 2A is a cut-away perspective view of a heart showing the transcatheter heart valve positioned across the tricuspid valve in the heart and secured to the interventricular septum by the single-stage anchor support.
Figure 2B:
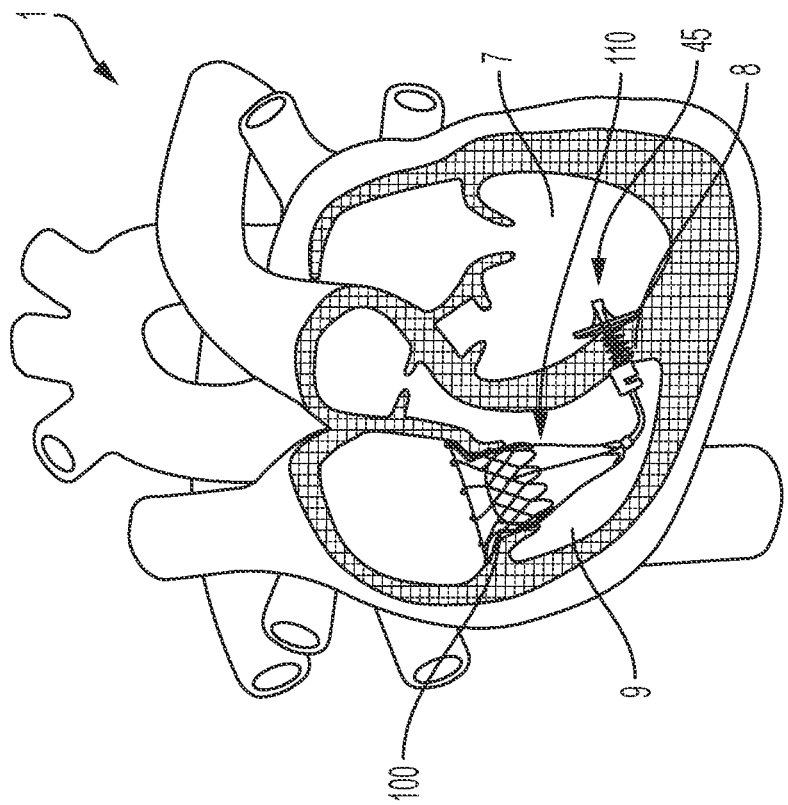
FIG. 2B is a cut-away perspective view of a heart showing the transcatheter heart valve positioned across the tricuspid valve in the heart and secured to the interventricular septum by the two-stage anchor support.
Figure 4:
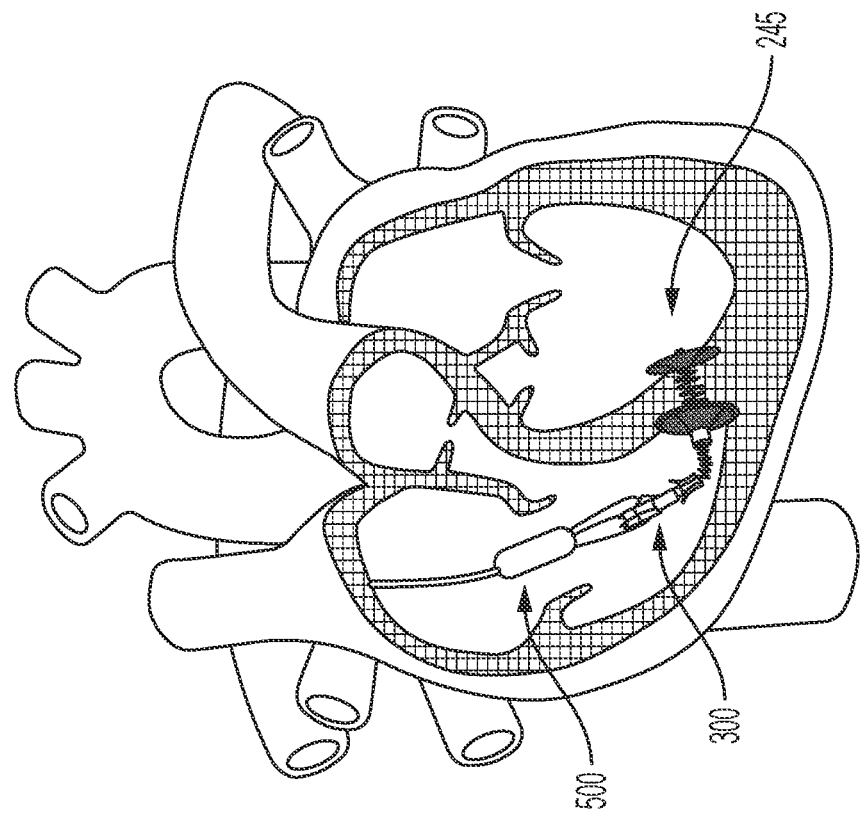
FIG. 4 is a cut-away perspective view of a heart showing a transcatheter coaptation element for a tricuspid valve in the heart and secured to the interventricular septum by the anchor support of FIG. 1A.
Figure 3:
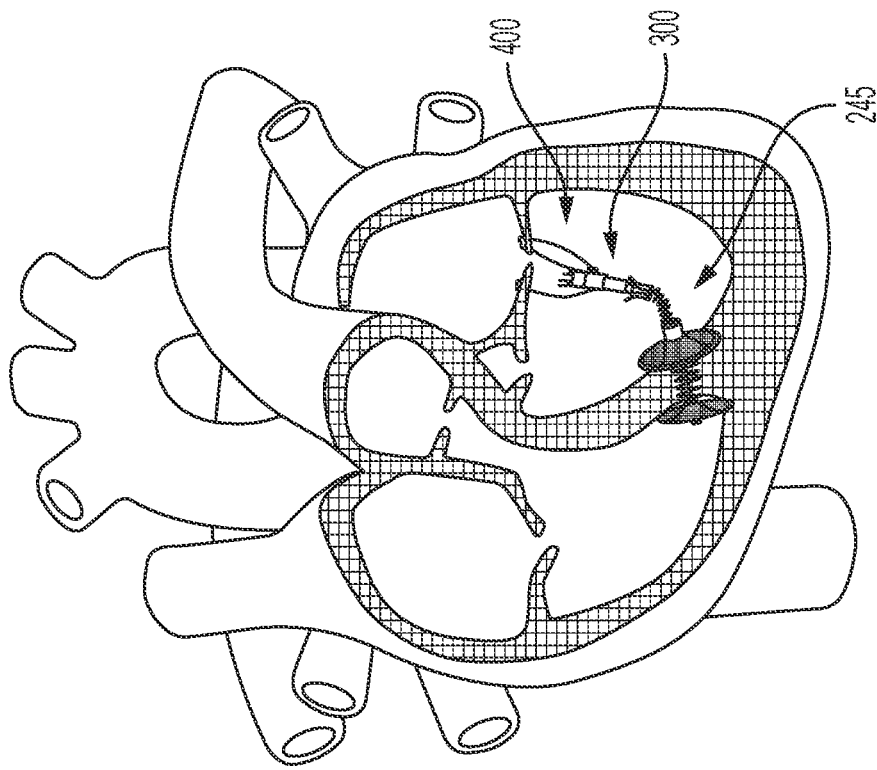
FIG. 3 is a cut-away perspective view of a heart showing a transcatheter chordal replacement system for a mitral valve in the heart and secured to the interventricular septum by the anchor support of FIG. 1A.
Figure 6:
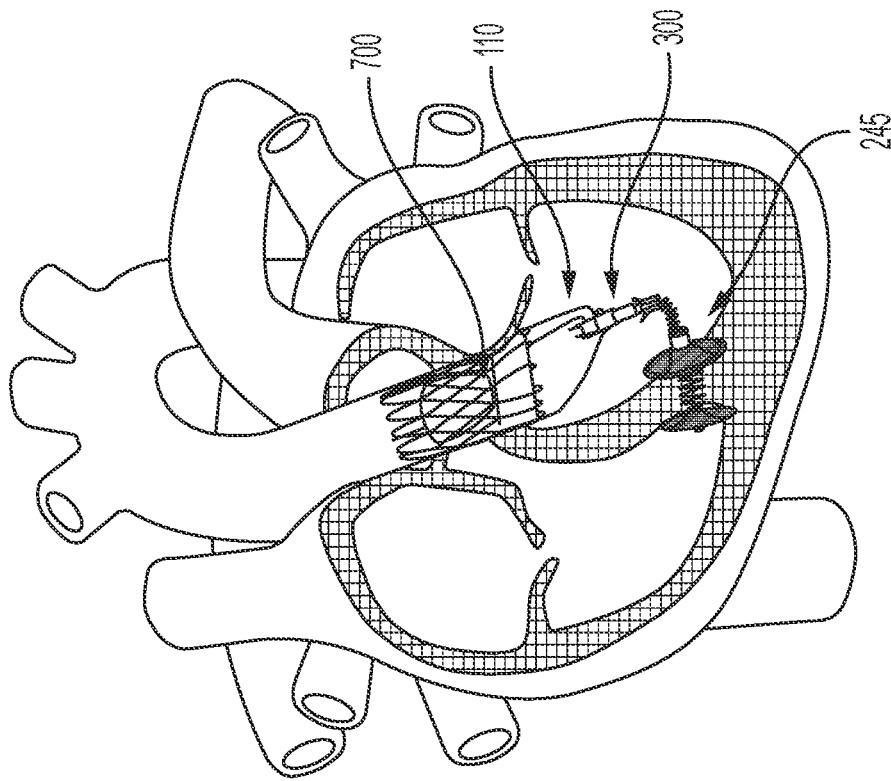
FIG. 6 is a cut-away perspective view of a heart showing a transcatheter left ventricular assist device in the heart secured to the interventricular septum by the anchor support of FIG. 1A.
Figure 5:
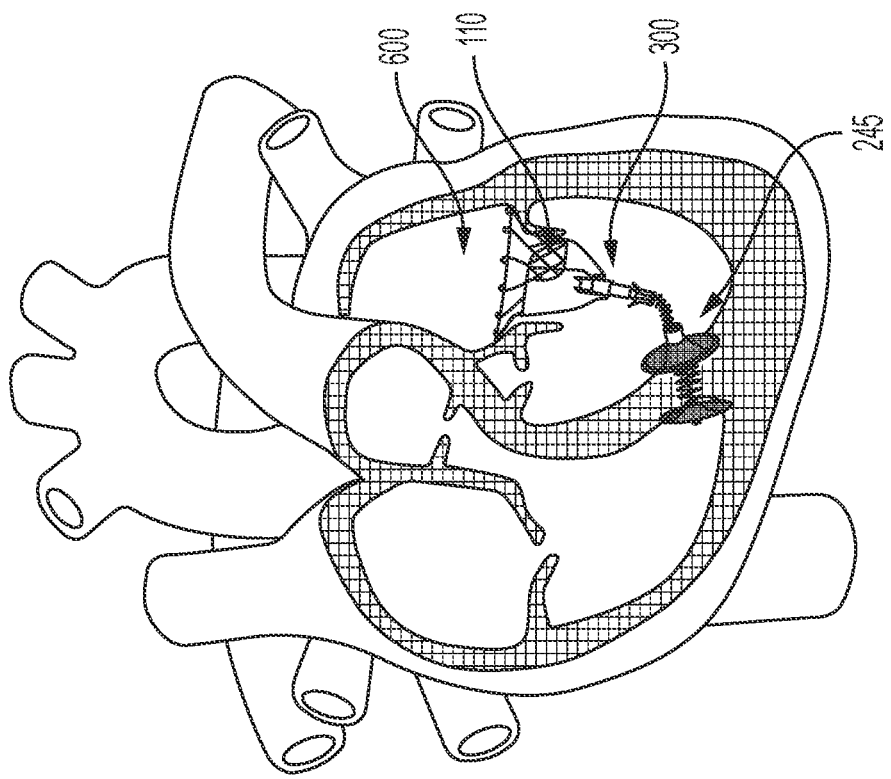
FIG. 5 is a cut-away perspective view of a heart showing a transcatheter hemi-valve replacement or leaflet augmentation element for a mitral valve in the heart and secured to the interventricular septum by the anchor support of FIG. 1A.

Tethering systems 110 and locking systems 300 are provided for use with the anchor supports 40. Additionally, methods and systems for endovascularly introducing and implanting anchors 20 and anchor support 40 to a cardiac wall using anchor delivery sheath 130, anchor support delivery system 140, and proximal flange delivery catheter 220 are described. The anchor support 45 or 245 is connected to a tethering system 110 and may be secured by locking system 300, to anchor an intracardiac implant, such as a valve 100 in the heart. The intracardiac implant may be connected to another intracardiac implant with or without an extension member in between. This application also relates to use of this system for the implantation of other intracardiac implants, such as valve repair devices (e.g. chordal repair systems 400, valve coaptation devices 500, leaflet augmentation systems 600, or annuloplasty rings), ventricular remodeling devices 800, or other cardiac implants such as transcatheter ventricular assist devices 700. FIGS. 1A and 1B illustrates the transcatheter valve 100 which has been implanted to the replace the native mitral valve (for example) according the medical assembly disclosed herein. FIGS. 2A and 2B illustrate the valve 100 implanted to replace the native tricuspid valve. FIG. 3 illustrates the transcatheter chordal system 400 implanted to provide chordal support to the native mitral valve. FIG. 4 illustrates the coaptation element 500 implanted to facilitate coaptation of the native tricuspid leaflets. FIG. 5 illustrates the hemi-valve or leaflet augmentation device 600 implanted to improve function of the native mitral valve. FIG. 6 illustrates the transcatheter left ventricular assist device 700 implanted to improve function of the left ventricle. FIG. 7 illustrates the transcatheter left ventricular remodeling system 800. The heart, of course, includes the left atrium 5, mitral valve 6, left ventricle 7, interventricular septum 8, right ventricle 9, tricuspid valve 10, and right atrium 11. The replacement valve 100 is positioned either to replace the mitral valve 6 or the tricuspid valve 10, or other intracardiac implants are positioned as shown in the various Figures. As shown and described in FIGS. 1A, 1B, 2A, 2B, by way of example, the anchor support 40 is used to secure a transcatheter valve to a tethering system 110 and locking system 300.

The Anchor

Referring now to FIG. 8, the anchor support 40 includes an anchoring member, which as shown in numerous figures, is an anchor coil 21 and anchor cap 23. The description which immediately follows refers to the an anchor coil 21 but it is to be appreciated that other anchoring members such as shown in other figures may replace the coil 21 without departing from the scope of the present invention. In one aspect, the anchor coil 21 is coupled to and extends from the distal end 27 of anchor cap 23. The anchor cap 23 has coupling recesses 24 configured to attach to an anchor torque driver 143. The anchor coil 21 of anchor 20 is configured to securely attach to an intracardiac wall such as the interventricular septum 8 of the heart 1. The anchor coil 21, as shown, is sized and configured as a helix to fix to an intracardiac wall and has an open central lumen. Optionally, however, the anchor coil 21 may be differentially sized (longer or shorter depending on patient-specific anatomy of the cardiac wall to which it attaches) and configured as an inclined plane, nail-like head, or as any other type of screw that would be known to those skilled in the art. In one aspect, the coil is composed of any known metal alloy, including, but not limited to, nitinol, titanium, or cobalt-chromium. In another aspect, the coil 21 may be covered in synthetic membranes such as polytetrafluoroethylene (PTFE), expanded polytetrafluoroethylene (ePTFE) or polyethylene terephthalate (PET). In another aspect, the coil 21 may be covered in biological tissue, such as bovine, ovine, porcine, or equine pericardium, or with any combination of anti-inflammatory drugs or other natural or synthetic compounds that might promote healing and limit inflammation. A tip(s) 22 of the anchor coil 21 optionally is constructed and/or coated with the same or different materials as the anchor screw 21 and may be fashioned as a blunt or sharp tip.

In use, the anchor 20 is secured to the cardiac wall by rotating anchor coil 21 until tip(s) 22 is at a desired depth in the cardiac wall. The depth to which anchor coil 21 is screwed in an adjustable manner according to not only the location within the heart but also the specific anatomy of a patient. For example, the anchor coil 22 may be implanted more deeply into the thicker portion of the interventricular septum, or more deeply into a patient with a thicker interventricular septum. By reversing the rotation of the anchor coil 21, the anchor 20 is removed safely from the cardiac wall, either to be repositioned, or to be removed entirely.

Rotation of anchor coil 21 occurs when the anchor torque driver 143, shown in FIGS. 9-13B, rotates the anchor cap 23 via the coupling of the anchor cap to the anchor torque driver distal end 146. The distal end 146 the anchor torque driver 143 comprises coupling arms 147, which have coupling tabs 148 that connect to the anchor cap 23 via the coupling recesses 24. The coupling tabs 148 remain outwardly expanded and attached to the coupling recesses 24 as long as the microcatheter 161 remains within this junction. Once the microcatheter 161 is retracted, the coupling tabs 148 may move inwards and away from the coupling recesses 24, allowing the anchor torque driver 143 to disengage from the anchor cap 23 of the anchor 20. The recesses 24 possesses any length, width, or polygonal shape to be complementary to coupling tabs 148.

The Distal Flange of the Anchor Support

Figures 14A, 14B, 14C:
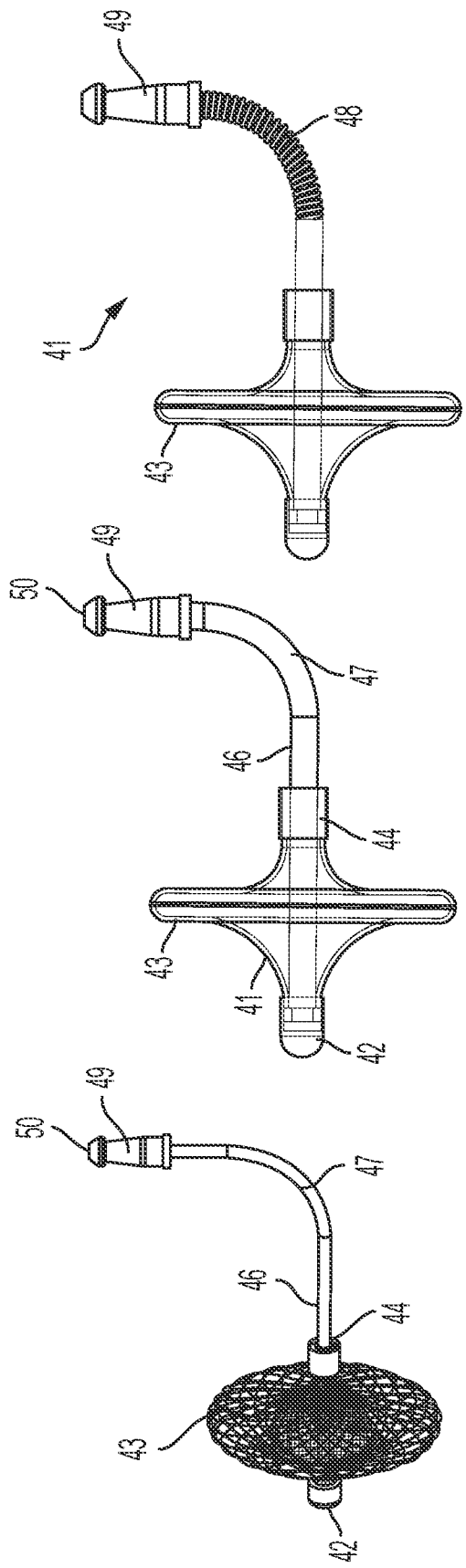
FIG. 14A is a perspective view of a distal flange having an anchor restraint according to the present invention.
FIG. 14B is a side elevational view of a distal flange having an anchor restraint according to another aspect of the invention and having a wire flex connector.
FIG. 14C is a side elevational view of a distal flange having the anchor restraint shown in FIG. 14B with a spring flex connector.

Referring to FIGS. 14A-C, the distal flange 41 consists of a cap 42, anchor restraint 43, proximal portion 44 of anchor restraint 43, rod 46 ending in flex connector 47, attached to flex connector base 49. The cap 42 may take the shape of a portion of a sphere or any polyhedron. The-anchor restraint 43 may be of any thickness or diameter, and may be circular, ellipsoid, polygonal, or be composed of one or more interconnecting polygonal shapes. In one aspect, the anchor restraint 43 or rod 46 are preferably composed of nitinol, but may composed of any known metal alloy, including, but not limited to titanium, or cobalt-chromium. In another aspect, the anchor restraint 43 or rod 46 can have additional fixation members (not shown) extending from any portion of surface to provide further engagement with tissue. Distal flange 41 includes a rod 46 attached to a flex connector 47 composed of a nitinol wire in FIGS. 14A and 14B and a flex connector 48 composed of a nitinol spring in FIG. 14C.

Flex connector 47/48 may have variable diameter, length, coil pitch and be composed of additional metallic alloys or polymeric plastics. In another aspect, any portion of the distal flange 41 may be covered in synthetic membranes such as polytetrafluoroethylene (PTFE), expanded polytetrafluoroethylene (ePTFE) or polyethylene terephthalate (PET), or covered in biological tissue, tissue, such as bovine, ovine, porcine, or equine pericardium, or with any combination of anti-inflammatory drugs or other natural or synthetic compounds that might promote healing and limit inflammation.

Figure 15:
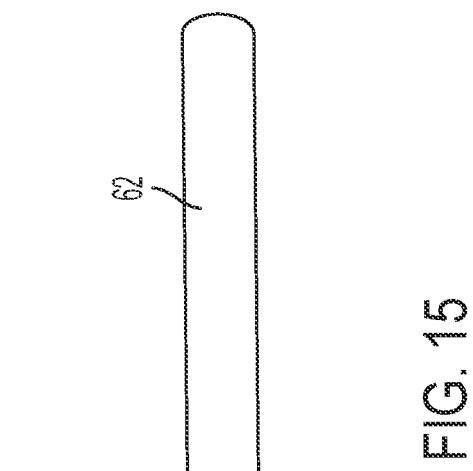
FIG. 15 is a perspective view of a hollow support delivery cable for delivery the distal flange.

Referring to FIG. 15, the distal flange delivery cable 60 includes a flexible delivery wire 62 having a distal threaded end portion 61 positioned on or formed in the distal end of the delivery wire 62. The delivery wire 62 is constructed of, but not limited to, stainless steel, nitinol or other metal alloys, with or without hydrophilic coatings, or with or without a polymer coating such as polytetrafluoroethylene (PTFE), expanded polytetrafluoroethylene (ePTFE) or polyethylene terephthalate (PET). The distal threaded end portion 61 is sized and configured to selective engage complementary threads formed in a cavity defined in the end 50 of the flex connector base 49. In use, before distal flange delivery, the distal threaded end portion 61 has been screwed into the end 50 of the flex connector base 49 of the flex connector 47 of distal flange 41, forming the distal flange delivery cable assembly which has been loaded in the distal flange support loader 80 (FIG. 17) and the distal flange support holder/loaded flange 90 is used to introduce the anchor support into microcatheter 161. As described more fully below, at the end of procedure after distal flange 41 delivery, with or without proximal flange docking, the distal threaded end portion 61 is unscrewed from the end 50 of the flex connector base 49, thereby detaching the flexible delivery wire 62 of the distal flange delivery cable 60 from the distal flange 41.

The Proximal Flange of the Anchor Support

Figure 21B:
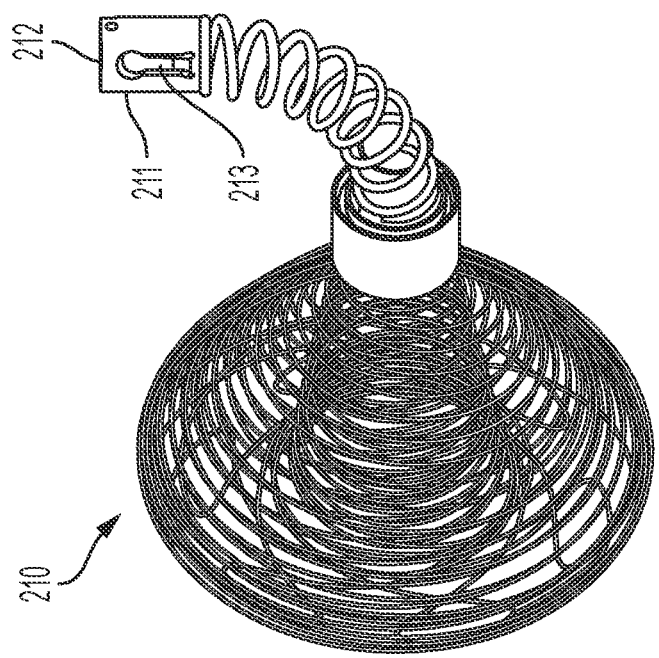
FIG. 21B is a perspective view of a proximal flange with the docking element according to another aspect of the present invention.
Figure 21A:
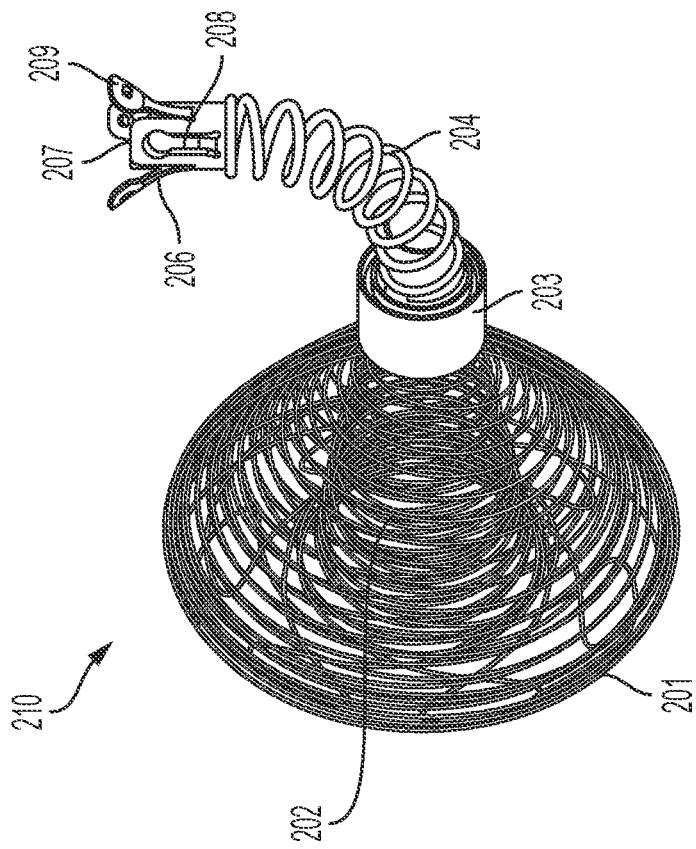
FIG. 21A is a perspective view of a proximal flange with the docking element comprised of a base and docking arms according to one aspect of the present invention.
Figure 22:
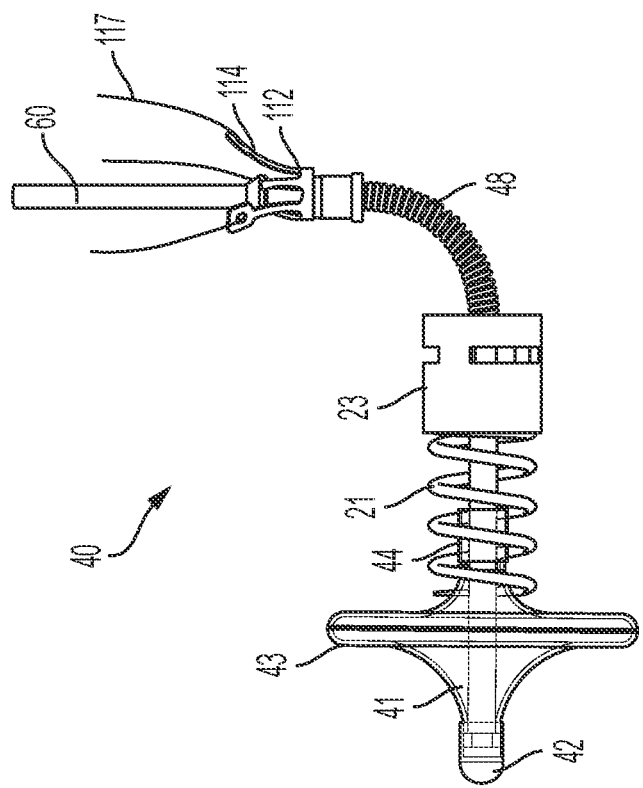
FIG. 22 is a side elevational view of the distal flange of the single-stage anchor support deployed and coupled to the anchor with tether assembly coupled to the flex connector base, which is attached to the delivery cable.

Referring to FIGS. 21A-B, the proximal flange 210 consists of disk 201, lumen 202, proximal connector 203, and flexible compression element 204. Proximal flange 210 has docking element 206 (FIG. 21A) or 211 (FIG. 21B). FIG. 21A shows a docking element 206 comprising distal end 207, at least one docking arms 208, and at least one external arm 209. FIG. 21B depicts a proximal flange 210 has docking element 211 comprised of distal end 212, and docking arms 213. The disk 201 may take the shape of like a circle, ellipse, or any polygon, be of variable thickness or diameter, and may take the same or different shape as the distal flange disk. Also, the disk and may bend in a concave or convex fashion towards the intracardiac wall, or take a frustoconical or any polyhedral shape towards the intracardiac wall. Connected to the proximal side of the disk 201 is the proximal connector, which may take the shape of a column, cylinder, or prism with any polygonal cross-section, and is connected to a flexible compression element 204, which may be a helical coil or conical coil of any thickness, radius, pitch, helix angle, or cone angle. Alternatively, the flexible compression element may take the shape of any spring with an alternative cross-sectional shape, such as a square, rectangle, or any polygon, or take the form of any compression element designed to handle an axial load. Attached to the proximal portion of the compression element 204 in proximal flange 210 is a docking element 206 in the shape of a circular or elliptical cylinder, or taking the shape of a prism with any polygonal cross-sectional shape. Docking element 206 has one or more docking arms 208 of any shape, thickness, width, height, that bend towards the center at same or different angles, and may be found anywhere around the perimeter of the docking element. The docking element 206 has one or more external arms 209, and an end 207. Docking element 211 may have any of the shape properties of docking element 206, without the external arms 209, and has docking arms 213. The lumen 202 starts at the end of disk 201 and continues through the proximal connector 203, is in continuity with the internal channel of the flexible compression element 204, which is continuity with the internal channels and ends 207 and 212 of docking elements 206 or 211, respectively. Any of the components of proximal flange 210 are preferably composed of nitinol, but may composed of any known metal alloy, including, but not limited to titanium, or cobalt-chromium. In another aspect, any portion of the proximal flange 210 may be covered in synthetic membranes such as polytetrafluoroethylene (PTFE), expanded polytetrafluoroethylene (ePTFE) or polyethylene terephthalate (PET), or covered in biological tissue, tissue, such as bovine, ovine, porcine, or equine pericardium, or with any combination of anti-inflammatory drugs or other natural or synthetic compounds that might promote healing and limit inflammation.

The Proximal Portion of the Anchor Support and Tethering System

Figure 16A:
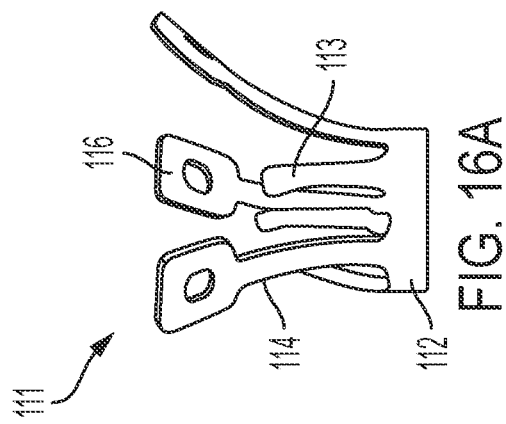
FIG. 16A is a side elevational view of a tether swivel used at least in connection with the single-stage anchor of FIGS. 20A-20C.
Figure 16B:
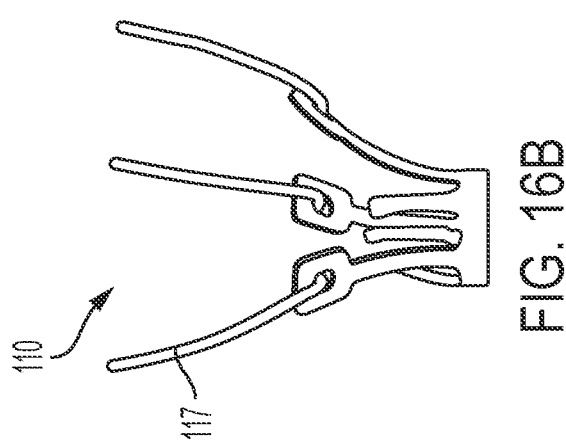
FIG. 16B is a side elevational view of the tether swivel of FIG. 16A attached to chords.
Figure 16C:
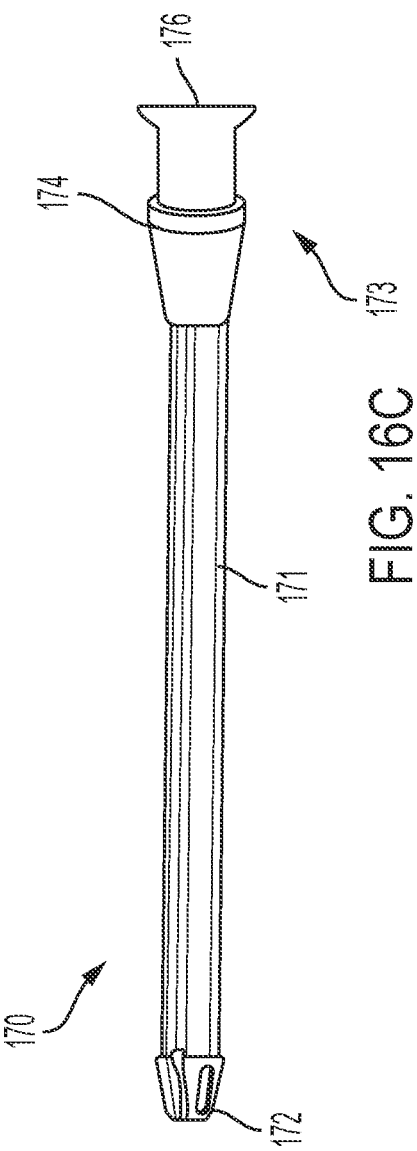
FIG. 16C is a side elevational view of the tether delivery system for docking the tether swivel on the flex connector base of the distal flange at least in connection with the single-stage anchor.

As shown in FIGS. 16A-B, a tether swivel base 112 having at least one tether swivel locking arm 113 and at least one tether swivel chord arm 114 is provided. As shown, a distal end of the swivel locking arm 113 and tether swivel chord arm 114 are securely coupled to or formed monolithically with the tether swivel base 112. A shown, the plurality of tether swivel locking arms 113 and tether swivel chord arms 114 are spaced equally around the circumference of the tether swivel base 112, though it is contemplated that the locking arms 113 and chord arm 114 need not be spaced equally. An eyelet 116 is defined by the tether swivel chord arm 114. The eyelet 116 is coupled to one or more chords 117.

In one aspect, when tether assembly 110 is coupled to anchor support 45 and anchor 21, the tether assembly 110 has freedom to rotate about a longitudinal axis of the anchor support 45 a full 360 degrees. Optionally, in another aspect, the tether assembly 110 may be constrained to lesser degrees of rotation by interaction of a portion of the tether assembly 110 with the flex connector base 49.

As shown, in another aspect, coupling occurs when the tether assembly 110 is advanced over the flexible delivery wire 62 of the anchor support delivery cable 60. As the tether swivel base 112 advances over the proximal end 50 of flex connector base 49, the proximal end 50 pushes the tether swivel locking arms 113 outward, until the arms advance underneath the proximal end 50, when they spring back into original position thereby locking the tether assembly 110 to the flex connector base 49 and therefore to the rest of the anchor support 45 and associated anchor support 45. Any portion of the tether assembly may be composed of any metal or metal alloy, and the chords may be composed of any combination of nitinol wire, any surgical suture, expanded polytetrafluoroethylene (ePTFE) or ultra-high-molecular-weight polyethylene (UHMPWE or UHMW).

The Anchor Support Assemblies

As shown in FIG. 28, after anchor support 40 delivery to the interventricular wall, distal flange delivery cable assembly is delivered through the anchor coil 21. Once fully deployed, the anchor support disk 43 is past the tip of 22 of anchor coil 21, with the anchor support rod 46 extending through the center of the anchor coil 21 and anchor cap 23, and the flex connector 47 extending proximally from the anchor cap 23, and remains connected to the distal flange delivery cable 60 via the attachment of the distal threaded end 61 to the end 50 of the flex connector base 49. The anchor support delivery cable 60 serves as a guide wire for the proximal flange 210. In anchor support 245, as shown in FIGS. 29-34, the proximal flange 210 has been advanced over the flex connector 47 of distal flange delivery cable assembly with the flex connector 47 extending through lumen 202, through flexible compression element 204, and through docking element 211. The end 212 of docking element 211 is below end 50 of flex connector base 49, and the locking arms 213 are flexed toward the segment of flex connector 47 just below the flex connector base 49 so that the docking element 211 prevents the proximal flange 210 from moving proximally relative to the flex connector 47. Because the docking element 211 or 206 is fixed relative to the flex connector base 49, the flexible compression element 204, connected via the proximal connector 203, urges the disk 201 forward. The disks of the distal and proximal flanges can be at variable distances depending on the thickness of the intracardiac wall between the flanges as illustrated in FIGS. 31-34. After docking of the proximal flange, then anchor support delivery cable 60 serves as a guide wire for delivery of tethering system and locking system.

The Anchor Delivery Sheath

Referring now to FIG. 35, the anchor delivery sheath 130 is illustrated. The sheath 130 has a shaft 131, and a distal end 132. In another aspect, at least a portion of the shaft 131 is flexible so that the distal end 132 is flexed and positioned at or adjacent to an intracardiac wall such as the interventricular septum 8. Flexion occurs when the deflection knob 134 of the anchor delivery sheath handle 133 is rotated. The anchor support delivery system 140 is inserted into the lumen 136, extending from the proximal portion of anchor delivery sheath handle 133 to the distal end 132.

The Proximal Flange Delivery Catheter

Figure 24:
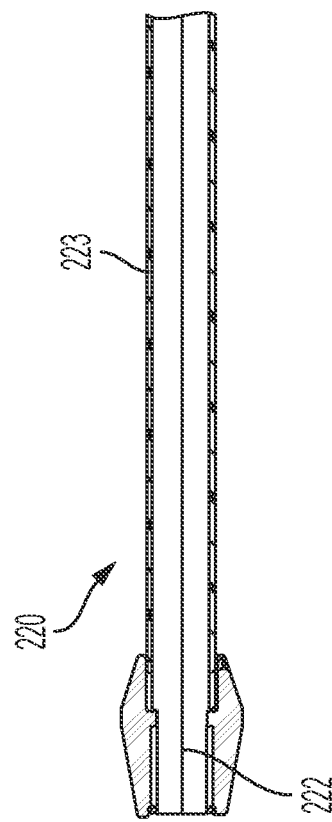
FIG. 24 is a cross-sectional view of proximal flange delivery catheter.
Figure 23:
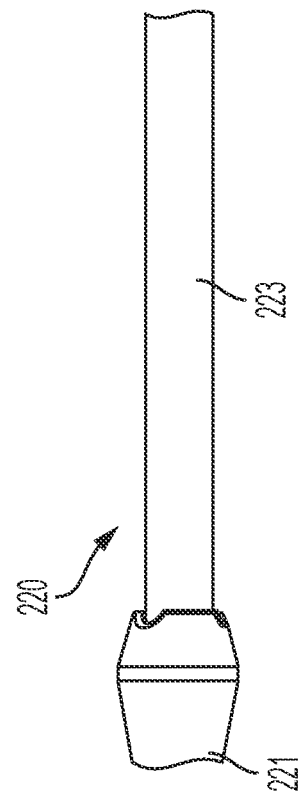
FIG. 23 is a side elevational view of the proximal flange delivery catheter.

Referring now to FIGS. 23-24, shown is the proximal flange delivery catheter 220 with distal end 221, lumen 222, and shaft 223. In one aspect, the distal end 221 reversibly mates with the proximal flange 210 because the docking element 206 or 211 is reversibly coupled inside the lumen 222 of the distal end 221. In another aspect, at least a portion of the shaft 223 is flexible so that it can track the curve of the anchor support delivery system 140 and the anchor delivery sheath 130.

The Anchor and Distal Flange Delivery System

Referring now to FIGS. 35-38B, the anchor support delivery system 140 for delivering the anchor 21 and deploying the distal flange delivery cable assembly 65 across the interventricular septum is illustrated. The delivery system 140 comprises the anchor 21, anchor torque driver 143, microcatheter 161 and screw dilator 162, access valve 151, and anchor support delivery handle 150. As illustrated in FIGS. 9-10, the anchor torque driver 143 consists of a shaft 144 with inner lumen 149, ending in distal end 146, with one or more coupling arms 147 ending in coupling tabs 148 which mate with the coupling recesses 24 of anchor cap 23 of anchor 20. In another aspect, the anchor driver 143 is coupled to the delivery handle 150 by entering the valve 151. Rotation of the anchor driver is controlled by the anchor coil knob 152 at distal end of the delivery handle 150.

As illustrated in FIG. 13A, the microcatheter 161 has a distal shaft 164 integrated with a proximal control hub 166. In another aspect, the microcatheter screw dilator 162 with tip 163 resides inside the microcatheter 161, as illustrated in FIGS. 13B and 38B, the microcatheter screw dilator tip 163, like the anchor coil, may be differentially sized (longer or shorter depending on patient-specific anatomy of the cardiac wall to which it attaches) and configured as an inclined plane, nail-like head, or as any other type of screw that would be known to those skilled in the art. Alternatively the dilator tip 163 may be a cone, sphere, cylinder, or any polyhedral shape for the purpose of penetrating tissue. In one aspect, the coil is composed of any known metal alloy, including, but not limited to, nitinol, titanium, or cobalt-chromium. The microcatheter may be of any diameter or length with lumen to accommodate the microcatheter dilator, and the microcatheter may be composed of any metallic alloy or polymeric plastic.

As illustrated in FIG. 38B, the dilator tip 163 of microcatheter screw dilator 162 and associated microcatheter 161 reside within the anchor cap 23 of the anchor 20, and the proximal portion of each extend through the lumen of the anchor torque driver 143. Inside the anchor torque driver 143, the microcatheter extends into the anchor support delivery handle 150 via the access valve 151, and the proximal control hub 166 of the microcatheter 161 couples inside the microcatheter holder 160 within the ground 153 of the anchor support delivery handle 150.

The Method of Implanting the Anchor

Figure 41:
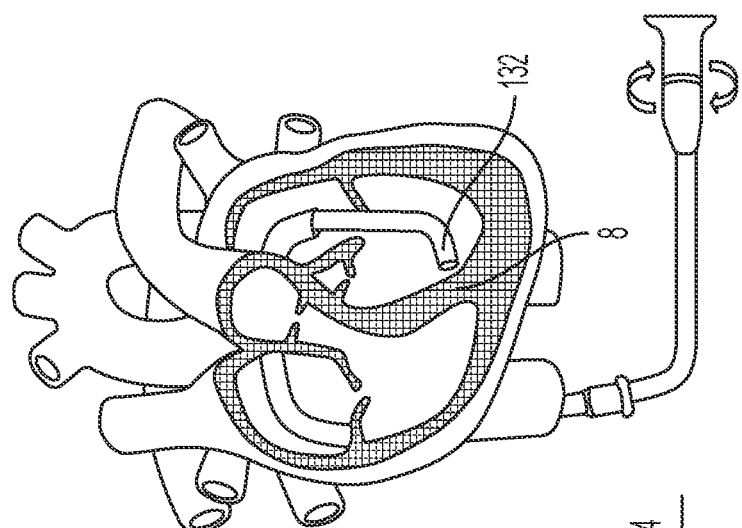
FIG. 41 is a cut-away perspective view of a heart with the anchor delivery sheath positioned next to the interventricular septum.
Figure 40:
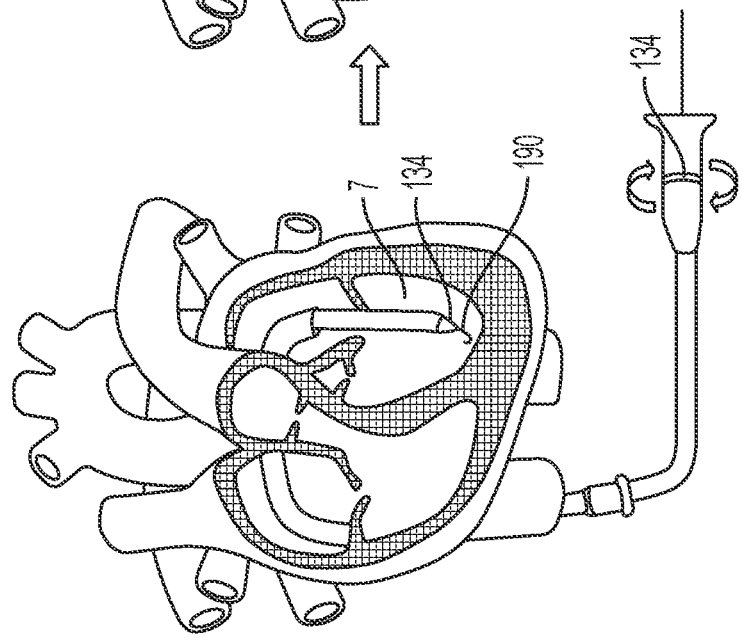
FIG. 40 is a cut-away perspective view of a heart with an anchor delivery sheath advancing into the left ventricle over a guidewire.
Figure 39:
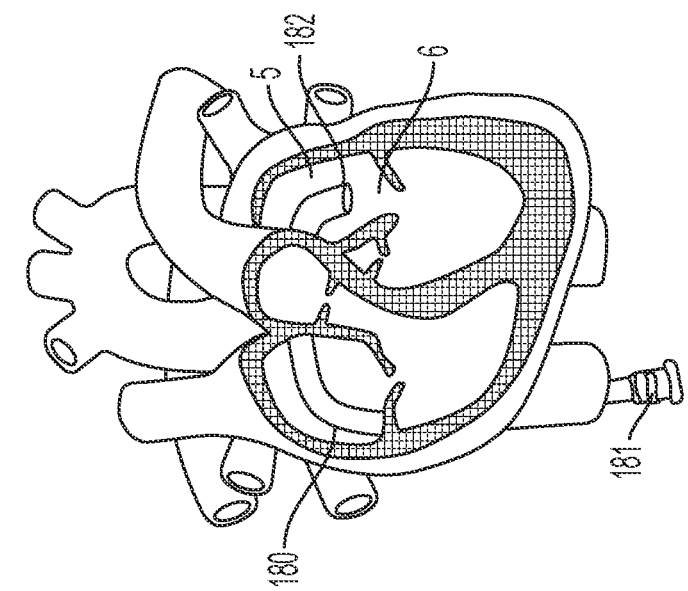
FIG. 39 is a cut-away perspective view of a heart with a trans-septal introducer sheath in delivery position.

To install anchor 20 to interventricular septum 8, as shown in FIG. 39, access is obtained to the femoral vein (not shown) using standard techniques, and a trans-septal crossing system (not shown) is used to traverse the interatrial septum into the left atrium 5. Over a wire in the left atrium 5, the trans-septal sheath 180 is advanced into the left atrium 5; the trans-septal sheath deflector knob 181 is rotated until the trans-septal sheath tip 182 is pointing to the mitral valve 6. As shown in FIGS. 40-41, a j-wire 190 is advanced over into the left ventricle 7, and the anchor delivery sheath 130 is advanced over the wire into the left ventricle 7, followed by removal of the j-wire 190 and the anchor delivery sheath dilator 136 Next, rotation of the deflector knob 134 bends the distal tip 132 of the anchor delivery sheath 130 toward the interventricular septum 8.

Figure 42B:
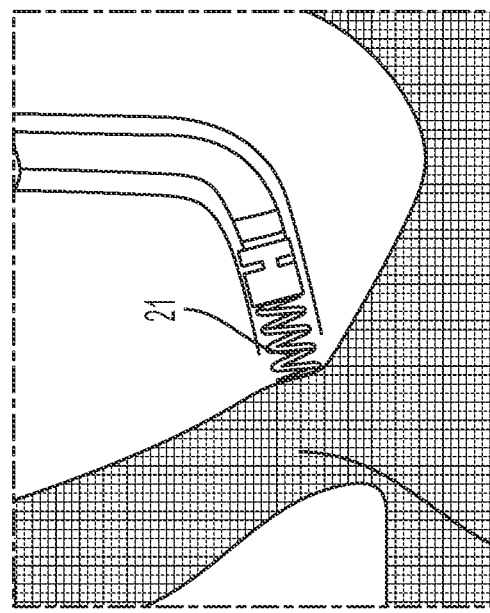
FIG. 42B is a magnified cut-away perspective view of a heart with the anchor positioned within the anchor delivery sheath next to the interventricular septum.
Figure 42A:
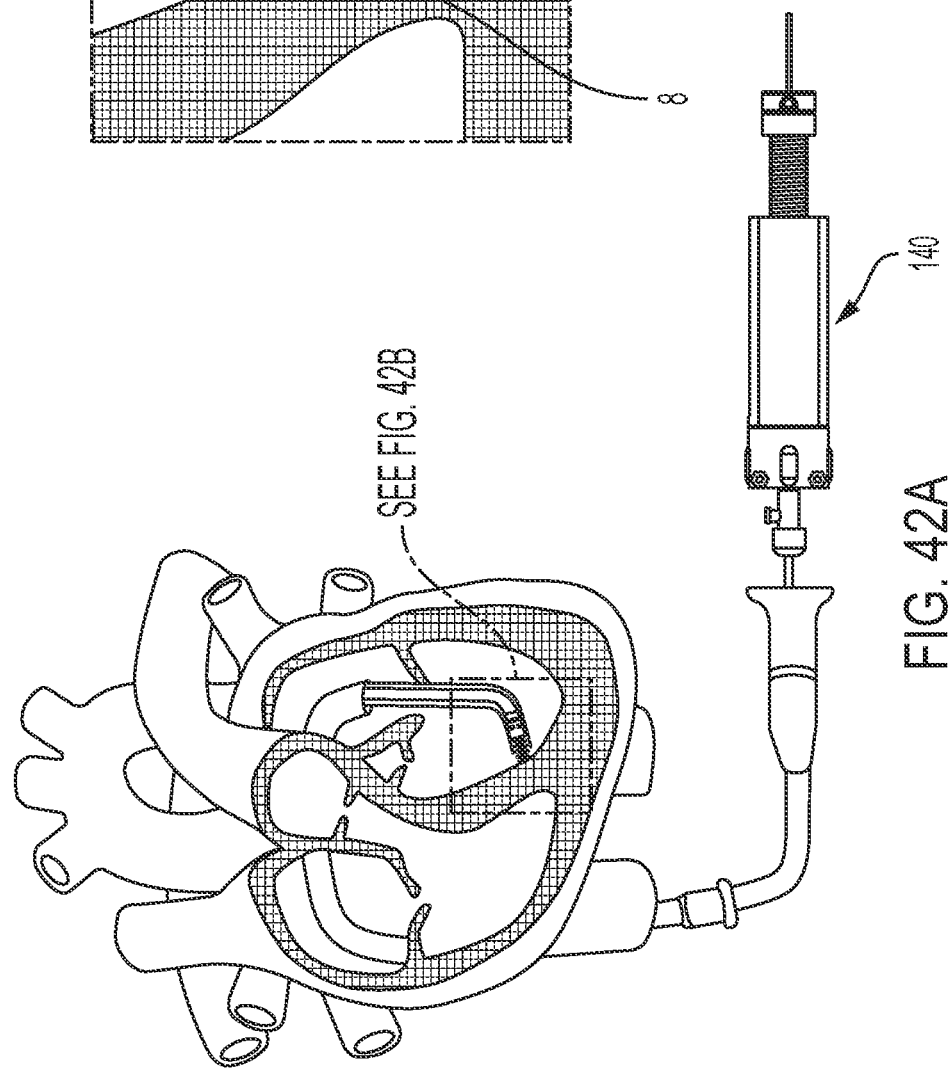
FIG. 42A is a cut-away perspective view of a heart with the anchor positioned within the anchor delivery sheath next to the interventricular septum and the anchor support delivery system being introduced.

As shown in FIGS. 42A-B, the delivery system 140 is inserted into the anchor delivery sheath 130, until the anchor coil 21 of the anchor 20 extends outside the distal tip 132 of the anchor delivery sheath 130 and abuts the interventricular septum 8. As shown in FIGS. 43A-B, rotation of the anchor coil knob 152 rotates the anchor driver 143, which rotates the coupled anchor cap 23, thereby driving the anchor coil 21 across the interventricular septum.

The Method of Advancing the Microcatheter

As illustrated by FIGS. 44-46 once the anchor 20 is secured in the septum, the microcatheter with screw dilator traverses the septum according to the following steps: 1) the dilator knob 158 is pushed forward until the magnets 159 of the head 155 of the threaded rod 154 secure the dilator knob 158, so that the dilator tip 163 extends outside the end of the microcatheter 2) rotation of the microcatheter control knob 156 rotates the threaded rod 154, which rotates the microcatheter holder 160, thereby rotating the proximal control hub 166 of the microcatheter 161. This rotation causes the microcatheter 161 and screw tip dilator 162 to rotate in unison, and both advance across tissue as the dilator tip 163 of the dilator 162 screws through the tissue 3) Once the microcatheter and screw tip dilator have traversed the tissue, the dilator knob 158 is pulled out, thereby pulling out screw tip dilator 162, leaving microcatheter 161 across the tissue for anchor support delivery.

The Method of Implanting the Distal Flange

Figure 48D:
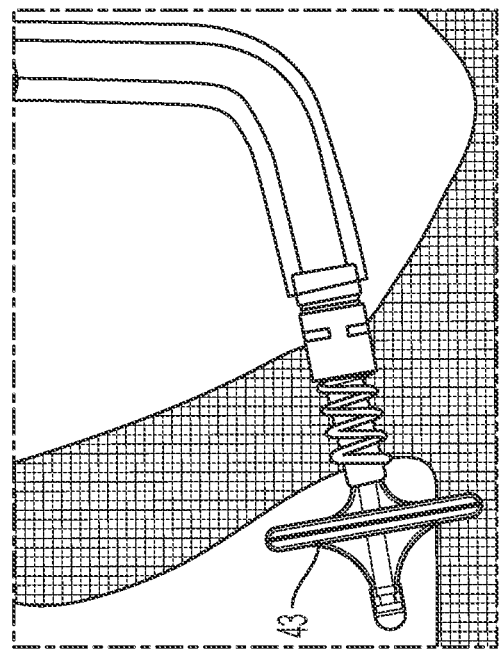
FIG. 48D is a cut-away perspective of a heart with the microcatheter across the interventricular septum and the anchor restraint of the single-stage anchor support deployed and expanded against the interventricular septum.
Figure 48C:
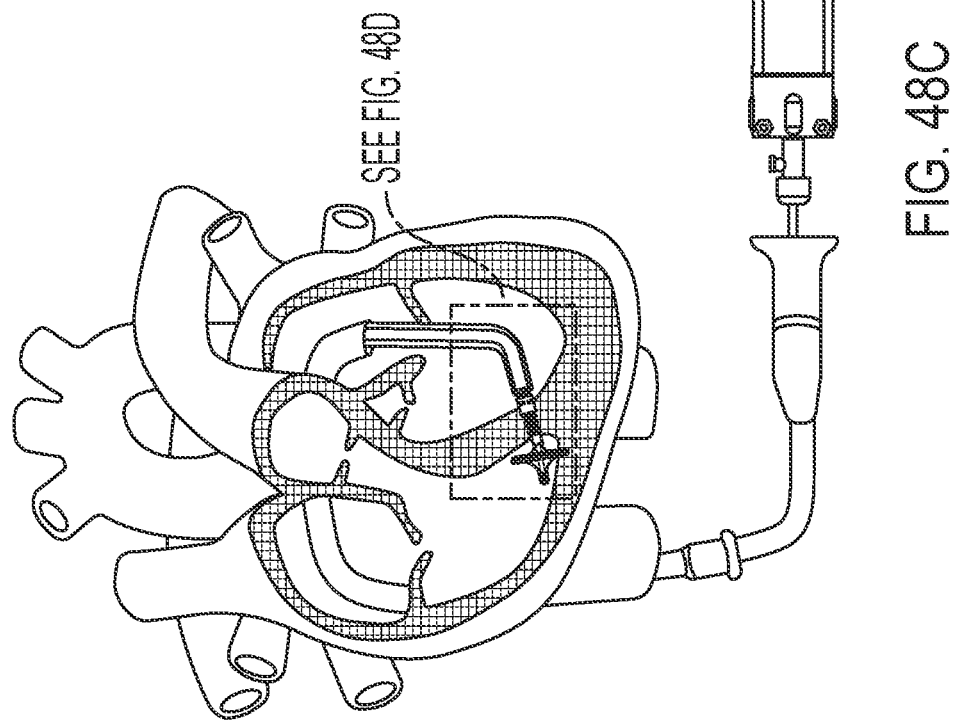
FIG. 48C is a cut-away perspective of a heart with the microcatheter across the interventricular septum and the anchor restraint of the single-stage anchor support deployed against the interventricular septum.

As shown in FIGS. 47A-B, the distal flange 41 collapsed within the distal flange loader 80 is inserted into the proximal end of the anchor support delivery system 140 via the head 155 of the threaded rod 154. As shown in FIGS. 48A-B, the distal flange 41 is pushed inside the microcatheter 161 until the anchor restraint 43 exits the microcatheter and expands on the other side of the septum. FIGS. 48C and 48D show the same procedure with the flange 41 according to another aspect of the invention.

Figure 49B:
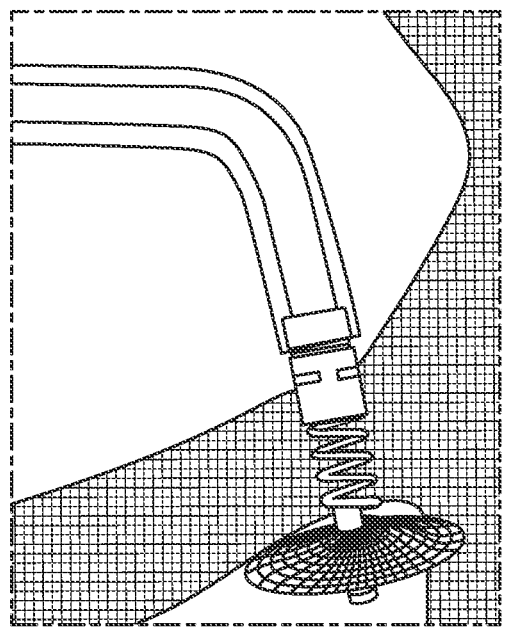
FIG. 49B is a magnified cut-away perspective view of a heart with the distal flange of the two-stage anchor support deployed and microcatheter being retracted.
Figure 49A:
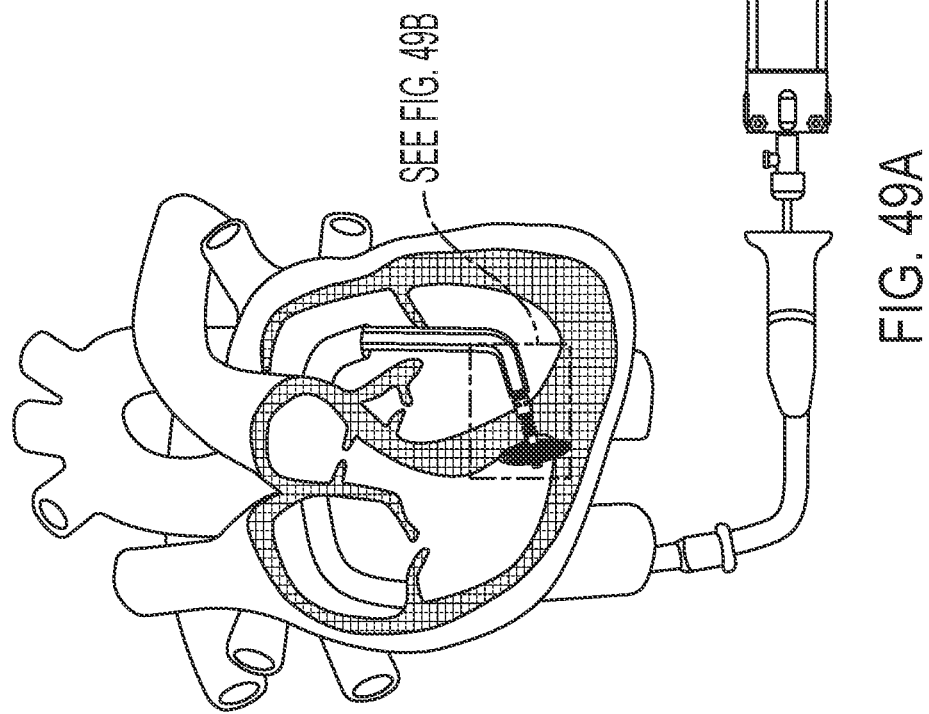
FIG. 49A is a cut-away perspective view of a heart with the distal flange of the two-stage anchor support deployed and microcatheter being retracted.
Figure 53B:
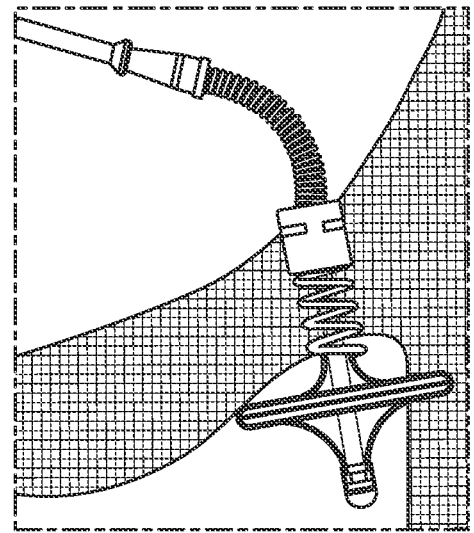
FIG. 53B is a magnified cut-away perspective view of a heart with the single-stage anchor support delivered across the septum and connected to the delivery cable.
Figure 53A:
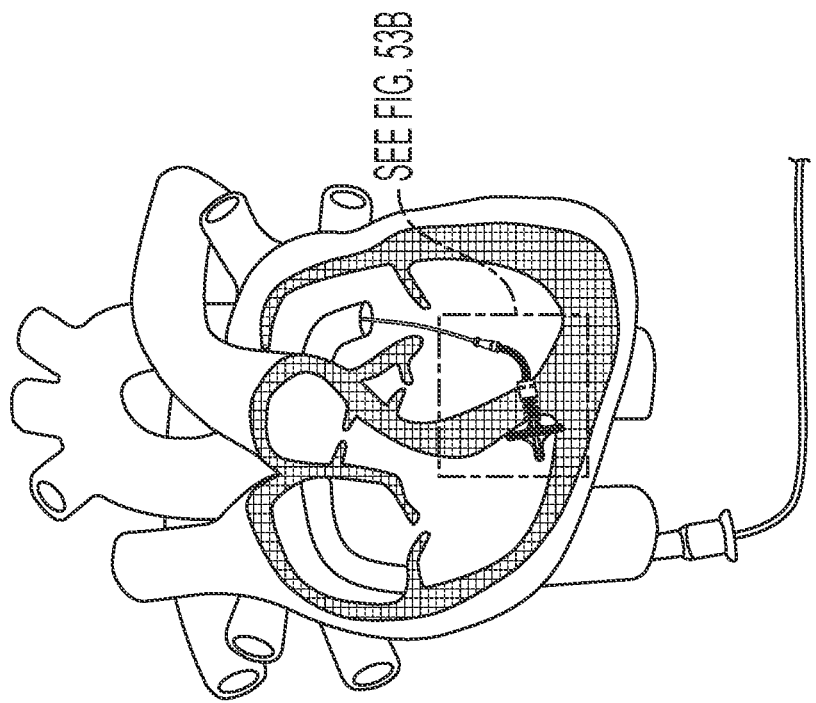
FIG. 53A is a cut-away perspective view of a heart with the single-stage anchor support delivered across the septum and connected to the delivery cable.

As shown in FIGS. 49A-B, reverse rotation of the head 155 of the threaded rod 154 turns the microcatheter holder 160 (FIG. 37), thereby turning the proximal control hub 166 of the microcatheter 161 (FIG. 13A), so that the microcatheter 161 retracts back out of the junction of the anchor torque driver 143 and the anchor cap 23 of the anchor 20. When this occurs, as shown in FIGS. 50-51, the coupling tabs 148 of the coupling arms 147 of the anchor torque driver 143 are released from the coupling recesses 24 of the anchor cap 23, thereby allowing the anchor torque driver 143 to be retracted from the anchor 20 as shown in FIG. 52. After the anchor torque driver 143 is disengaged the anchor support delivery system 140 is removed, leaving the distal flange delivery cable 60 in place. The same procedure is shown in FIGS. 53A and 53B in connection with the alternative distal flange 41.

The Method of Implanting the Proximal Flange

Figure 54B:
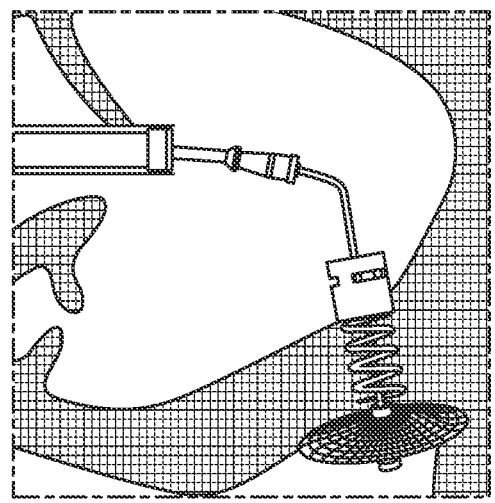
FIG. 54B is a magnified cut-away perspective view of a heart with the distal of the two-stage anchor support flange delivered across the septum and connected to the delivery cable.
Figure 54A:
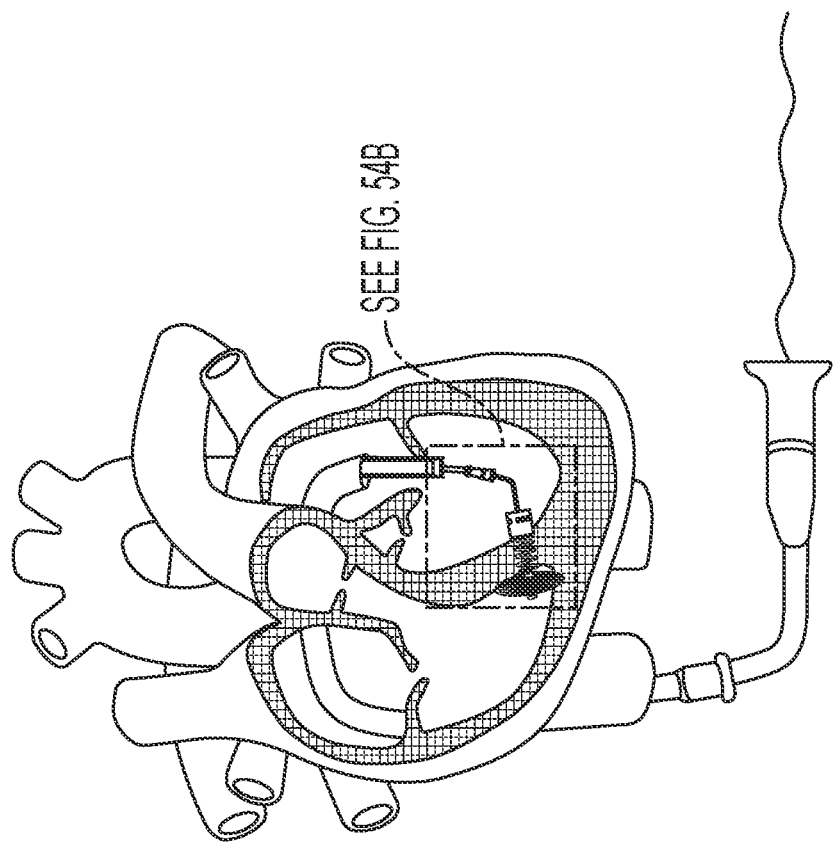
FIG. 54A is a cut-away perspective view of a heart with the distal flange of the two-stage anchor support delivered across the septum and connected to the delivery cable
Figure 55B:
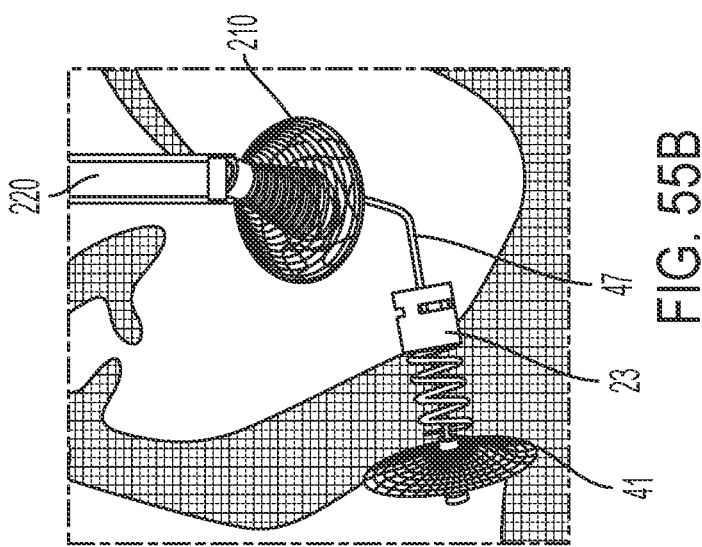
FIG. 55B is a magnified cut-away perspective view of a heart with a restraint of a proximal flange exiting the anchor delivery guide.
Figure 55A:
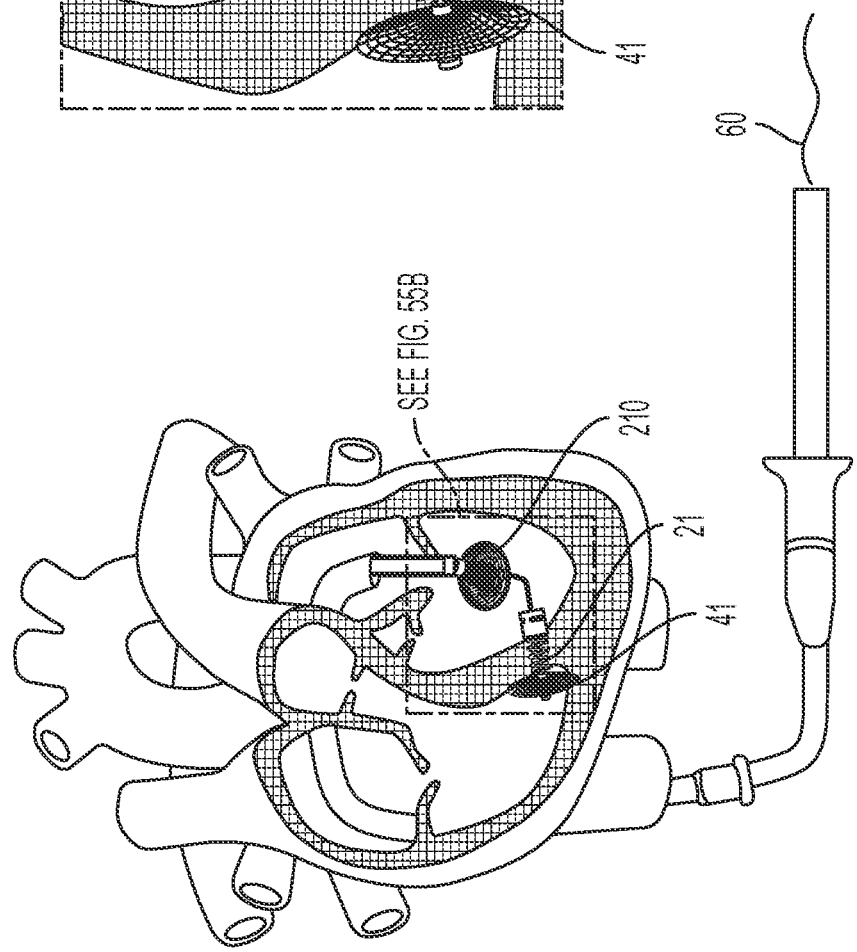
FIG. 55A is a cut-away perspective view of a heart with a restraint of a proximal flange exiting the anchor delivery guide.
Figure 57B:
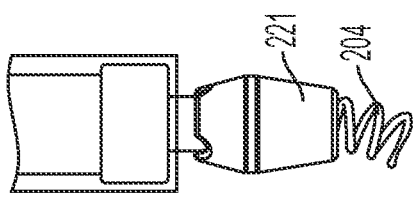
FIG. 57B is a magnified perspective view of the proximal flange delivery catheter tip outside of the anchor delivery guide.
Figure 57C:
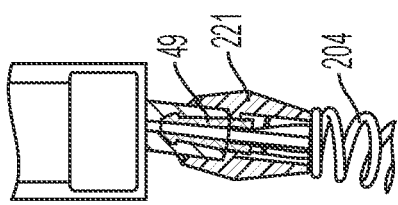
FIG. 57C is a cut-away view of FIG. 57B.
Figure 57A:
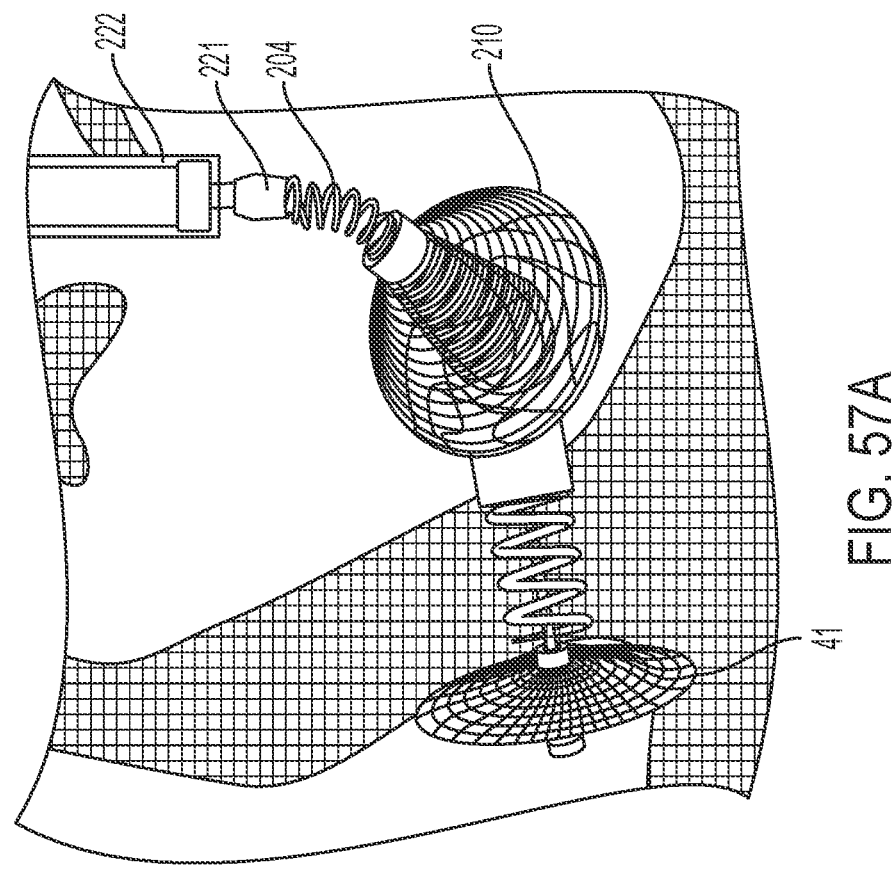
FIG. 57A is a magnified view of FIG. 56B.
Figure 58B:
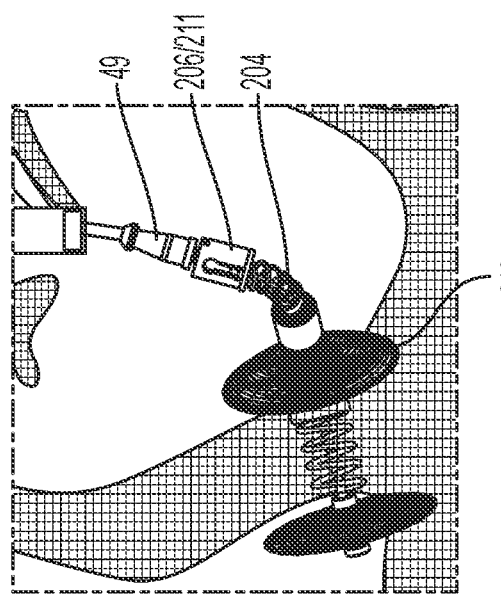
FIG. 58B is a magnified cut-away perspective view of a heart with the distal and proximal flanges deployed against the interventricular septum, with the distal flange connected to the anchor delivery cable.
Figure 58A:
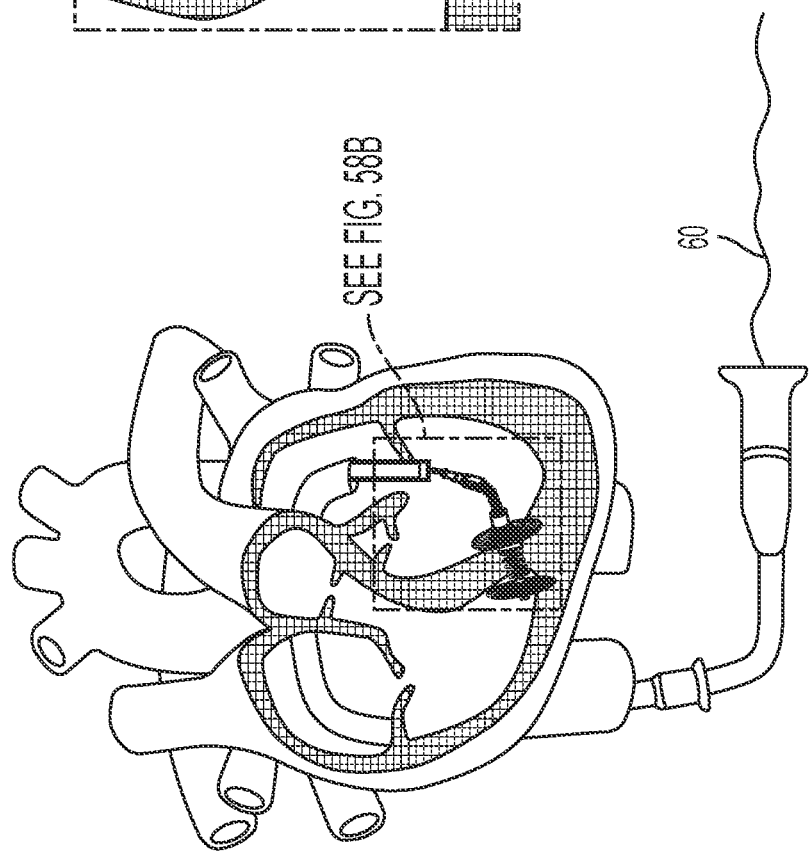
FIG. 58A is a cut-away perspective view of a heart with the distal and proximal flanges deployed against the interventricular septum, with the distal flange connected to the anchor delivery cable.

As shown in FIGS. 54A-D, representing a two-stage anchor support 245 having a proximal flange 210, the proximal flange 210, attached to the proximal flange delivery catheter 220 and collapsed within the proximal flange loader 280 having lumen 28 in FIG. 26, is threaded over the delivery cable 60 and is inserted into the proximal end of anchor delivery guide 130 in FIGS. 54C and 54D. Proximal flange delivery catheter 220 pushes the proximal flange 210 into the anchor delivery guide 130 when the proximal flange loader 280 is removed. As shown in FIGS. 55A-B, the proximal flange is pushed out of the anchor delivery guide 130 by the proximal flange delivery catheter 220, allowing the disk 201 to advance over the flex connector 47 and rod 46 via lumen 202 of proximal flange 210; once outside the tip of the anchor delivery guide 130, the disk 201 expands. Continued pushing of the proximal flange delivery catheter 220 advances the disk 201 until it approaches the interventricular septum 8 (or other intracardiac wall) as shown in FIGS. 56A-56B. Once the disk 201 contacts tissue, the proximal flange delivery catheter pushes the docking element 211 or 206, compressing the flexible compression element 204 until the docking element 211 or 206 goes over the end 50 flex connector base 49 of the flex connector 47. At this point the docking arms 208 or 213 bend inwards towards the flex connector base 49, locking the docking element below the end 50 of the flex connector base 49, preventing the docking element and associated proximal flange from moving proximally and the proximal flange is secured in its position. As tension is applied to the flex connector backwards via the tethering/locking systems associated with an intracardiac device, the flexible compression element, expanding against the secured docking element, urges the disk 201 forwards, providing a cantilever force to the anchor and distal flange.

The Method of Implanting the Tether System

Figure 53D:
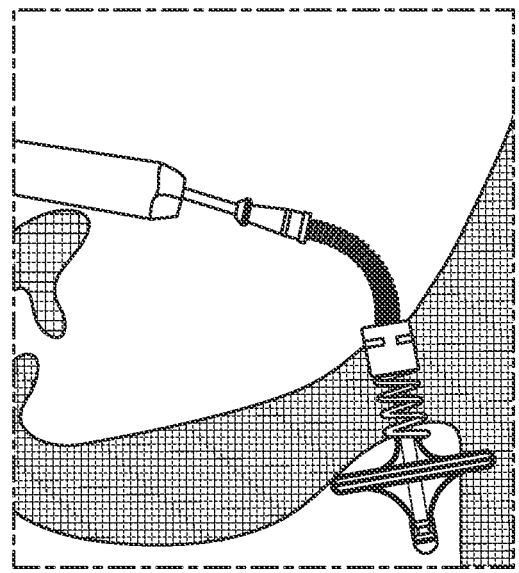
FIG. 53D is a magnified cut-away perspective view of the tether delivery system advancing to the flex connector of the anchor support.
Figure 53C:
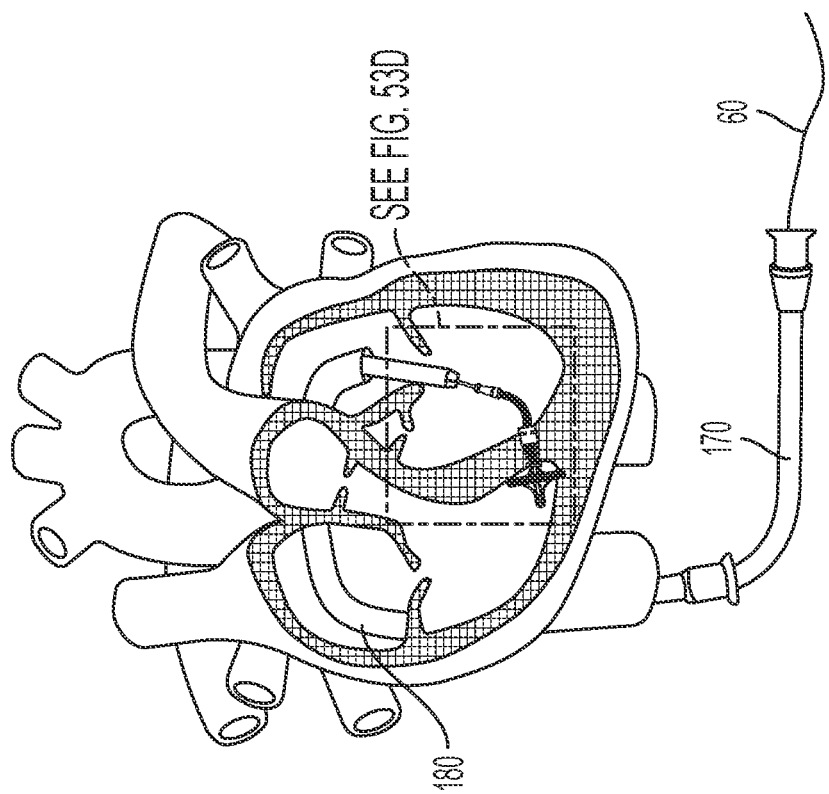
FIG. 53C is a cut-away perspective view of a tether delivery system advancing to the flex connector of the anchor support.
Figure 53F:
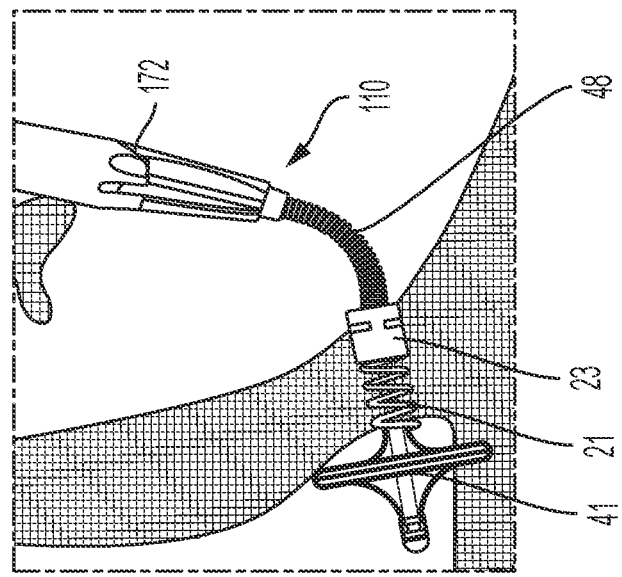
FIG. 53F is a magnified cut-away perspective view a tether assembly docked onto the flex connector base and tether delivery system retracting to expose tethers
Figure 53E:
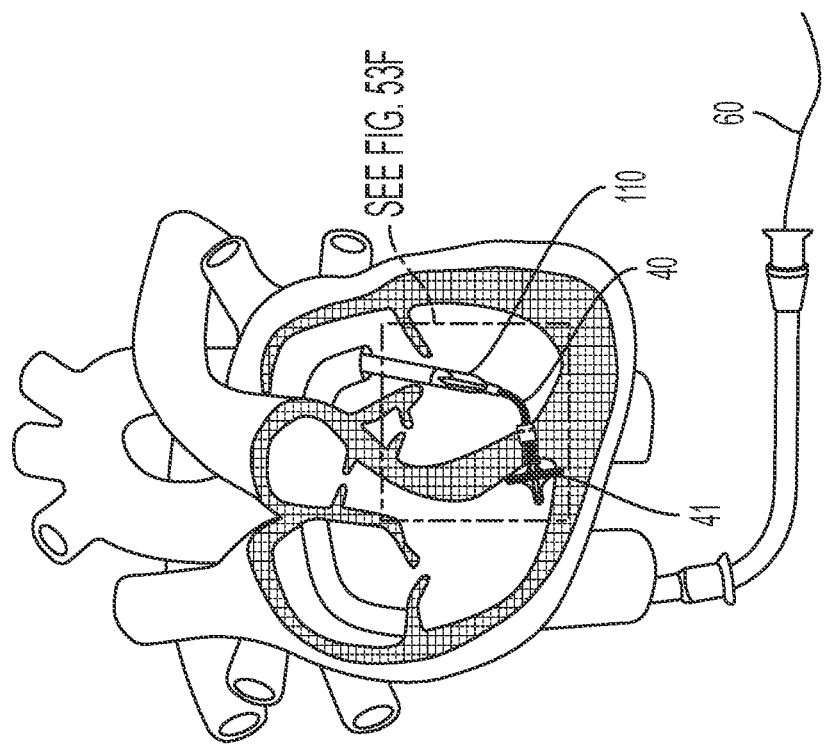
FIG. 53E is a cut-away perspective view of a tether assembly docked onto the flex connector base and tether delivery system retracting to expose tethers

As shown in FIG. 53C-D, the tether delivery system 170 is advanced over delivery cable 60 into trans-septal sheath 180, until the tether delivery system 170 exits the distal tip 182. As shown in FIGS. 53E-F, the single stage anchor support 45 is shown. It is to be understood that this is by way of example and the same tether delivery system 170 may be employed with the two-stage anchor support 245. Tracking over the delivery cable 60, the distal end 172 of the tether delivery system 170 docks onto the flex connector base 49 of the flex connector 47 or 48. After coupling of the tether assembly 110 to the flex connector base 49 occurs, the distal end 172 of the tether delivery system 170 may be retracted, leaving the tether assembly 110 connected to the anchor/anchor support assembly, as shown in FIG. 53E-F. The tether assembly 110 may be pre-connected to a transcatheter valve 100 or other intracardiac device, and the delivery cable 60 may be detached from the end 50 of the flex connector base 49, leaving behind, for example, a transcatheter valve connected via the tether assembly to the anchor/anchor support assembly.

The Tapered Anchor

Referring now to FIG. 59, at least one tapered anchor 900 includes a penetrating coil 902, stacked coil 903, funneled coil 904, and docking coil 906. In one aspect, the penetrating coil 902 is continuous with the stacked coil 903, which is continuous with the funneled coil 904, which is continuous with the docking coil 206. The docking coil 906 with distal end 907 is configured to reversibly attach to the anchor torque driver 143. The penetrating coil 902 of anchor 900 is configured to securely attach to an intracardiac wall such as the interventricular septum 8 of the heart 1. The tapered anchor 900, as shown, is sized and configured as a helix to fix to an intracardiac wall. Optionally, each section of tapered anchor 900 may be differentially sized by radius, length, or pitch of coil (e.g. wider/narrower radius and/or longer or shorter and/or coil density depending on patient-specific anatomy of the cardiac wall to which it attaches). In one aspect, any section of the tapered anchor 900 is composed of any known metal alloy, including, but not limited to, nitinol, titanium, or cobalt-chromium. In another aspect, any section of the tapered anchor 200 may be covered in synthetic membranes such as polytetrafluoroethylene (PTFE), expanded polytetrafluoroethylene (ePTFE) or polyethylene terephthalate (PET). In another aspect, any section of the tapered anchor 200 may be covered in biological tissue, such as bovine, ovine, porcine, or equine pericardium, or with any combination of anti-inflammatory drugs or other natural or synthetic compounds that might promote healing and limit inflammation. A tip(s) 901 at the end of the penetrating coil 902 of the tapered anchor 200 optionally is constructed and/or coated with the same or different materials as the rest of the tapered anchor 200 and may be fashioned as a blunt or sharp tip.

In use, the tapered anchor 900 is secured to the cardiac wall by rotating tapered anchor 900 until tip(s) 901 is at a desired depth in the cardiac wall. The depth to which the tapered anchor 900 is screwed in an adjustable manner according to not only the location within the heart but also the specific anatomy of a patient. For example, the tapered anchor 900 may be implanted more deeply into the thicker portion of the interventricular septum, or more deeply into a patient with a thicker interventricular septum. In another aspect, the stacked coil 903 of the tapered anchor 900 has a smaller coil angle, creating a denser coil that prevents the tapered anchor 900 from advancing further once the stacked coil 903 has contacted the cardiac wall. By reversing the rotation of the tapered anchor 900, it is removed safely from the cardiac wall, either to be repositioned, or to be removed entirely.

Rotation of the tapered anchor 900 occurs when the anchor torque driver 143 rotates the docking coil 906, which has coupled to the anchor torque driver distal end 146 (coupling mechanism not shown). The anchor torque driver distal end 146 remains coupled to the docking coil 906, while the microcatheter 161 is advanced and the anchor support 40 is implanted. After anchor support 40 has been implanted, similar to anchor/anchor support assembly illustrated in 46A-B, the anchor restraint 43 abuts the end of the penetrating coil 202 of the tapered anchor 900, with the funneled coil 904 extending over the proximal portion 44 of the anchor restraint 43 and over the rod 46 of anchor support 45. In another aspect, the docking coil 906 is configured to couple around the flex connector 47 or 48 of anchor support 45, respectively. The flex connector base 49 abuts the end 207 of the docking coil 906 of the tapered coil 900, ready to accept the tether 110 as described above.

FIGS. 60-120

FIGS. 60-120 generally illustrate alternative configurations of the distal flange anchor restraint and alternative anchoring members other than a coil as shown in the preceding figures. It is to be understood that the distal flanges depicted therein may be employed with a single-stage anchor support or a two-stage anchor support having a proximal flange. The proximal flange anchor restraint may also assume any configurations shown with regard to the distal flange anchor restraint.

The Anchor Support with Inflatable Elements

Referring to FIGS. 60-61, the anchor support 40 may include the anchor support shown in FIG. 60 or anchor support 301 shown in FIG. 61. Anchor support, both consist of a distal inflatable element 302, proximal portion 303 of inflatable element 302, rod 304 ending in flex connector 306, attached to flex connector base 307. The distal inflatable element 302 may take any shape, including a any portion of a (or complete) sphere, cylinder, polyhedron, or torus. The distal inflatable element 302 may contain one or more metallic components, including, but not limited to, nitinol, stainless steel, titanium, or cobalt-chromium, stainless steel, and any portion of the one or more inflatable elements is composed of biological tissue, such as bovine, ovine, porcine, or equine pericardium, or synthetic membranes such as, but not limited to, polytetrafluoroethylene (PTFE) or polyethylene terephthalate (PET). In practice the distal inflatable element 302 is in a collapsed form with low profile until anchor support is in position, at which time any gaseous or liquid element is infused via the distal end 308 of flex connector base 307 such that the gaseous or liquid element goes through a channel (not illustrated) in inner lumen 311, until it exits proximal portion 303, thereby inflating distal element 302 until desired shape and size is obtained. In another aspect, proximal portion 303 and rod 304 are preferably composed of nitinol, but may composed of any known metal alloy, including, but not limited to titanium, or cobalt-chromium. In another aspect, the distal inflatable element 302 or rod 304 have additional fixation members (not shown) extending from any portion of surface to provide further engagement with tissue. Flex connector 306 is a nitinol wire like flex connector 47 or maybe a nitinol spring like flex connector 48. As either a nitinol wire or nitinol spring, flex connector 306 is of variable diameter, length, coil pitch and be composed of additional metallic alloys or polymeric plastics. FIG. 61 illustrates anchor support with all the characteristics of anchor support, but with a proximal inflatable element 309, that may take any shape and contain any material that distal inflatable element 302 takes, but the shape and/or material of proximal inflatable element 309 may differ from distal inflatable element 302. Like distal inflatable element 302, proximal inflatable element 309 begins as a deflated low-profile element and is inflated, at the same or at a different time, via infusion of a gaseous or liquid element via the distal end 308 of flex connector base 307 through a channel (not illustrated) in lumen 311. According to another aspect, the gaseous or liquid element infused into either inflatable element is exchanged for any type of polymeric resin. Like distal inflatable element 302, proximal inflatable element 309 can have additional fixation members (not shown) extending from any portion of surface to provide further engagement with tissue. In another aspect, any portion of the anchor support is covered in synthetic membranes such as polytetrafluoroethylene (PTFE), expanded polytetrafluoroethylene (ePTFE) or polyethylene terephthalate (PET), or covered in biological tissue, tissue, such as bovine, ovine, porcine, or equine pericardium, or with any combination of anti-inflammatory drugs or other natural or synthetic compounds that might promote healing and limit inflammation.

The Anchor Support with Radially Extending Elements

Referring to FIGS. 62-63, the anchor support 40 may include anchor support 320 which may convert from its undeployed form 321 to its deployed form 322. Anchor support 320 has a distal securing element 323 in a collapsed form shown in FIG. 52 or in an expanded form shown in FIG. 53. Distal securing element 323 is composed of one or more extension elements 324 generally bending backwards (concave). These extension elements 324 are connected via element base 325, which connects to the proximal section 326 of anchor support 320. The extension elements 324 are preferentially composed of nitinol metal, but any portion of them is composed of any metallic or plastic alloy and is covered anywhere along their length with biological or synthetic membranes. The extension elements 324 is spaced evenly or variably around the long axis of element base 325. The extension elements 324 is the same or different in diameter and length, and the cross section of each is the cross section of any polygon, circle, or ellipse, and each extension element may generally bend backwards (concave) in the shape of a circle, ellipse, parabola, any sinusoidal curve, or is shaped as the edge of any polygon; it is also understood that one of more extension elements 324 of distal securing element 323 may bend forwards (convex). The tip of each element is the same as each element, or is, but is not limited to, the shape of a barb, hook, prong, or the like. The components of proximal section 326 have the same structure and function as components 303, 304, 306-308, in FIGS. 60-61 except proximal section 326 does not have an inner lumen and does not serve to inflate any element.

Referring to FIGS. 64-65, the anchor support 40 includes anchor support 327 which converts from its undeployed form 328 to its deployed form 329. Anchor support 327 has distal securing element 331 in its undeployed form in FIG. 64, or in its deployed form in FIG. 65, with extension elements. These extension elements connect via element base 333 to proximal section 334. Like extension elements 324, extension elements 332 may have variability in location along the long axis of 333, may have any variability in material or shape properties. Also, although these extension elements 332 are general bending forwards (convex), one or more of these elements may bend forwards (convex). Proximal section 334 has the same characteristics as proximal section 326.

The Anchor Support with Helical Coil

Figures 68, 69:
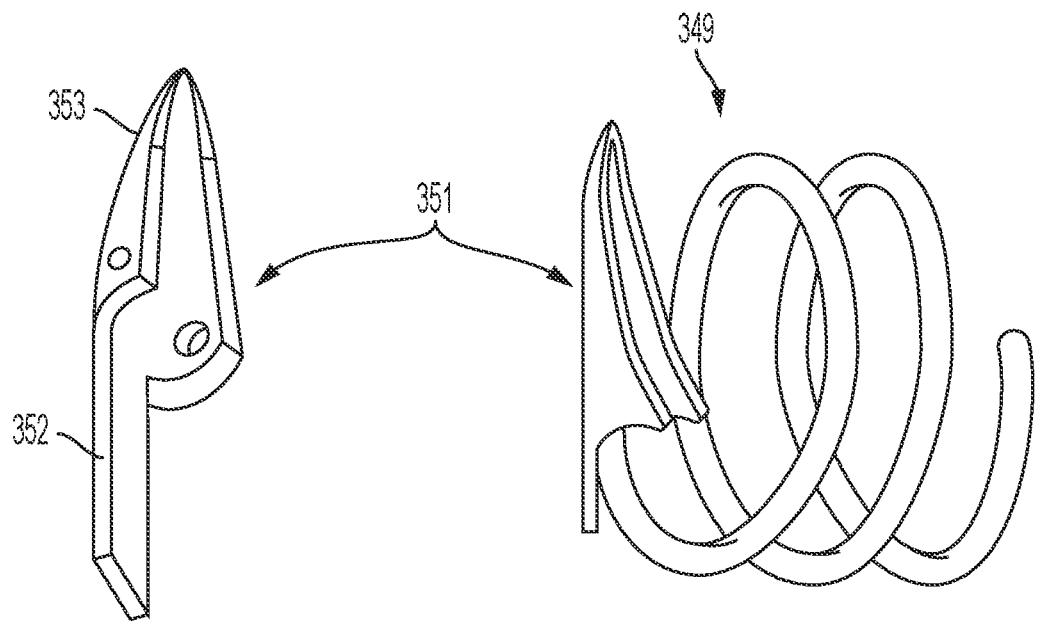
FIG. 68 is a side elevational view of an anchor coil ending in a trowel-like element.
FIG. 69 is a magnified perspective of the trowel-like element.

Referring to FIGS. 66-67, the anchor support 40 includes anchor support 340, which converts from its undeployed form 341 to its deployed form 342. Anchor support 340 has support coil 343, shown in its undeployed form in FIG. 66, and in its deployed form in FIG. 67. Support coil 343 is formed by wire 344, whose proximal end 347, is fixed to the distal end 349 of proximal element 348, and wire 344 is preferentially constructed of nitinol although either one may have any metallic alloy or plastic element, and any portion of either support coil is covered by either synthetic or biological membranes. Support coil 343, along its length, is differentially sized by radius, length, or pitch of coil (e.g. wider/narrower radius and/or longer or shorter and/or coil density depending on patient-specific anatomy of the cardiac wall to which it attaches). The tip 346 of support coil 343 is the same as rest of the coil, or is, but is not limited to, the shape of a barb, hook, prong, or even a straight rod; for purpose of example, FIGS. 68-69 illustrate an anchor coil which ends in a trowel element 351, composed of a trowel bar 352 and trowel head 353. Finally, proximal element 348 has the same material and shape properties as proximal section 326 in FIG. 63.

The Anchor Support with Helical Coil in Conical Shape

Referring to FIGS. 70-71, anchor support 45 includes anchor support 355 and converts from its undeployed form 356 to its deployed form 357. Anchor support 355 has anchor coil 358, shown in its undeployed form in FIG. 70, and shown in its deployed form in FIG. 71. Except for the shape of the anchor coil 358, anchor support 355 has all the subcomponents, and material/shape possibilities as anchor support 340.

The Anchor Support with Helical Coil in Two-Stage Process

Figures 72A, 72B, 72C:
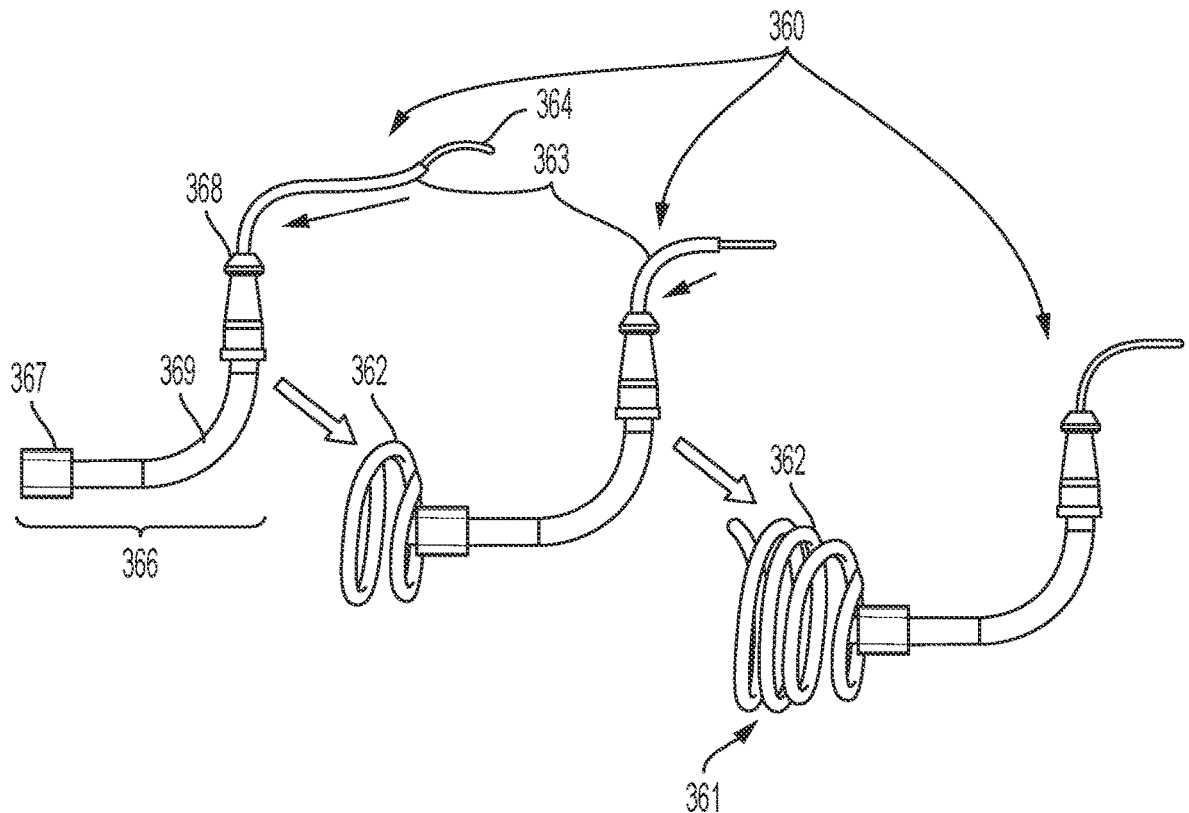
FIG. 72A is a side elevational view of an anchor support with a helical coil shaped like coil in FIG. 56, before it has been pushed through proximal segment.
FIG. 72B is a side elevational view of an anchor support with helical coil partially pushed through proximal segment.
FIG. 72C is a side elevational view an anchor support with helical coil pushed through proximal segment and fully deployed.

Referring to FIGS. 72A-C, anchor support 45 many include anchor support 360, where the anchor coil 361, is similar to anchor support 340 in FIGS. 66-67, but is not directly attached to the tip 367 of proximal section 366. Instead anchor coil 361 is in an elongated form as shown in FIG. 72A, and the proximal end 363 of anchor coil 361 is attached to delivery cable 364. Once proximal section 366 is in position, delivery cable 364 is pushed so that anchor coil 361 moves from the proximal tip 368 of proximal section 366, through channel 369, until the distal tip 362 of anchor coil 361, exits the distal tip 367 of proximal section 366. As the distal tip 362 of anchor coil exits 361, as shown in FIG. 62B, the anchor coil takes its preformed shape; as it exits fully, anchor coil 361 forms its fully preformed shape as shown in FIG. 72C. At this point, delivery cable 364 is disengaged from the proximal end 363 of anchor coil 361. Otherwise, the material and shape properties of anchor support 360 mirror those of anchor support 340 in FIGS. 66-67.

The Anchor Support with Covered Helix

Referring to FIGS. 73-74, the anchor support 45 includes anchor support 380, which may convert from its undeployed form 381 to its deployed form 382. Anchor support 380 as a distal covered helix 383, in its undeployed form in FIG. 73, and in its deployed form in FIG. 74. The distal covered helix 383 is formed by a support wire 384, which is preferentially constructed of nitinol although it may have any metallic alloy or plastic element, and along its length is differentially sized by radius, length, or pitch of coil. The support wire 384 is covered by synthetic and/or biological membrane 386 across the diameter of each loop, so that helical coil formed by support wire 384 is a covered helix much like a compressed Archimedes screw.

The Anchor Support with Umbrella/Parachute-Like Element(s)

Now referring to FIGS. 75-76, the anchor support 40 includes anchor support 390 shown in FIG. 75, or anchor support 391 shown in FIG. 76. Anchor support 390 has distal umbrella element 392. Umbrella element 392 has one or more umbrella petals 393. Each umbrella petal 393 has a wire frame 394, preferentially composed of nitinol, although any portion of the frame is any metallic or plastic element and is covered by any synthetic or biological membrane. Spanning the wire frame 394 is a membrane 396, which may be any synthetic or biological membrane. Each umbrella petal 393 may be the same or different from the other petal, and may take the shape of polygon, circle, ellipse, or sinusoidal curve in the X-Y plane, and any portion may curve in a convex/concave or sinusoidal fashion in the Z-plane toward the cardiac wall. Anchor support 391 has distal parachute element 398. Parachute element 398 is formed by a wire frame 399, also preferentially nitinol, although any portion of the frame may contain any metallic or plastic element and is covered by any synthetic or biological membrane. The parachute element 398 may take the shape of any parachute or sail-like shape, may have any number or shape of struts (not shown) spanning the element 398, and is covered by any type of synthetic or biological membrane. Finally, proximal elements 397 and 402 have the same material and shape properties as proximal section 326 in FIG. 63.

The Anchor Support with Star-Like Element(s)

Now referring to FIGS. 77-78, the anchor support 40 includes anchor support 410, which converts from its undeployed form 411 to its deployed form 412. Anchor support 410 has a star element 413 that traverses the septum as a slotted hypotube with a distal end 414, proximal end 416 and one or more deformable members 417 between the ends. The star element 413 is preferably composed of cobalt-chromium and nitinol, although any portion of it is constructed of any metallic alloy or plastic polymer and covered with either synthetic or biological membranes. The distal 414 and proximal 416 ends have the cross-sectional area of a circle, ellipse, or any polygon, and the deformable members 417 also have any cross-section shape and deform along one or more junctions to form any polygonal shape. As a matter of example, the deployed form 412 shows the deformable members 417 taking the shape of triangles. Also, any deformable member 417 may take the same or different shape as any other deformable member. The proximal element 418 have the same material and shape properties as proximal section 326 in FIG. 62.

The Anchor Support with Pivoting Bar Element(s)

Now referring to FIGS. 79-80, the anchor support 40 includes anchor support 430, which convert from its undeployed form 431 to its deployed form 432. Anchor support 430 has a bar element 433, which has a distal end 434, pivot element 436, and proximal end 437. The bar element 433 have any diameter or length and have any straight or curved shape along its long axis, with its cross-sectional areal is any circle, ellipse, or polygon. The pivot element 436 is any shape and located anywhere along the long axis of bar element 433. Both the bar and pivot elements are constructed of any metallic allow or plastic polymer, is covered by any synthetic or biological membrane and may or may not have additional fixation members on its surface (not shown). Deployment wire 438, also constructed of any metallic alloy or plastic polymer, is attached to pivot element 436 and extends through lumen (not shown) of proximal element 439, until wire 438 exits the proximal end 441 of proximal element 439. Thus, deployment wire, through pushing or pulling can assist in deploying the bar element 433. Alternatively, deployment wire 438 is a spring or coil and connects to distal end 442 of proximal element 439 such that when bar element 433 exits microcatheter and is in free space, the bar element 433 pivots and then is pulled taut against the distal end 442 of the proximal element 439.

The Anchor Support Delivery System without Anchor Coil

When the anchor support delivery system 140 is be used to deliver an anchor support without using anchor 20, the anchor support delivery system 140 is combined with an alternative embodiment of the anchor torque driver 143, which does not have one or more coupling arms 147 and tabs 148. Instead the end 146 of this alternative embodiment of anchor torque driver 143 is connected directly and irreversibly to fixation elements 450, 460, or 470. Also, these fixation elements attached to anchor torque driver 143 are be used to stabilize the anchor delivery 130, so that microcatheter 161 has a stable platform to traverse the cardiac wall. FIG. 81-82 shows a fixation element 450 that has one or more protrusions 451 attached to fixation element base 452, which is attached to the distal end of anchor torque driver 143. The one or more protrusions 451 are shaped as a needle, barb, hook, spear, circle, ellipse, or as any polyhedron. Any portion of the fixation element 450, including the one or more protrusions 451, is composed of any metallic alloy or plastic polymer and may be coated with any synthetic or biological membrane.

As shown in FIGS. 83-84, is an alternative fixation element 460 attached to anchor torque driver 143. Fixation element 460, has one or more extension members 461, with tip 462 and base 463. The one or more extension members 461 may be of any length or diameter, have the cross-section of a circle, ellipse, or any polygon. Along the long axis, the extension member is straight, be any type of curve, or any portion of the perimeter of a polygon. The tip 462 may or be the same shape as rest of the extension member 461, or is shaped as needle, barb, hook, spear, circle, ellipse, or as any polyhedron. Base 463 of each extension member 461 is attached to fixation element base 464, and each base 463 may or may not have a pivot element, joint, or spring to allow the extension member 461 to bend inwards or outwards to any degree. Any portion of fixation element 460 is composed of any metallic alloy or plastic polymer and may be coated with any synthetic or biological membrane.

As shown in FIGS. 85-86, fixation element 470 is attached to anchor torque driver 143 via element base 474. Fixation element 470 is in the shape of a suction cup with a frame 471, inlet 472, and covering surface 473. Fixation element 470 may be frusto-conical in structure, or its base might be any type of circle, ellipse, or polygon, and the rest of the suction cup could also be in the shape of any part of a polygon. The frame 471 is constructed of any metallic alloy or plastic polymer, and the covering surface 473 may be any synthetic or biological membrane. Around the perimeter of the inlet 472, additional fixation elements such as microneedles (not shown) may be provided. Finally, a lumen (not shown) within base 474 extending through anchor torque driver all the way to beginning of the anchor support delivery system is used to create negative pressure so that the fixation element 470 further adheres to the cardiac wall.

The Method of Stabilizing the Anchor Delivery Sheath without Anchor

As shown in FIGS. 87A-B, the delivery system 140 attached to fixation element 450 is inserted into the anchor delivery sheath 130 until the fixation element 450 extends outside the distal tip 132 of the anchor delivery sheath 130 and engages the interventricular septum 8. After microcatheter delivery and anchor support delivery, the fixation element 450 is disengaged from the intraventricular septum 8 with retraction of the delivery system 140.

As shown in FIGS. 88A-B, the delivery system 140 attached to fixation element 460 is inserted into the anchor delivery sheath 130. While within the anchor delivery sheath 130, fixation element 460 is constrained. Namely, extension members 461 may be closer together when the extension members pivot close together by the freedom of movement given by a pivot element at base 463 of each extension member 461. Alternatively, the extension members 461 are constructed of nitinol so that the members are constrained with the sheath before exiting the tip of anchor delivery sheath 130. Once the fixation element 460 exits distal tip 132 of anchor delivery sheath 130, the extension members 461, either through action of a pivot element at each base 463 or through the members forming pre-formed shape of nitinol, extend radially outward as they affix to the interventricular septum 8. Additionally, the tip 462 of each extension member 461 is shaped (as a barb, spear, hook, needle, etc.) so as to engage tissue of the interventricular septum. After microcatheter delivery and anchor support delivery, the fixation element 460 is disengaged from the intraventricular septum 8 with retraction of the delivery system 140. As the delivery system 140 retracts, the extension members 461 move inwards so that they are pulled inside the distal tip 132 of anchor delivery sheath 130.

As shown in FIGS. 89A-B, the delivery system 140 attached to fixation element 470 is inserted into anchor delivery sheath 130. While in the sheath, element 470 is constrained by the diameter of the anchor delivery sheath 130, but upon exit of distal tip 132, element 470 expands to its pre-formed size. The suction cup adheres to the interventricular septum 8 through passive action, additional active fixation elements (not shown) and/or negative pressure exerted to element 470 through the delivery system 140. After microcatheter delivery and anchor support delivery, the fixation element 470 is disengaged and retracted back into anchor delivery sheath 130 by retraction of the delivery system 140.

The Method of Advancing Microcatheter without Anchor Coil

As illustrated in FIGS. 90-92, the microcatheter with screw tip dilator traverses the septum without the anchor coil, using an alternative fixation element. For purposes of illustration, the fixation element 450 is being shown, although the same process can be used with fixation elements 460 or 470. All the same steps described above are used as well.

Method of Advancing Microcatheters with Alternative Mechanisms

The methods of advancing the microcatheter also apply to microcatheters with alternative tip dilators. For example, FIG. 93 shows a microcatheter, but instead of screw tip dilator 162, as needle tip dilator 480 penetrates tissue. Needle tip dilator 480 may be of any known shape in the art and may be composed of any metallic alloy or plastic polymer and covered with any biological or synthetic membrane. Also, needle tip dilator 480 may rotate as screw tip dilator does or may have a swivel mechanism to stay in same position as the body of the needle tip dilator advances forward.

FIG. 94 shows a radiofrequency tip dilator 490. Radiofrequency tip dilator 490 is connected via a radiofrequency cable 491, which connects to radiofrequency generator 492. Radiofrequency tip dilator 490 delivers radiofrequency energy to the tissue while being advanced. It is also contemplated that the radiofrequency generator 492 and cable 491 could also connect to other tip dilators.

FIG. 95 shows a laser tip dilator 500. Laser tip dilator might be any type of laser that administers laser light impulses as the laser tip dilator and microcatheter are being advanced through the tissue.

FIG. 96 shows a rotating burr tip dilator 510. The rotating burr has any spherical, ellipsoid, or polyhedral shape, and is made of any metallic alloy and be covered by any cutting elements that may also be made of any metallic allow or gem, such as diamonds. The rotating burr tip dilator 510 is connecting to rotating cable 511, which is connected to power source 512. The rotating burr tip dilator 510, rotates clockwise or counterclockwise at any revolutions per minute. The rotating burr tip dilator 510, like other tip dilators, is advanced as by rotation of the microcatheter control knob 156.

FIG. 97 shows a helical tip dilator 520. The helical tip dilator 520 may take any of the shape or material properties as described for the anchor coil described above. In practice, the helical tip dilator 520 traverses the interventricular septum in exactly the same way as the screw tip dilator as described above.

FIG. 98 shows an oscillating tip dilator 530. The oscillating tip dilator 530 may take any shape and is composed of any metallic alloy or plastic polymer. Oscillating tip dilator 530 is connected to oscillator rod 531 which is connected to oscillator motor 532. Oscillator motor 532, when activated, pushes the oscillator rod 531 to and fro, thereby moving the oscillator tip dilator 530 back and forth, at any hertz, along the long axis of the microcatheter.

Examples of Other Anchor Supports Connected Via the Tether Assembly

As illustrated in FIGS. 99-120, any of the other anchor supports is connected to the tether assembly with or without the anchor, just as anchor support 40 is connected to the tether assembly with or without the anchor.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

The invention claimed is:

1. A minimally invasively implanted anchor support for securing a medical device to a heart wall, the anchor support comprising:
 an anchor securing member defining a lumen wherein said anchor securing member is configured to extend through the heart wall;
 a distal flange having a proximal end and distal end wherein said distal end of said distal flange includes an anchor restraint configured for securing to a heart wall and said proximal end of said distal flange includes a flex connector and wherein said anchor restraint is expandable and configured for securing to a heart wall
a
wherein said anchor restraint of said distal flange is compressed for implantation and when positioned within said anchor securing member lumen during implantation of said anchor support and said anchor securing member lumen is in the heart wall and wherein said anchor restraint extends beyond a distal end of said anchor member lumen and expands against the heart wall for anchoring against the heart wall; and
a proximal flange, said proximal flange comprising an expandable anchor restraint on its distal end and a flexible compression element extending proximally from said proximal flange anchor restraint wherein said anchor restraint of said proximal flange defines a lumen which is positioned along and receives said flex connector of said distal flange for implantation wherein said anchor restraint of said proximal flange contacts the heart wall after implantation on an opposing heart wall of said anchor restraint of said distal flange wherein said anchor restraints of said distal flange and said proximal flange anchor the medical device on the heart wall.

2. The minimally invasively implanted anchor support according to claim 1 wherein said distal flange further comprises a rod extending proximally from said anchor restraint of said distal flange and connecting to said flex connector.

3. The minimally invasively implanted anchor support according to claim 1 wherein said distal flange further comprises a flex connector base on a proximal end of said flex connector.

4. The minimally invasively implanted anchor support according to claim 1 wherein said anchor securing member is an anchor coil.

5. The minimally invasively implanted anchor support according to claim 4 wherein said anchor coil is a helical coil having a sharp distal tip for penetrating the heart wall.

6. The minimally invasively implanted anchor support according to claim 1 wherein said flex connector is a wire.

7. The minimally invasively implanted anchor support according to claim 1 wherein said flex connector is an expandable coil.

8. The minimally invasively implanted anchor support according to claim 1 wherein said proximal flange further comprises a docking element on a proximal end of said flexible compression element.

9. The minimally invasively implanted anchor support according to claim 8 wherein said docking element comprises at least one outwardly biased docking arm.

10. The minimally invasively implanted anchor support according to claim 8 wherein said docking element comprises at least one inwardly biased docking arm.

11. The minimally invasively implanted anchor support according to claim 1 wherein said proximal flange, said flexible compression element and said docking element each define a hollow lumen wherein a continuous lumen extends therethrough.

12. The minimally invasively implanted anchor support according to claim 1 wherein said flexible compression element is a coil.

13. The minimally invasively implanted anchor support according to claim 1 wherein a proximal end of said flex connector includes a flex connector base and said minimally invasively implanted anchor support further comprises a tether swivel configured to cooperate with said flex connector base.

* * * * *